(12) United States Patent
Zheng et al.

(10) Patent No.: US 11,964,996 B2
(45) Date of Patent: Apr. 23, 2024

(54) 2-ALKYNYLMANNOSE DERIVATIVE AND APPLICATION THEREOF

(71) Applicant: Jiyue Zheng, Suzhou (CN)

(72) Inventors: Jiyue Zheng, Suzhou (CN); Xiaolei Wang, Suzhou (CN)

(73) Assignee: Jiyue Zheng, Suzhou (CN)

( * ) Notice: Subject to any disclaimer, the term of this patent is extended or adjusted under 35 U.S.C. 154(b) by 108 days.

(21) Appl. No.: 17/956,774

(22) Filed: Sep. 29, 2022

(65) Prior Publication Data

US 2023/0105576 A1    Apr. 6, 2023

Related U.S. Application Data

(63) Continuation of application No. PCT/CN2021/084235, filed on Mar. 31, 2021.

(30) Foreign Application Priority Data

Mar. 31, 2020    (CN) .......................... 202010246993.6

(51) Int. Cl.
*C07H 15/203*    (2006.01)
*C07H 17/02*    (2006.01)

(52) U.S. Cl.
CPC ........... *C07H 15/203* (2013.01); *C07H 17/02* (2013.01)

(58) Field of Classification Search
None
See application file for complete search history.

(56) References Cited

FOREIGN PATENT DOCUMENTS

| CN | 102753562 A | 10/2012 |
|---|---|---|
| CN | 105682665 A | 6/2016 |
| CN | 107849031 A | 3/2018 |
| CN | 108778288 A | 11/2018 |
| CN | 108883122 A | 11/2018 |
| WO | WO2020012336 A1 | 1/2020 |

OTHER PUBLICATIONS

Alzeer, Helvetica Chimica Acta—vol. 78 (1995). (Year: 1995).*
Title of the Item: Journal of Medicinal Chemistry Publication Date: Mar. 26, 2012 Name of the Author: Han Zhenfu et al. Article Title: Lead optimization studies on FimH antagonists: discovery of potent and orally bioavailable ortho-substituted biphenyl mannosides pp. 3945-3959.
Title of the Item: Journal of Medicinal Chemistry Publication Date: May 27, 2010 Name of the Author: Han Zhenfu et al. Article Title: Structure-Based Drug Design and Optimization of Mannoside Bacterial FimH Antagonists pp. 4779-4792.

* cited by examiner

*Primary Examiner* — Layla D Berry
(74) *Attorney, Agent, or Firm* — Nitin Kaushik

(57) ABSTRACT

The present disclosure relates to 2-alkynylmannose Derivative and Application Thereof. The mannose derivatives, and a pharmaceutically acceptable salt, an isotope, and an isomer thereof have a structure shown as formula I:

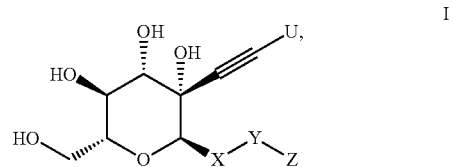

and are used for treating or preventing bacterial infections. The present disclosure also provides pharmaceutically acceptable compositions comprising the above compounds and their use in the treatment or prevention of bacterial infections.

12 Claims, 3 Drawing Sheets

2-ALKYNYLMANNOSE DERIVATIVE AND APPLICATION THEREOF

CROSS-REFERENCE TO RELATED APPLICATIONS

The present disclosure claims priority of Patent Application No. 202010246993.6 entitled "2-alkynylmannose Derivative and Application Thereof", filed on Mar. 31, 2020, in China, the entire content of which is incorporated herein by reference.

TECHNICAL FIELD

The present disclosure relates to a 2-alkynylmannose derivative and application thereof, and belongs to the technical field of medicines.

BACKGROUND

Urinary tract infections (UTIs), also known as urinary system infections, refer to urinary tract inflammations caused by pathogens invading the mucosa or tissue of the urinary tract. UTIs include pyelonephritis, cystitis, and urethritis, and are one of the most common infectious diseases. UTIs will cause pain, burning pain, and frequent urination, and spread to the kidney and blood and become life-threatening in severe cases. Nearly 100 million people worldwide suffer from UTIs every year, and more than 2.5 billion dollars is spent on treatment. UTIs are prone to recurrence, and 25-44% of female patients will get re-infected within 6 months (usually about 1 quarter) after antibiotic therapy. However, recurrent UTIs are susceptible to antibiotic resistance. Therefore, it is urgent to develop new treatment methods (Tamadonfar K O et al., Microbiol Spectrum, 2019, 7(3): BAI-0014-2019).

More than 80% of UTIs are caused by uropathogenic *Escherichia coli* (UPEC). FimH proteins are apical proteins of UPEC type I fimbriae, and are a key factor in bacterial infection of urinary tract cells. FimH proteins can specifically bind to mannose glycoproteins on the surface of bladder epidermal cells, causing bacteria to adhere to the surface of the bladder and avoid being washed away by urine. FimH proteins also induce local rearrangement of host cells rather than directly mediate invasion of UPEC, causing recurrent UTIs. Therefore, FimH proteins have emerged as a candidate target protein for preventing or treating bacterial UTIs. Animal experiments have shown that unlike antibiotic therapy, which involves massive killing of intestinal florae and great changes in colonies, FimH protein inhibitors can selectively scavenge UPEC in the bladder and the intestinal tract with less impact on other intestinal bacteria, and are expected to be used for preventing or treating UTIs (Terlizzi M. E. et al., Front. Microbiol. 2017, 8, 1566).

Inflammation bowl disease (IBD) is a chronic relapsing inflammatory disease of the intestine, which mainly includes Crohn's disease (CD) and ulcerative colitis (UC). IBD presents a slow onset in most cases and an abrupt onset in a few cases with different severity, and is prone to recurrence. In recent years, the morbidity of IBD has been increasing, especially in newly industrialized countries in regions such as Asia, South America, and the Middle East. The specific pathogenesis of IBD is still unclear, and is generally believed to be the result of the combined action of multiple factors such as immune system imbalance and intestinal flora imbalance (de Souza H S et al., Nat Rev Gastroenterol Hepatol. 2016, 13, 13-27).

Recent studies on intestinal florae in patients with IBD have shown that the number of colonies of adherent-invasive *Escherichia coli* (AIEC) in the patients is significantly increased compared with normal people, and AIEC plays an important role in the occurrence and progress of IBD (Alvarez Dorta, D. et al., Chem Bio Chem 2016, 17, 936-952). Similar to UPEC, AIEC also colonizes in the intestinal tract through the binding of apical FimH proteins of AIEC I type fimbriae to receptors CEACAM6 on intestinal epidermal cells. Relying on the binding of FimH proteins to the receptors CEACAM6, AIEC can further enter epidermal cells and immune cells of the intestinal tract to induce inflammatory responses and immune disorders (Mydock-McGrane L K et al., Expert Opin Drug Discov. 2017, 12, 711-731).

The existing treatment of IBD mainly adopts non-steroidal anti-inflammatory drugs or immunosuppressants. However, these treatment methods can only relieve symptoms, and the disease will relapse. Therefore, it is urgent to develop new treatment methods. There are a few clinical and preclinical studies on use of antibiotics to scavenge AIEC for treatment of IBD, but the effect of antibiotics is unclear because antibiotics also have a killing effect on other intestinal florae, especially probiotics, which can further lead to intestinal flora imbalance. Some studies even show that intestinal flora imbalance caused by antibiotics will further promote the infection of AIEC and is a causative factor in the occurrence and progress of IBD (Oberc A M et al., Inflamm Bowel Dis. 2019, 25(4), 711-721). Animal experiments have shown that FimH protein inhibitors block the colonization of AIEC in the intestinal tract by antagonizing the binding of FimH proteins to the receptors CEACAM6 to scavenge AIEC in the intestinal tract and are expected to be used for treating and preventing IBD (Alvarez Dorta, D. et al., Chem Bio Chem 2016, 17, 936-952).

SUMMARY

An objective of the present disclosure is to provide a 2-alkynylmannose derivative capable of inhibiting the function/activity of FimH proteins and application thereof. The 2-alkynylmannose derivative can effectively inhibit the function/activity of FimH proteins, and can be used for preventing or treating a disease or a disorder that is improved by inhibiting the function/activity of FimH proteins.

The objective of the present disclosure is achieved by the following technical solutions.

A 2-alkynylmannose derivative, and a pharmaceutically acceptable salt, an isotope, and an isomer thereof have a structure shown as formula I:

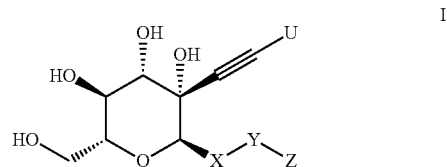

where, U is a hydrogen atom, a deuterium atom, $C_{1-10}$ alkyl, $C_{3-10}$ cycloalkyl, $C_{2-10}$ alkenyl, $C_{2-10}$ alkynyl, a six- to ten-membered aromatic ring, a five- to ten-membered heteroaromatic ring that contains 1 to 4 heteroatoms selected from N, O, and S, or a five- to seven-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_1$ groups;

X is a chemical bond, an oxygen atom, a sulfur atom, $N(R_2)$, $C(R_2)(R_3)$ or —C≡C—;

Y is a chemical bond, $C_{1-10}$ alkyl, $C_{3-10}$ cycloalkyl, $C_{2-8}$ alkenyl, $C_{2-8}$ alkynyl, a six- to fourteen-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_4$ groups;

Z is selected from a hydrogen atom, a deuterium atom, a halogen, cyano, $C_{1-10}$ alkyl, $C_{3-10}$ cycloalkyl, $C_{1-10}$ alkoxy, $C_{2-8}$ alkenyl, $C_{2-8}$ alkynyl, —C(O)OR$_5$, —C(O)NR$_5$R$_6$, —N(R$_5$)C(O)R$_6$, —S(O)$_2$R$_5$, —S(O)$_2$NR$_5$R$_6$, —P(O)R$_5$R$_6$, a six- to fourteen-membered aromatic ring, a five- to fourteen-membered heteroaromatic ring that contains 1 to 4 heteroatoms selected from N, O, and S, and a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_7$ groups;

$R_1$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ureido, $C_{1-8}$ carbamato, $C_{1-8}$ sulfonamido, $C_{1-8}$ ester, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, and a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy;

$R_2$ and $R_3$ are each independently selected from a hydrogen atom, a deuterium atom, a halogen, hydroxyl, amino, $C_{1-8}$ alkyl, and $C_{3-8}$ cycloalkyl, and the alkyl and the cycloalkyl are unsubstituted or substituted with 1 to 3 substituent groups selected from a deuterium atom, a halogen, hydroxyl, $C_{1-3}$ alkyl, $C_{3-5}$ cycloalkyl, and $C_{1-3}$ alkoxy;

$R_4$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ureido, $C_{1-8}$ carbamato, $C_{1-8}$ sulfonamido, $C_{1-8}$ ester, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, and a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, $C_{1-3}$ alkoxy, and $C_{5-10}$ phenol;

$R_5$ and $R_6$ are each independently selected from a hydrogen atom, $C_{1-8}$ alkyl, and $C_{3-8}$ cycloalkyl, and the alkyl and the cycloalkyl are unsubstituted or substituted with 1 to 3 substituent groups selected from a deuterium atom, a halogen, hydroxyl, $C_{1-3}$ alkyl, $C_{3-5}$ cycloalkyl, and $C_{1-3}$ alkoxy; and $R_7$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ureido, $C_{1-8}$ carbamato, $C_{1-8}$ sulfonamido, $C_{1-8}$ ester, dimethylphosphoryl, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, and a five-to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

Preferably, in the above 2-alkynylmannose derivative, U is a hydrogen atom, a deuterium atom, $C_{1-10}$ alkyl, $C_{3-10}$ cycloalkyl, a six-to ten-membered aromatic ring, a five-to ten-membered heteroaromatic ring that contains 1 to 4 heteroatoms selected from N, O, and S, or a five- to seven-membered heterocyclic ring that contains 1 or 2 heteroatoms selected from N, O, and S, and the alkyl, the cycloalkyl, the aromatic ring, the heteroaromatic ring, and the heterocyclic ring are unsubstituted or substituted with 1 to 5 $R_1$ groups;

X is an oxygen atom or —C≡C—;

Y is a chemical bound, $C_{1-10}$ alkyl, $C_{3-10}$ cycloalkyl, a six- to ten-membered aromatic ring, a five- to ten-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the aromatic ring, the heteroaromatic ring, and the heterocyclic ring are unsubstituted or substituted with 1 to 5 $R_4$ groups;

Z is selected from a hydrogen atom, a deuterium atom, a halogen, cyano, $C_{1-10}$ alkyl, $C_{3-10}$ cycloalkyl, $C_{1-10}$ alkoxy, $C_{2-8}$ alkenyl, $C_{2-8}$ alkynyl, —C(O)OR$_5$, —C(O)NR$_5$R$_6$, —N(R$_5$)C(O)R$_6$, —S(O)$_2$R$_5$, —S(O)$_2$NR$_5$R$_6$, —P(O)R$_5$R$_6$, a six- to ten-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_7$ groups;

$R_1$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ sulfonamido, $C_{1-8}$ ester, $C_{1-8}$ alkyl, $C_{3-8}$ cycloalkyl, $C_{1-8}$ alkoxy, phenyl, a five- or six-membered heteroaromatic ring that contains 1 to 3 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy;

$R_4$ is selected from a hydrogen atom, a deuterium atom, a halogen, cyano, hydroxyl, amino, $C_{1-8}$ sulfonyl, $C_{1-8}$ alkyl, $C_{3-8}$ cycloalkyl, $C_{1-8}$ alkoxy, phenyl, a five- or six-membered heteroaromatic ring that contains 1 to 3 heteroatoms selected from N, O, and S, or a five- to seven-membered heterocyclic ring that contains 1 or 2 heteroatoms selected from N, O, and S, and the alkyl, the cycloalkyl, the alkoxy, the phenyl, the heteroaromatic ring, and the heterocyclic ring are unsubstituted or substituted with 1 to 3 substituent groups selected from a deuterium atoms, a halogen, hydroxyl, cyano, $C_{1-3}$ alkyl, $C_{3-5}$ cycloalkyl, $C_{1-3}$ alkoxy, and $C_{6-10}$ phenol;

$R_5$ and $R_6$ are each independently selected from a hydrogen atom, $C_{1-8}$ alkyl, and $C_{3-8}$ cycloalkyl, and the alkyl and the cycloalkyl are unsubstituted or substituted with 1 to 3 substituent groups selected from a deuterium atom, a halogen, hydroxyl, $C_{1-3}$ alkyl, $C_{3-5}$ cycloalkyl, and $C_{1-3}$ alkoxy; and $R_7$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ester, dimethylphosphoryl, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 or 3 substituent groups selected from a deuterium atom, a halogen, hydroxyl, cyano, $C_{1-3}$ alkyl, $C_{3-5}$ cycloalkyl, and $C_{1-3}$ alkoxy.

Preferably, in the above 2-alkynylmannose derivative, Y is $C_{1-8}$ alkyl, $C_{3-10}$ cycloalkyl, a six- to ten-membered aromatic ring, or a five- to ten-membered heteroaromatic ring that contains 1 to 4 heteroatoms selected from N, O, and S, and the alkyl, the cycloalkyl, the aromatic ring, and the heteroaromatic ring are unsubstituted or substituted with 1 to 5 $R_4$ groups; and $R_4$ is selected from a hydrogen atom, a deuterium atom, a halogen, cyano, hydroxyl, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

$R_4$ is selected from a hydrogen atom, a deuterium atom, a halogen, cyano, hydroxyl, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

Preferably, in the above 2-alkynylmannose derivative, the mannose derivative according to any one of claims 1 to 3 is characterized in that Y is selected from the following groups that are unsubstituted or substituted with 1 to 3 $R_4$ groups, the left side of Y is connected to X, the right side of Y is connected to Z, and the $R_4$ group is as defined above:

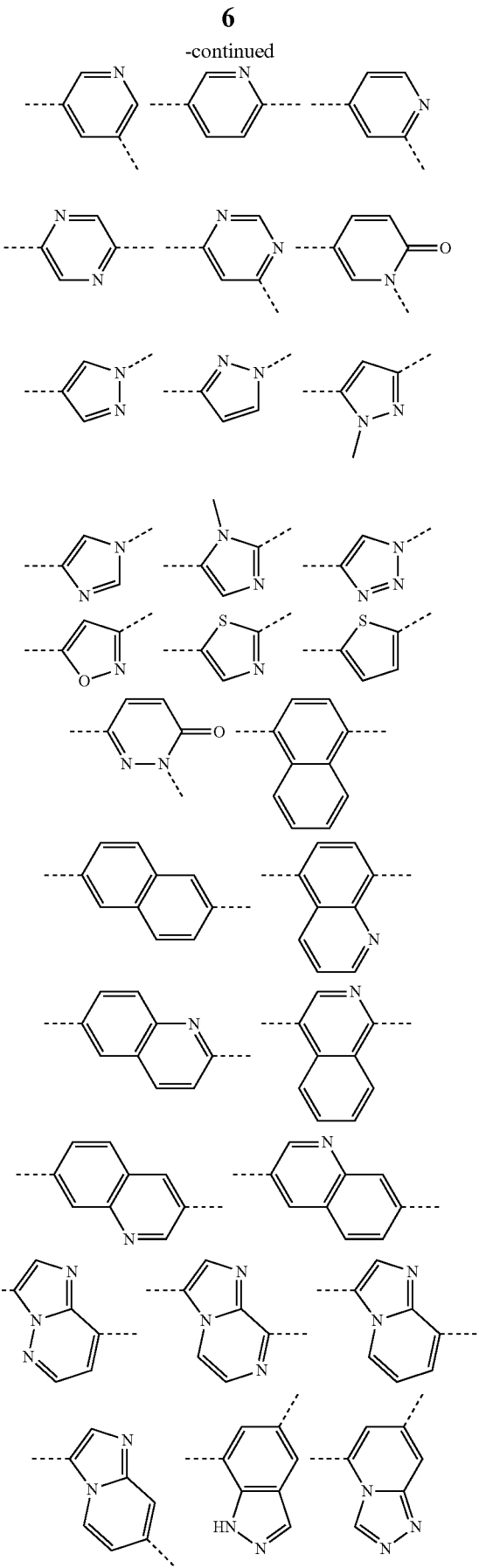

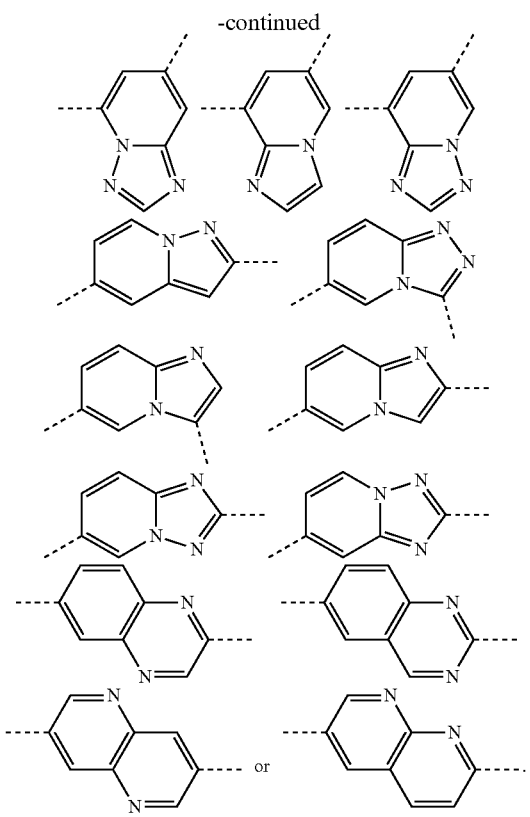

Preferably, the above 2-alkynylmannose derivative has a structure shown as formula Ia:

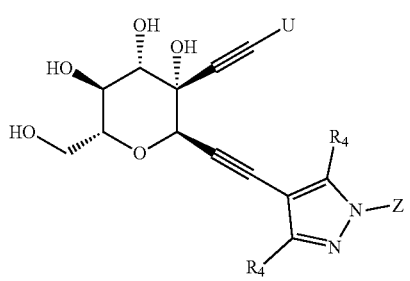

where, $R_4$ is selected from a hydrogen atom, a deuterium atom, a halogen, cyano, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

Preferably, in the above 2-alkynylmannose derivative, U is $C_{1-10}$ alkyl, $C_{3-10}$ cycloalkyl, a six- to ten-membered aromatic ring, or a five- to ten-membered heteroaromatic ring that contains 1 to 4 heteroatoms selected from N, O, and S, and the alkyl, the cycloalkyl, the aromatic ring, and the heteroaromatic ring are unsubstituted or substituted with 1 to 5 $R_1$ groups; and $R_1$ is selected from a hydrogen atom, a deuterium atom, a halogen, cyano, hydroxyl, amino, $C_{1-8}$ sulfonyl, $C_{1-8}$ amido, $C_{1-8}$ sulfonamido, $C_{1-8}$ ester, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

Preferably, in the above 2-alkynylmannose derivative, U is selected from the following groups that are unsubstituted or substituted with 1 to 5 $R_1$ groups, and $R_1$ is as defined above:

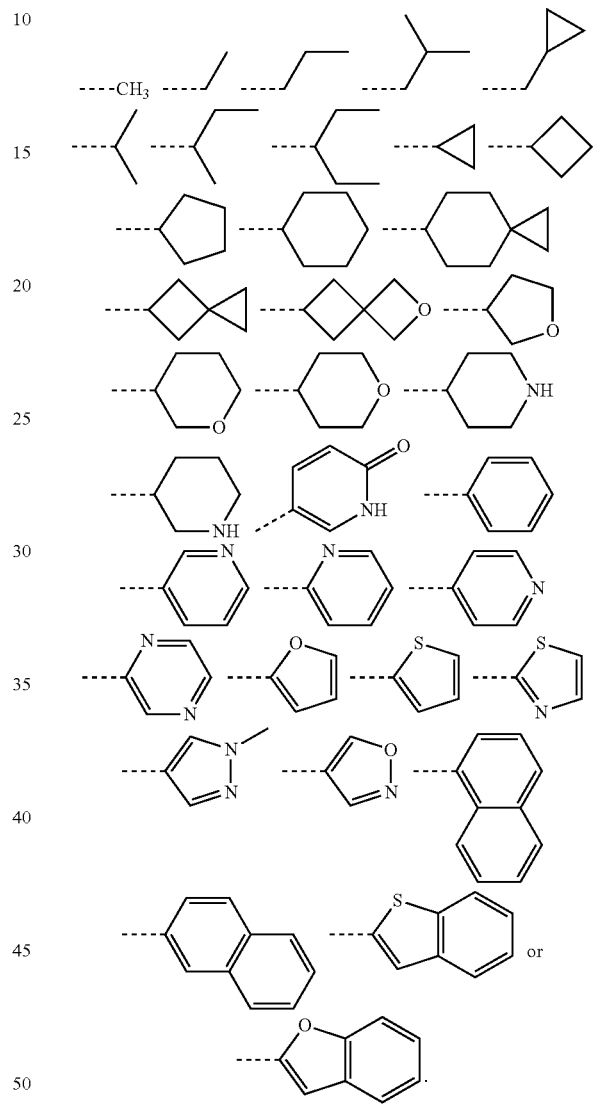

Preferably, in the above 2-alkynylmannose derivative, Z is selected from a hydrogen atom, a deuterium atom, a halogen, cyano, $C_{1-10}$ alkyl, $C_{3-10}$ cycloalkyl, $C_{1-10}$ alkoxy, a six- to ten-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkoxy, the aromatic ring, the heteroaromatic ring, and the heterocyclic ring are unsubstituted or substituted with 1 to 5 $R_7$ groups; and $R_7$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ester, dimethylphosphoryl, $C_{1-8}$ alkyl, $C_{3-8}$ cycloalkyl, $C_{1-8}$ alkoxy, phenyl, a fiveor six-membered heteroaromatic ring that contains 1 to 4 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 or 3 substituent groups selected from a deuterium atom, a halogen, hydroxyl, cyano, $C_{1-3}$ alkyl, $C_{3-5}$ cycloalkyl, and $C_{1-3}$ alkoxy.

Preferably, in the above 2-alkynylmannose derivative, Z is selected from the following groups that are unsubstituted or substituted with 1 to 5 $R_7$ groups, and $R_7$ is as defined above:

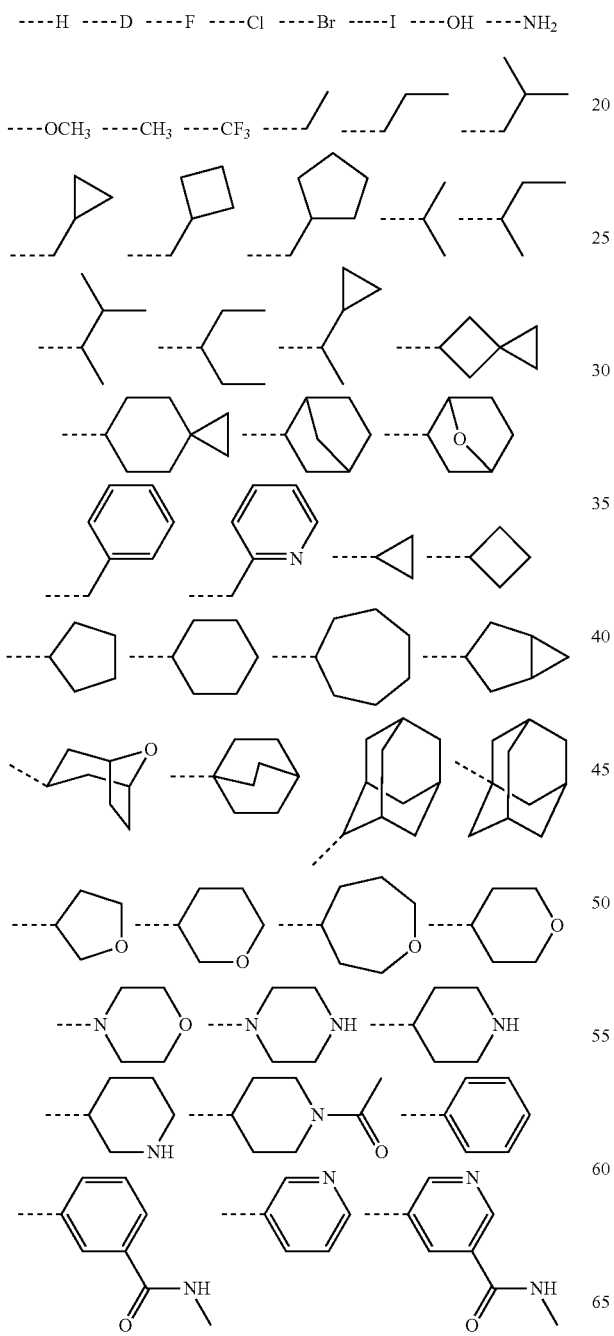

Preferably, in the above 2-alkynylmannose derivative, Y is selected from the following groups that are unsubstituted or substituted with 1 to 3 $R_4$ groups, the left side of Y is connected to X, the right side of Y is connected to Z, and $R_4$ is as defined above:

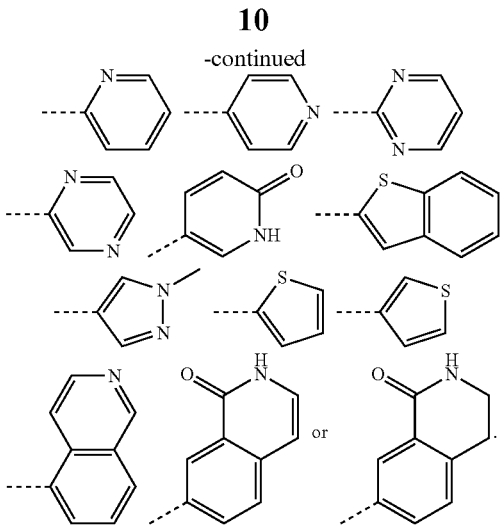

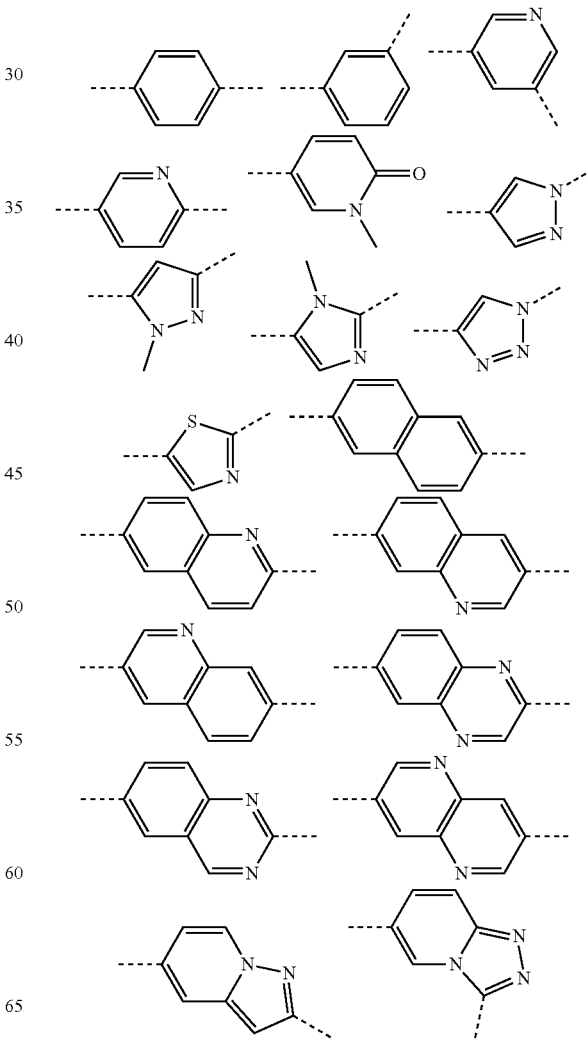

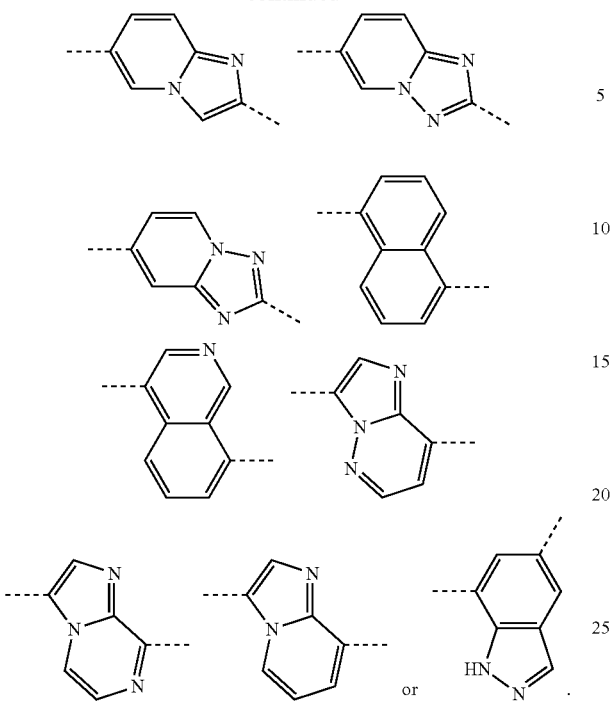
Preferably, the above 2-alkynylmannose derivative includes:
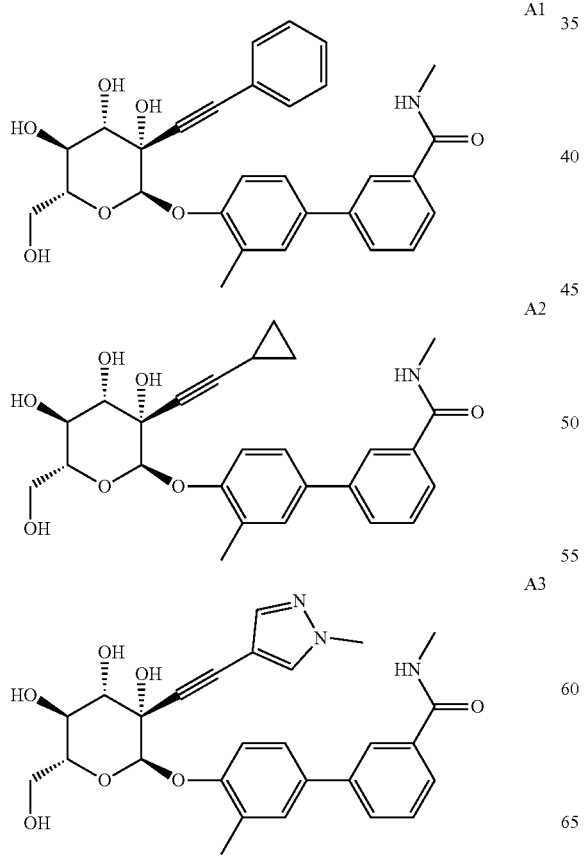
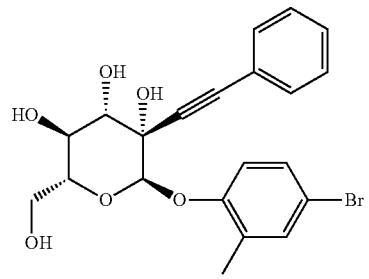
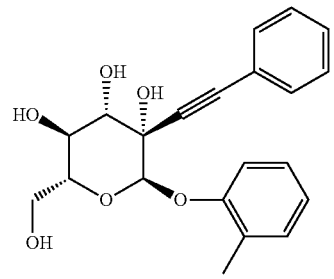
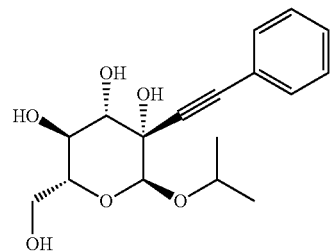
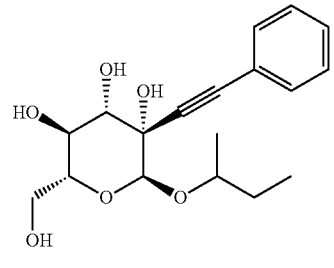
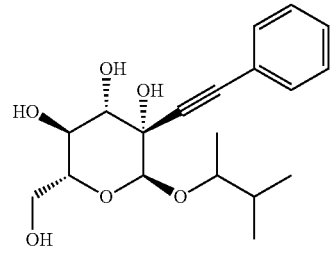
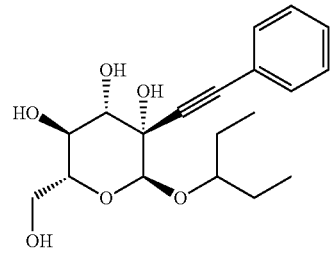

-continued
A10
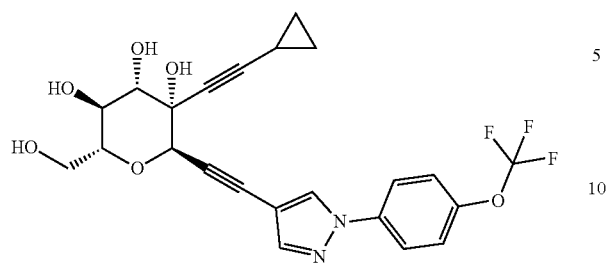
A11
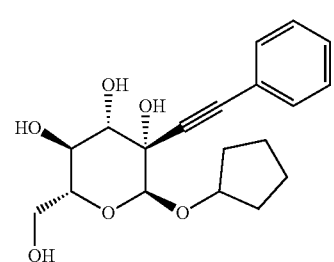
A12
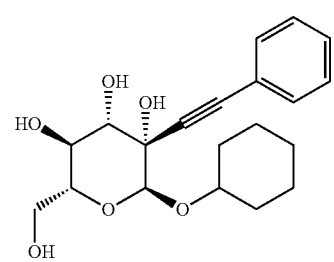
A13
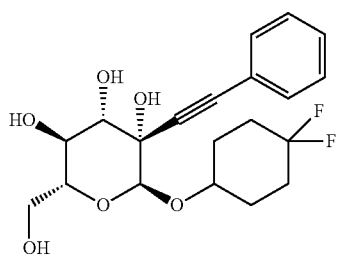
A14
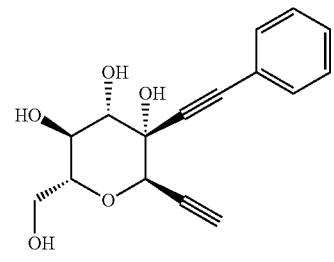
A15
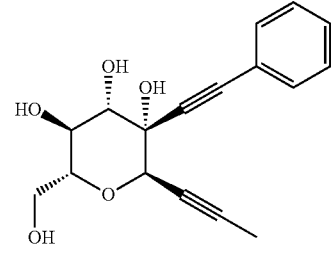
-continued
A16
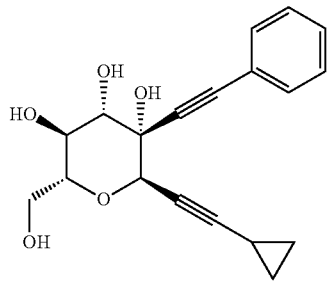
A17
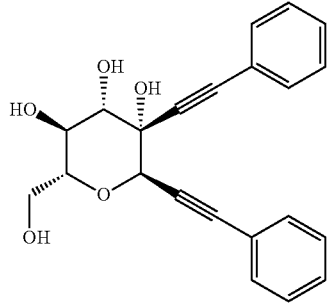
A18
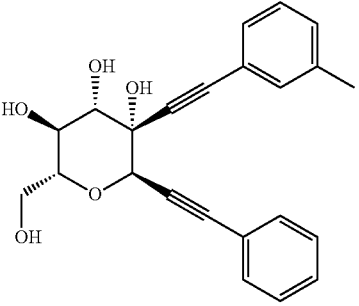
A19
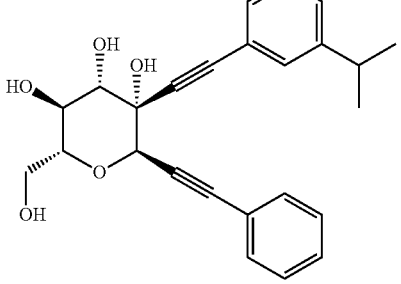
A20
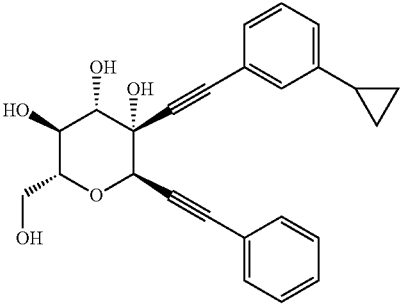

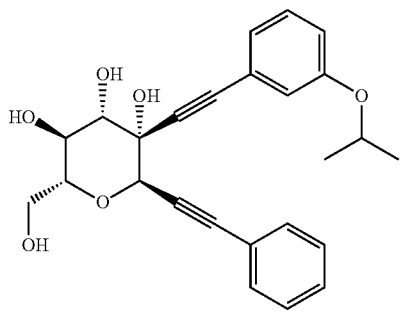
A21
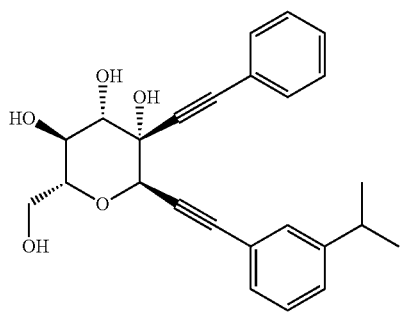
A26
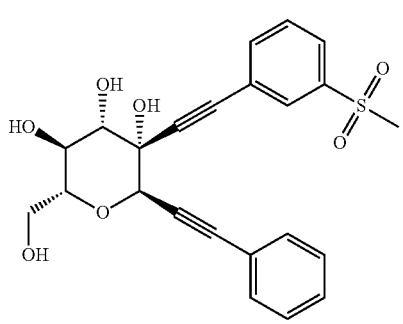
A22
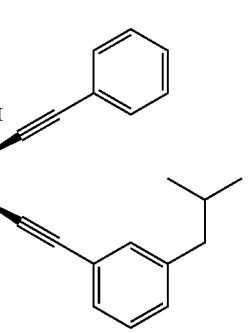
A27
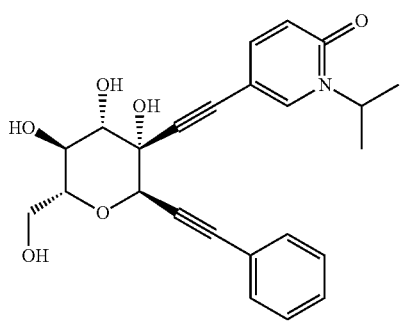
A23
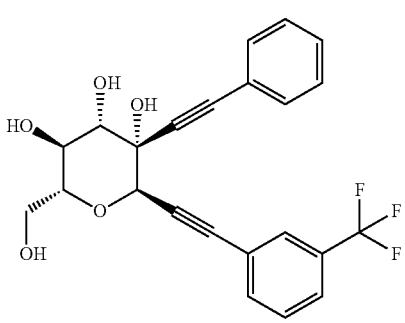
A28
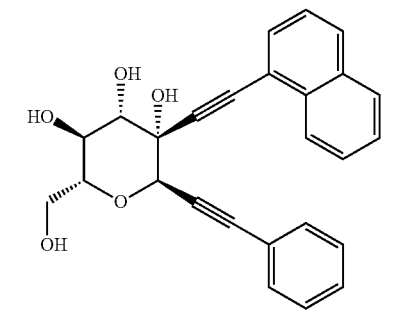
A24
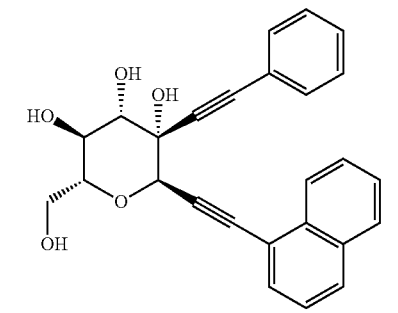
A29
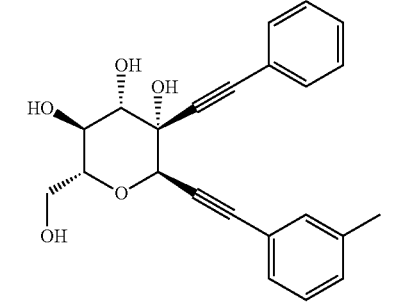
A25
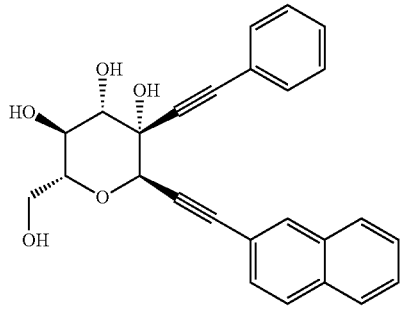
A30

| | |
|---|---|
| 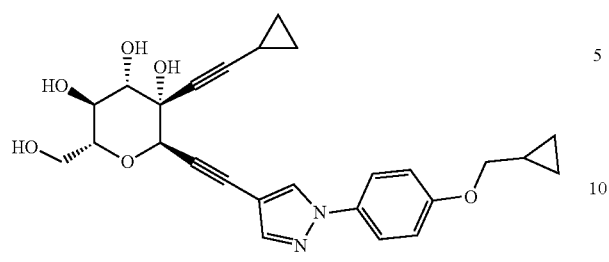 A31 | 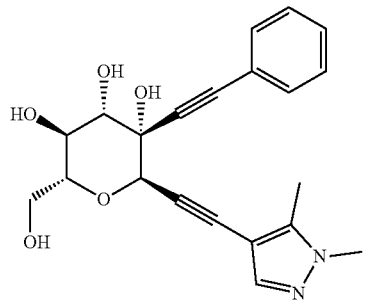 A36 |
| 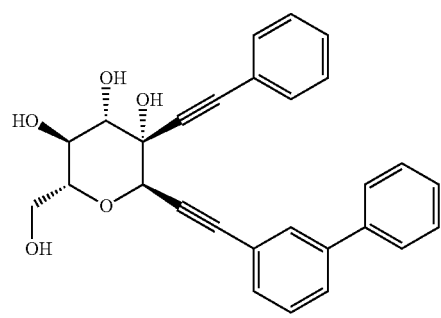 A32 | 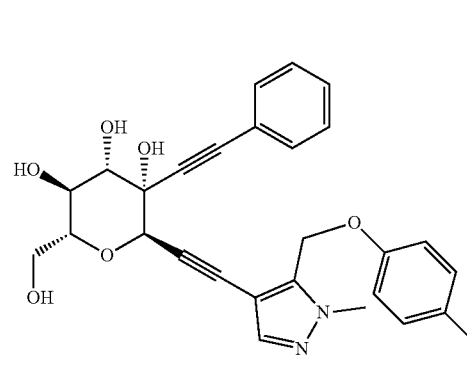 A37 |
| 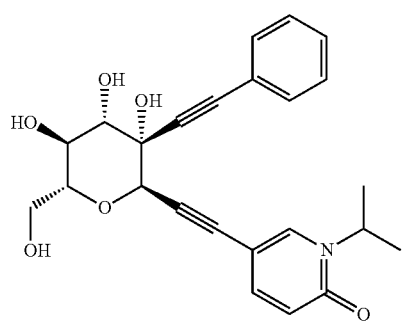 A33 | 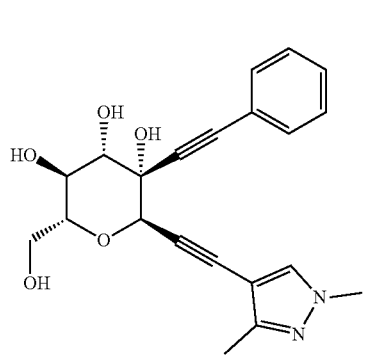 A38 |
| 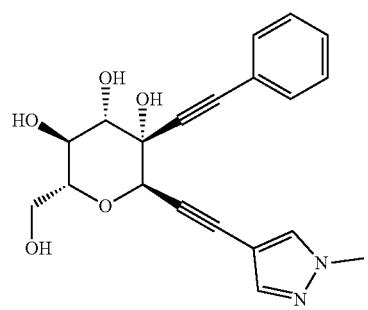 A34 | 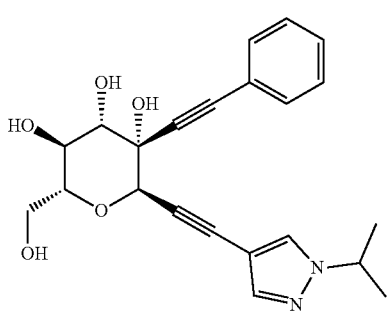 A39 |
| 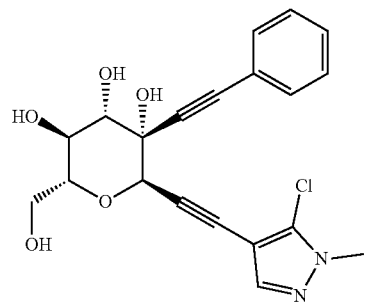 A35 | 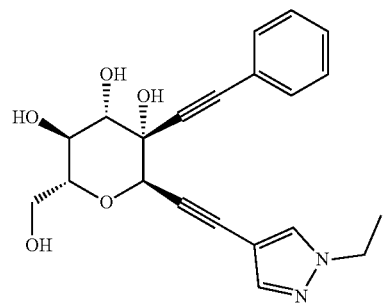 A40 |

-continued
A41
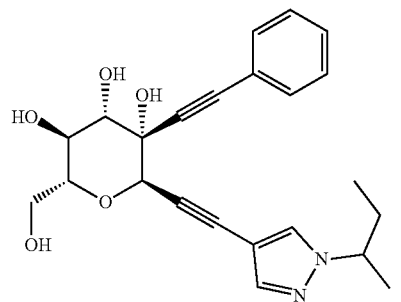
A42
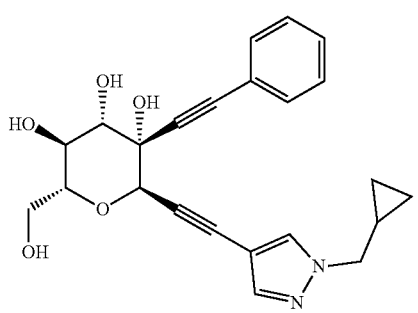
A43
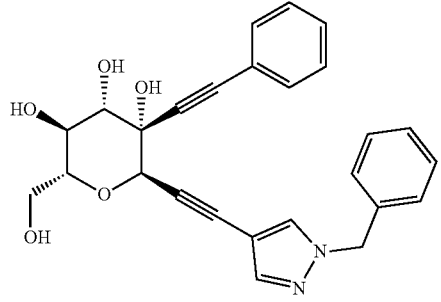
A44
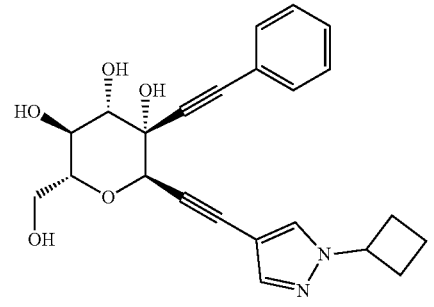
A45
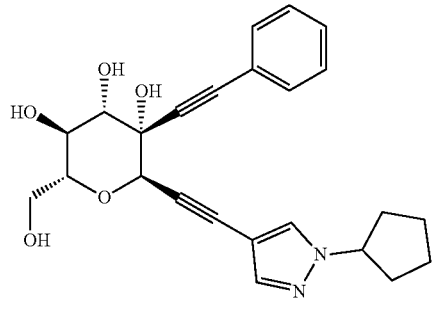
-continued
A46
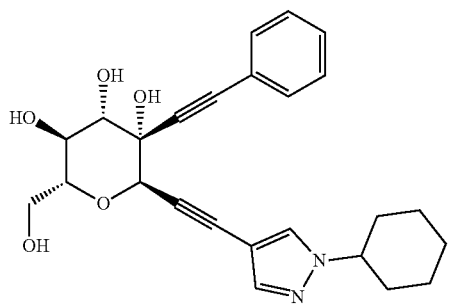
A47
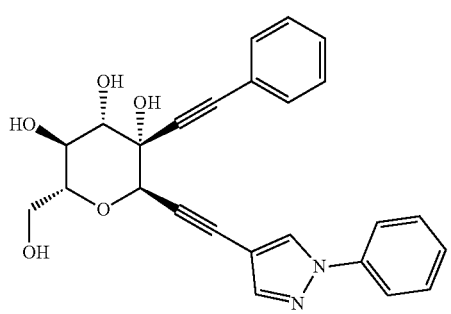
A48
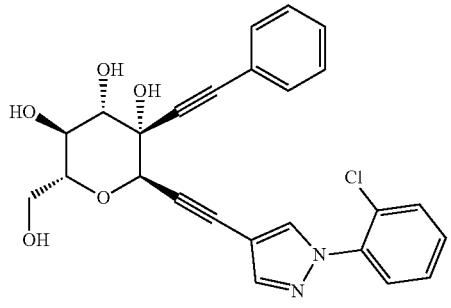
A49
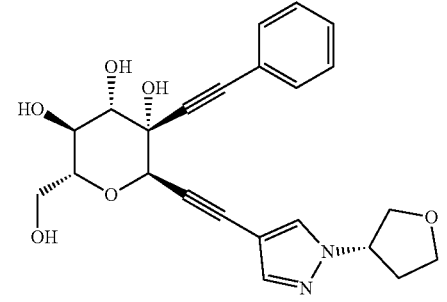
A50
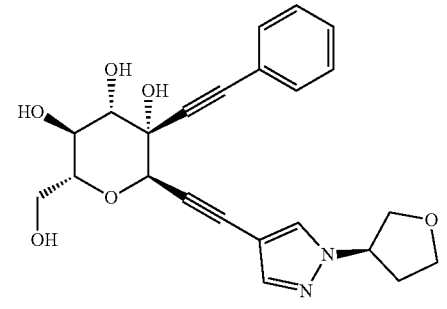

A51 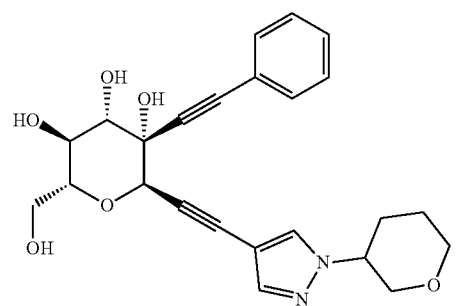
A52 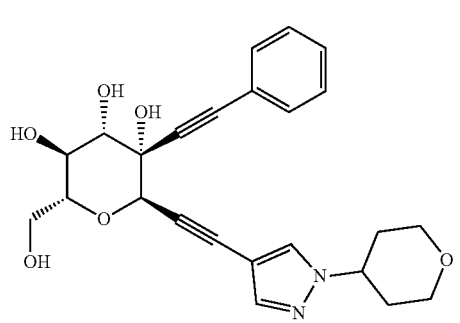
A53 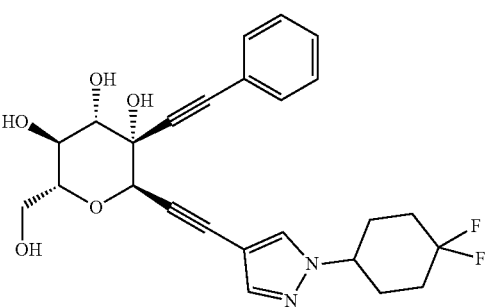
A54 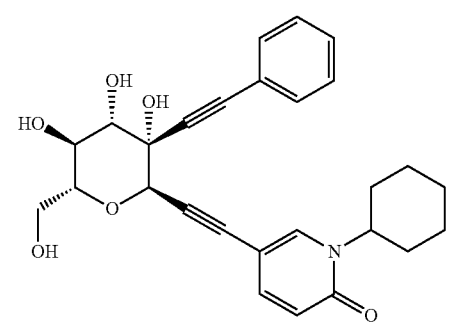
A55 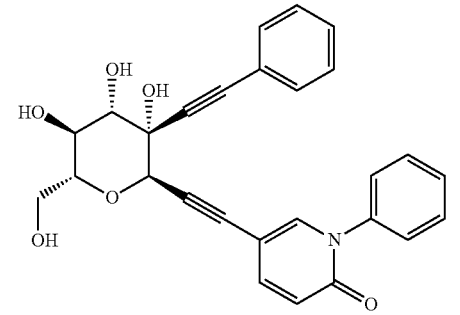
A56 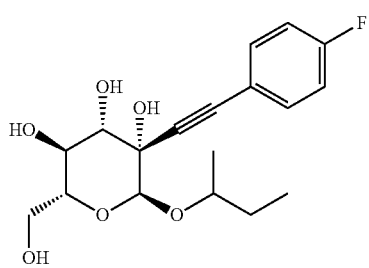
A57 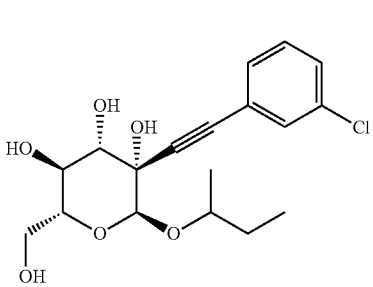
A58 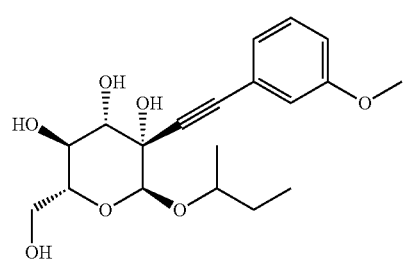
A59 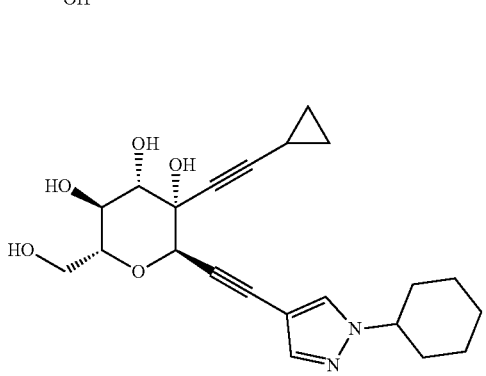
A60 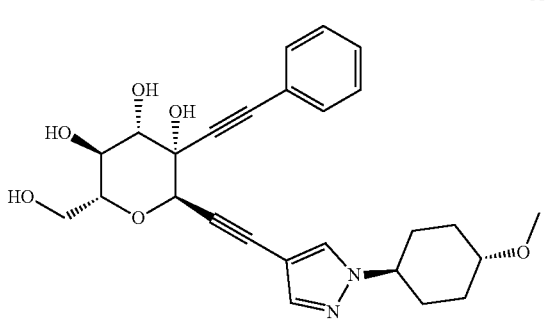

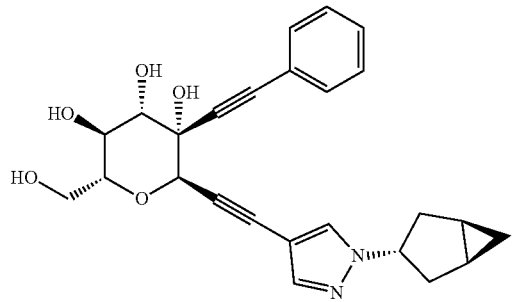
A61
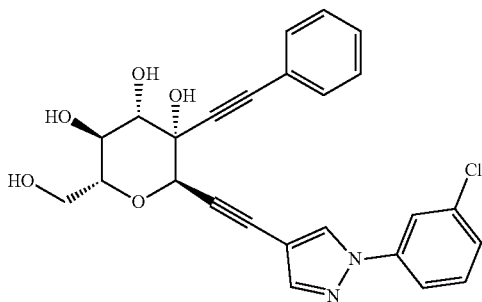
A66
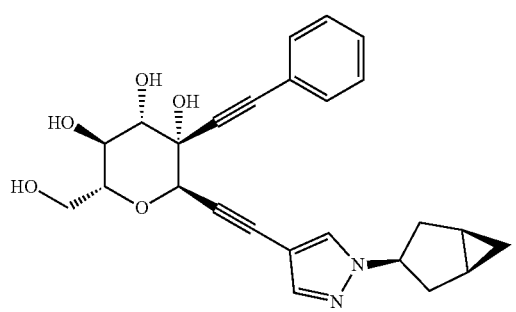
A62
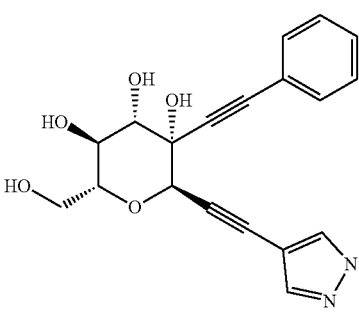
A67
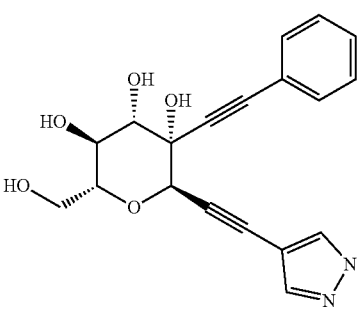
A63
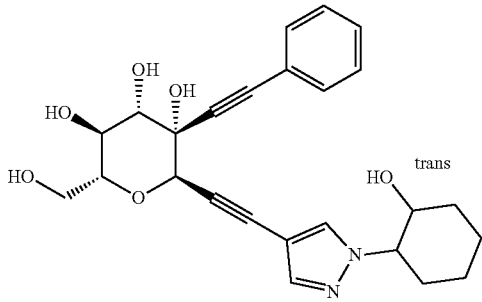
A68
A64
A69
A65
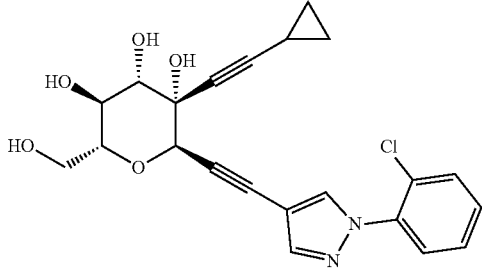
A70

25
-continued
A71
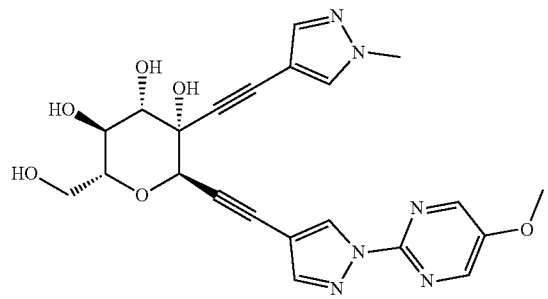
A72
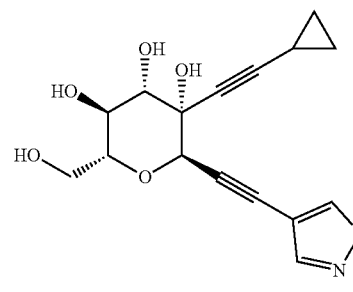
A73
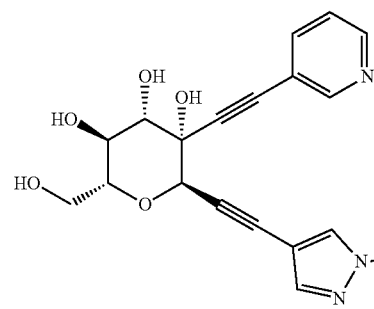
A74
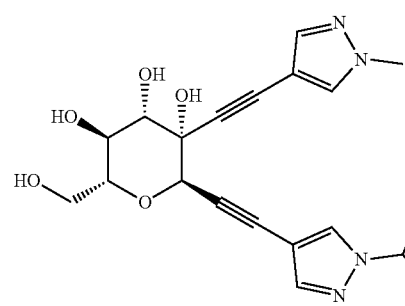
A75
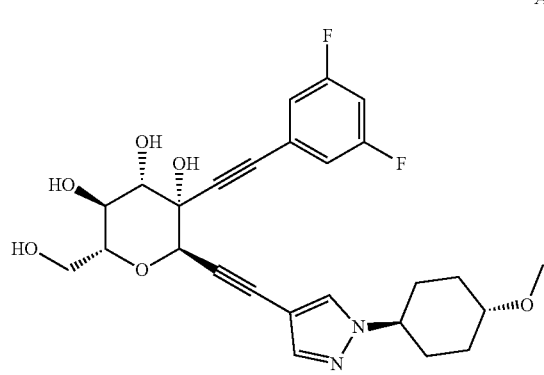
26
-continued
A76
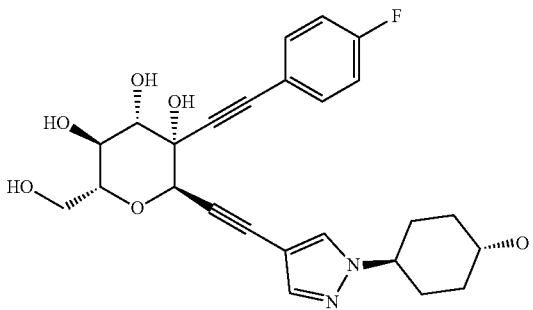
A77
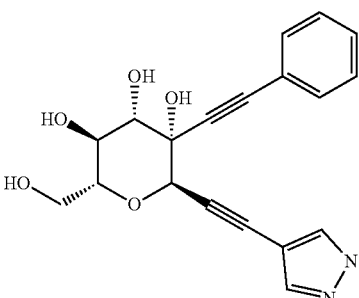
A78
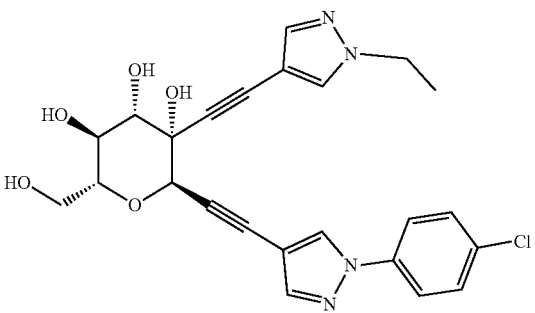
A79
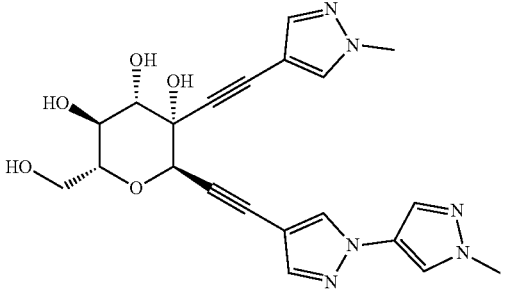
A80

A81
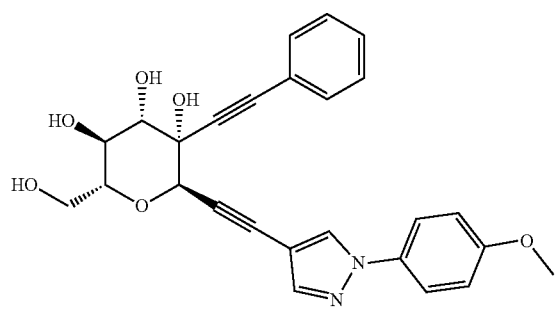
A82
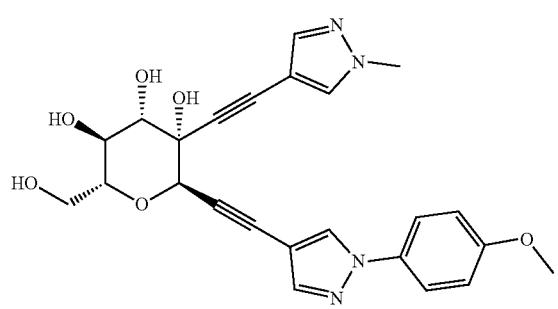
A83
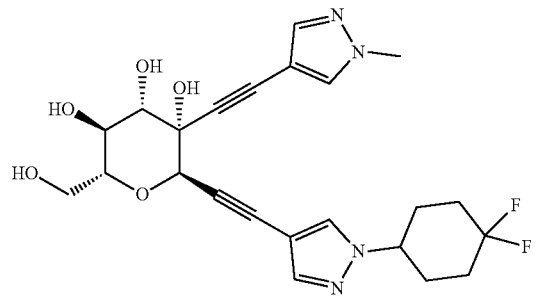
A84
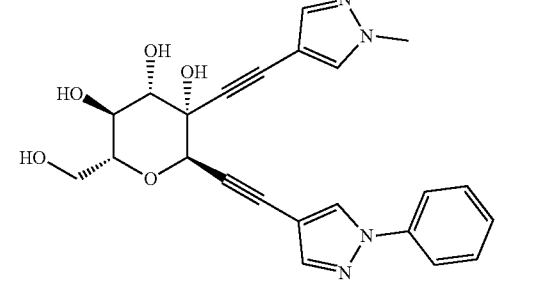
A85
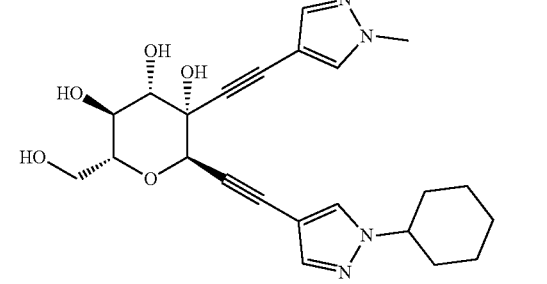
A86
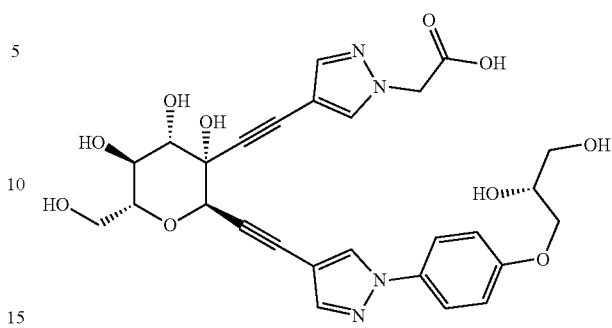
A87
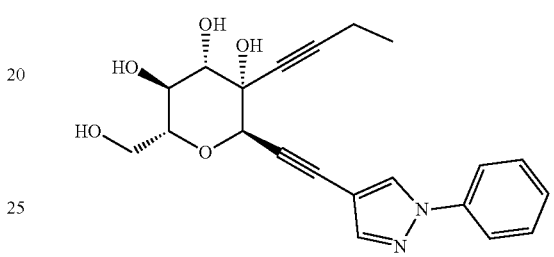
A88
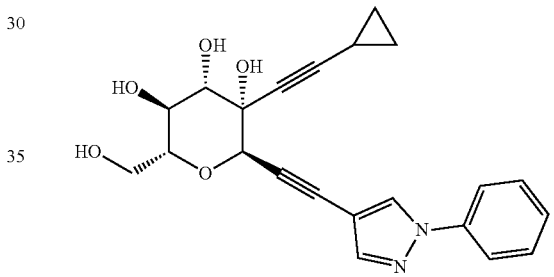
A89
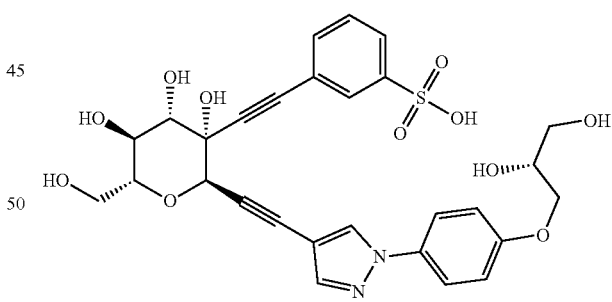
A90
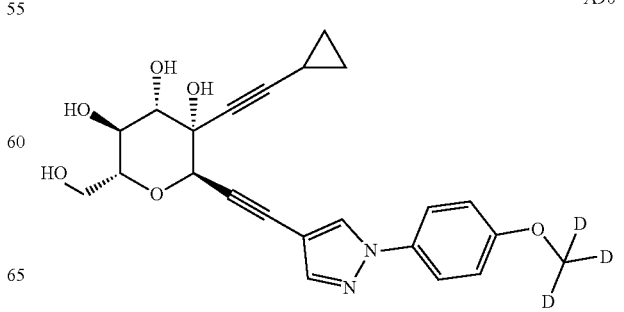

A91
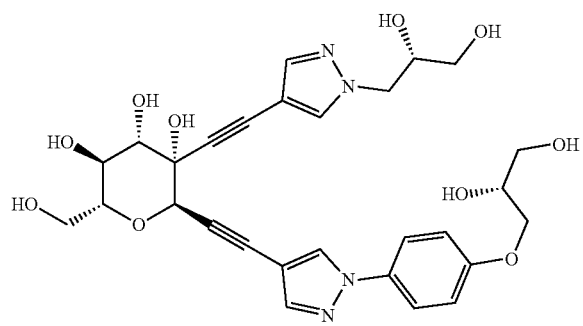
A92
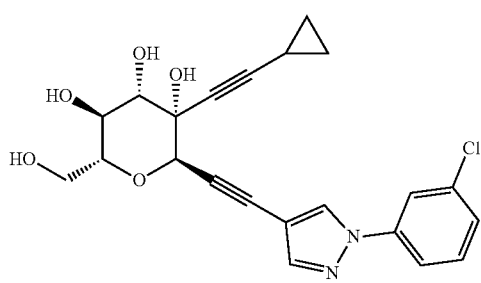
A93
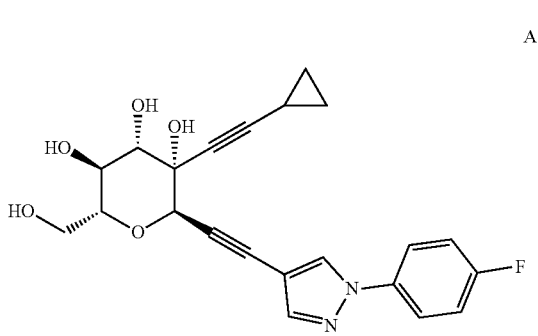
A94
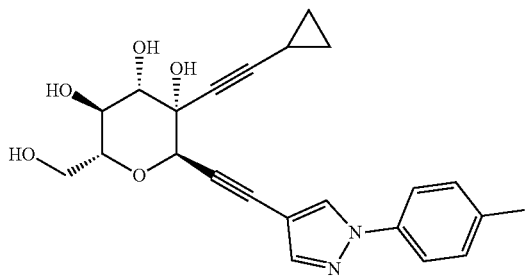
A95
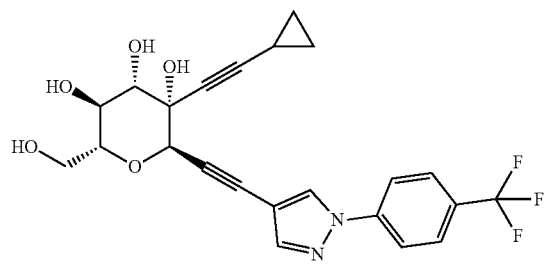
A96
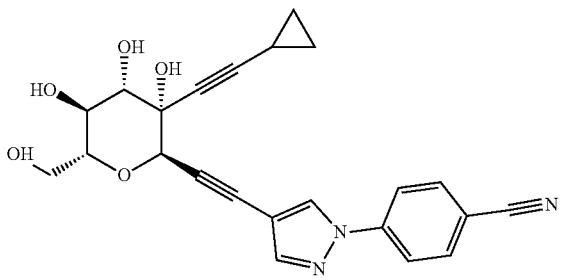
A97
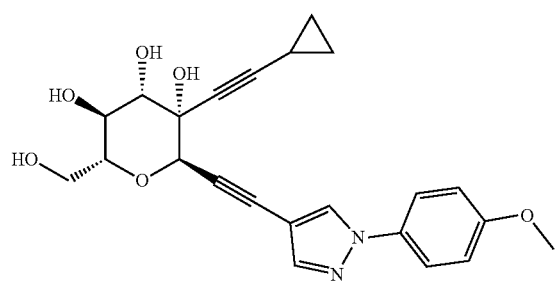
A98
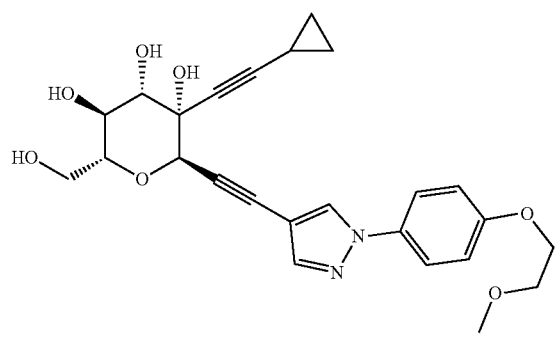
A99
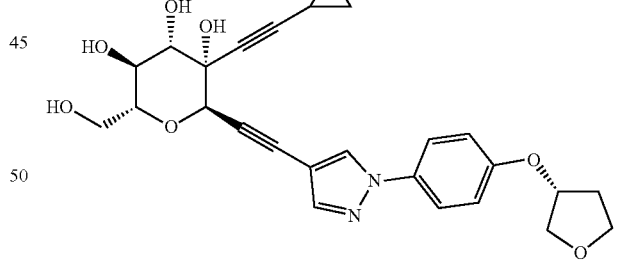
A100

-continued

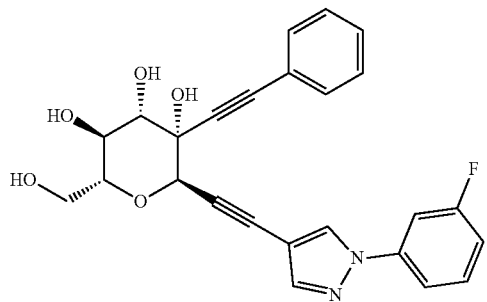

A101

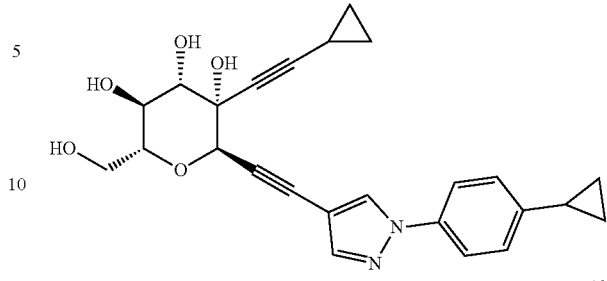

A105

A102

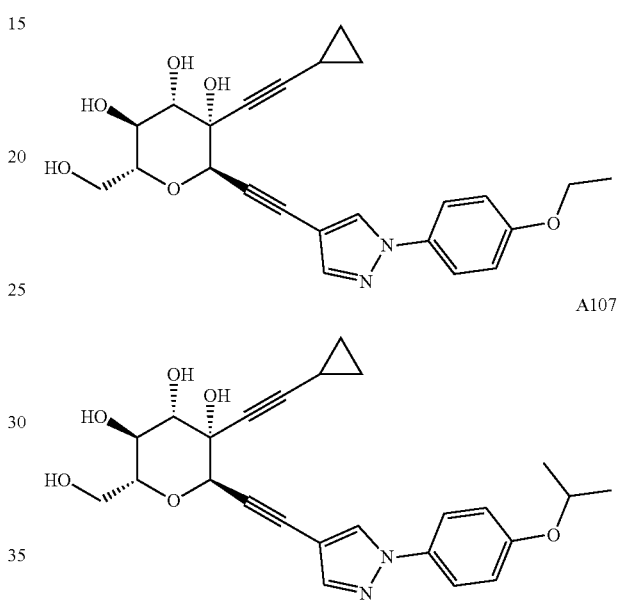

A106

A107

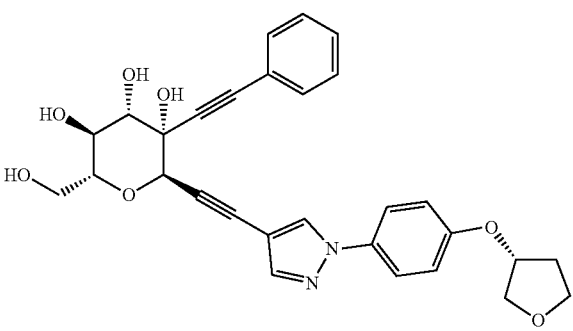

A103

The present disclosure also provides a pharmaceutical composition, which includes a composition formed by combining the above 2-alkynylmannose derivative or the pharmaceutically acceptable salt thereof with at least one pharmaceutically acceptable carrier or diluent.

The present disclosure also provides application of the above 2-alkynylmannose derivative and the pharmaceutically acceptable salt thereof, or the above pharmaceutical composition in preparation of a drug used for preventing or treating a disease or a disorder that is improved by inhibiting the function or activity of FimH.

Preferably, the disease or the disorder that is improved by inhibiting the function or activity of FimH is selected from UTIs, CD, and UC.

Definitions of the above groups are as follows.

Alkyl refers to straight or branched hydrocarbon alkyl groups composed of 1 to 10 carbon atoms.

Cycloalkyl refers to monocyclic, dicyclic, bridged, and spirocyclic hydrocarbon alkyl groups composed of 3 to 10 carbon atoms.

Alkoxy refers to —O—$C_{1-10}$ alkyl, —O—$C_{3-10}$ cycloalkyl, and —O—$C_{3-10}$ heterocyclic rings.

Alkenyl refers to straight or branched cyclic, dicyclic, and spirocyclic hydrocarbon compounds composed of 1 to 10 carbon atoms and containing at least one carbon-carbon double bond.

Alkynyl refers to straight or branched cyclic, dicyclic, and spirocyclic hydrocarbon compounds composed of 1 to 10 carbon atoms and containing at least one carbon-carbon triple bond.

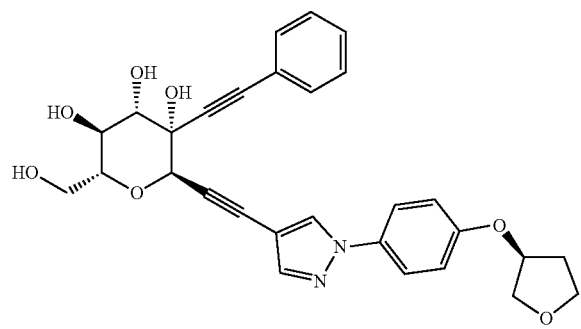

A104

Halogens refer to fluorine, chlorine, bromine, and iodine.

Heteroatoms refer to nitrogen, oxygen, and sulfur, and include various oxidation states of nitrogen, oxygen, and sulfur, quaternary ammonium salts of nitrogen, etc.

Aromatic rings refer to benzene rings, naphthalene rings, and substituted derivatives thereof, and also refer to derivative cyclic substituent groups of saturated rings and aromatic rings.

Heterocyclic rings refer to nonaromatic monocyclic rings, dicyclic rings, tricyclic rings, and spiros, which include at least one nitrogen, oxygen or sulfur, or cyclic substituent groups of various oxidation states of nitrogen, oxygen or sulfur.

Heteroaromatic rings refer to aromatic rings composed of 5 to 14 atoms, which include at least one nitrogen, oxygen or sulfur, or cyclic substituent groups of various oxidation states of nitrogen, oxygen or sulfur, such as pyridone compounds, and also refer to derivative cyclic substituent groups of saturated rings and heteroaromatic rings.

The present disclosure has the following outstanding effect.

The 2-alkynylmannose derivative of the present disclosure can well inhibit the function/activity of FimH proteins, and can be used for preventing or treating a disease or a disorder that is improved by inhibiting the function or activity of FimH proteins.

DETAILED DESCRIPTION OF THE EMBODIMENTS

Figure 1:
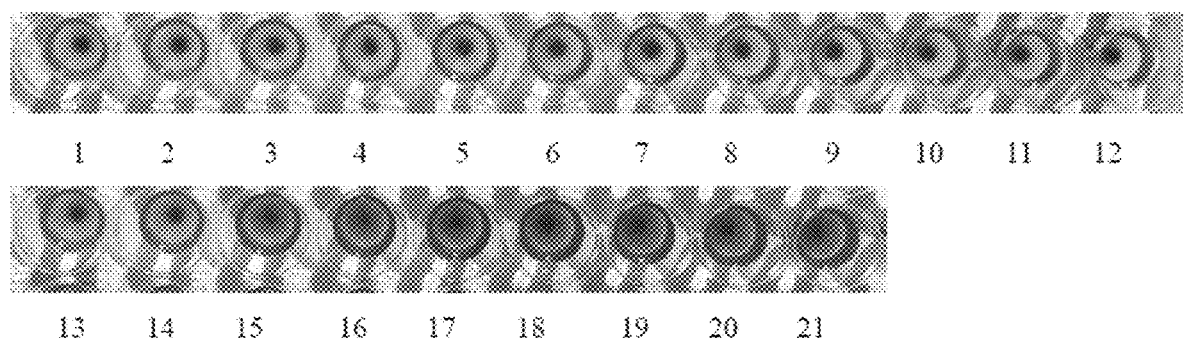
FIG. 1 is a diagram of an assay result of a compound A33.

In order to have a clearer understanding of the technical features, the objective, and the beneficial effects of the present disclosure, the technical solutions of the present disclosure will be described in detail below, but the scope of implementation of the present disclosure is not limited thereto. Experimental methods in the following examples, unless otherwise specified, are all conventional methods. Reagents and materials used in the following examples, unless otherwise specified, are all commercially available.

Solvents and drugs used in the following examples are all analytically pure or chemically pure. The solvents are all redistilled before use. Anhydrous solvents are all treated by standard methods or methods described in documents. Silica gels (100- to 200-mesh) for column chromatography and silica gels (GF254) for thin layer chromatography are purchased from Qingdao Ocean Chemical Plant and Yantain Chemical Plant. Unless otherwise specified, petroleum ether (60-90° C.)/ethyl acetate (v/v) is used as an eluent; an ethanol solution of iodine or phosphomolybdic acid is used as a color developing agent; and all extraction solvents are all dried with anhydrous $Na_2SO_4$ unless otherwise specified. $^1$HNMR is recorded by using a varian-400 nuclear magnetic resonance spectrometer and using TMS as an internal standard. LC-MS is recorded by using a 1100 high-performance liquid chromatography-ion trap mass spectrometer (LC-MSDTrap) purchased from Agilent (USA), a diode array detector (DAD) is used, detection wavelengths are 214 nm and 254 nm, and ion trap mass spectra (ESI source) are recorded. HPLC columns are AgelaDurashellC18 (4.6×50 mm, 3.5 μm); a mobile phase is 0.4% ammonium acetate aqueous solution: methanol (a ratio is changed from 5:95 to 95:5 within 5 min); and a flow rate is 1.8 mL/min.

Synthesis of an intermediate 1

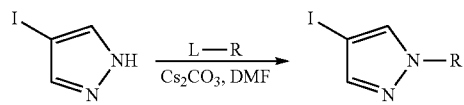

4-iodopyrazole (1.0 eq) was dissolved in anhydrous DMF, cesium carbonate (1.5 eq) and L-R (1.2 eq) were added, and the solution was heated to 70° C. and reacted overnight. After the solution was cooled to the room temperature, water was added to quench the reaction, the solution was extracted three times with ethyl ether, organic phases were combined, and the combined organic phase was washed three times with a saturated salt solution, dried with anhydrous $Na_2SO_4$, filtered, and concentrated. The residue was purified by column chromatography to obtain a product.

The following intermediates were synthesized from corresponding synthetic raw materials L-R by the synthesis method:

-continued

| Synthetic raw material L-R | Synthesized intermediate | Synthetic raw material L-R | Synthesized intermediate |
|---|---|---|---|

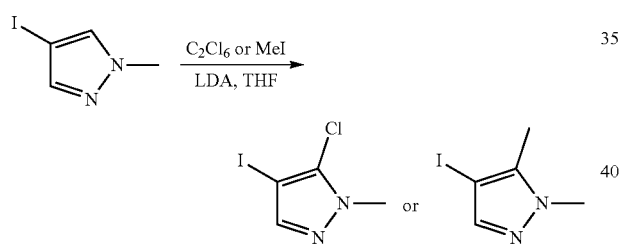

Synthesis of an intermediate 2

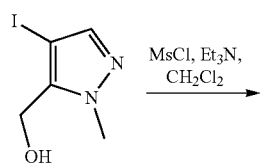

In the atmosphere of $N_2$, 4-iodo-1-methyl-1H-pyrazole (1.0 eq) was dissolved in anhydrous THF, the solution was cooled to −78° C., LDA (1.0 eq) was added, and the solution reacted for 1 h. Hexachloroethane or iodomethane (1.3 eq) was added, and the solution was slowly heated to the room temperature and reacted for 1 h. Saturated ammonium chloride was added to quench the reaction, the solution was extracted twice with ethyl acetate, organic phases were combined, the combined organic phase was washed with a saturated salt solution, dried with anhydrous $Na_2SO_4$, filtered, and concentrated. The residue was purified by column chromatography to obtain a product.

Synthesis of an intermediate 3

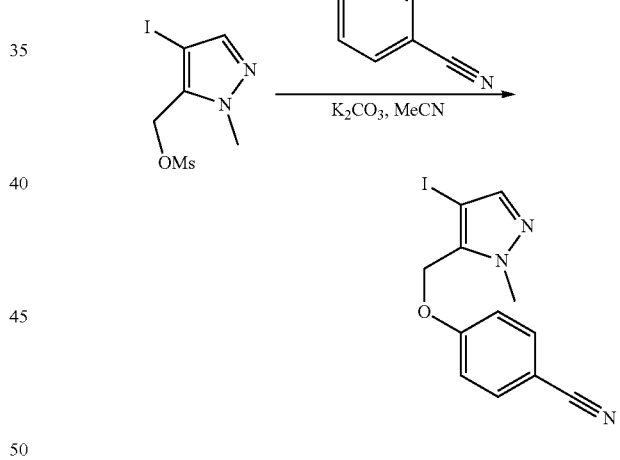

(4-iodo-1-methyl-1H-pyrazol-5-yl)methanol (714 mg, 3.0 mmol) was dissolved in dichloromethane (5 mL), at 0° C., triethylamine (606 mg, 6.0 mmol) and methanesulfonyl chloride (515 mg, 4.5 mmol) were added in sequence, and the solution was heated to the room temperature and reacted for 30 min. Saturated sodium bicarbonate was added, the solution was extracted three times with ethyl acetate, organic phases were combined, and the combined organic phase was washed with a saturated salt solution, dried with anhydrous $Na_2SO_4$, filtered, and concentrated to obtain a brown oily product (620 mg, 65%). The obtained oily product (620 mg, 2.0 mmol) was dissolved in anhydrous acetonitrile (6 mL), potassium carbonate (414 mg, 3.0 mmol) and p-cyanophenol (357 mg, 3.0 mmol) were added in sequence, and the solution was heated to 60° C. and reacted overnight. The solution was cooled to the room temperature, diluted with ethyl acetate, washed three times with saturated potassium carbonate, washed once with a saturated salt solution, dried with anhydrous Na$_2$SO$_4$, filtered, and concentrated. The residue was purified by column chromatography (petroleum ether: ethyl acetate=5:1 to 3:1) to obtain a white solid (450 mg, 66%).

Synthesis of an intermediate 4

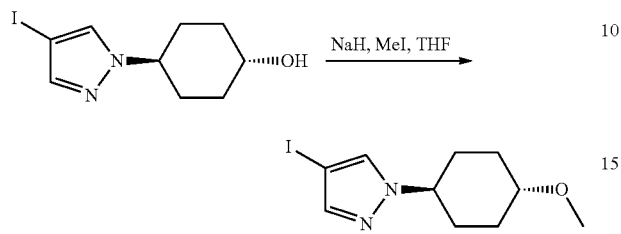

4-(4-iodo-1H-pyrazol-1-yl)cyclohexanol (600 mg, 2.1 mmol) was dissolved in THF (5 mL), nitrogen gas replacement was performed, at 0° C., sodium hydride (60%, 123 mg, E mmol) was added, and the solution reacted at the room temperature for 30 min. Iodomethane (586 mg, 4.1 mmol) was added, and the solution reacted at the room temperature for 1 h. Saturated sodium bicarbonate was added to quench the reaction, the solution was extracted three times with ethyl acetate, organic phases were combined, and the combined organic phase was washed with a saturated salt solution, dried with anhydrous Na$_2$SO$_4$, filtered, and concentrated to obtain a yellow solid (620 mg, 99%).

Synthesis of an intermediate 5

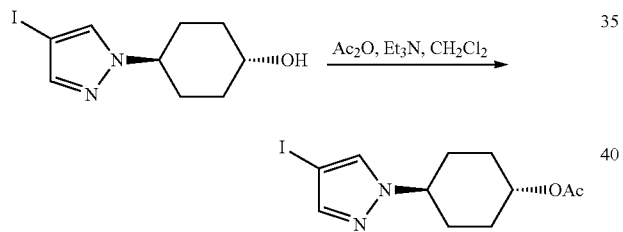

4-(4-iodo-1H-pyrazol-1-yl)cyclohexanol (600 mg, 2.1 mmol) was dissolved in dichloromethane (5 mL), at 0° C., triethylamine (0.9 mL, 6.2 mmol), DMAP (24 mg, 0.2 mmol), and acetic anhydride (314 mg, 3.1 mmol) were added in sequence, and the solution reacted at the room temperature overnight. Saturated sodium bicarbonate was added to quench the reaction, the solution was extracted three times with ethyl acetate, organic phases were combined, the combined organic phase was washed with a saturated salt solution, dried with anhydrous Na$_2$SO$_4$, filtered, and concentrated, and the residue was purified by column chromatography (petroleum ether: ethyl acetate=5:1 to 3:1) to obtain a yellow solid (645 mg, 92%).

Synthesis of an intermediate 6

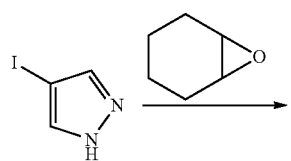

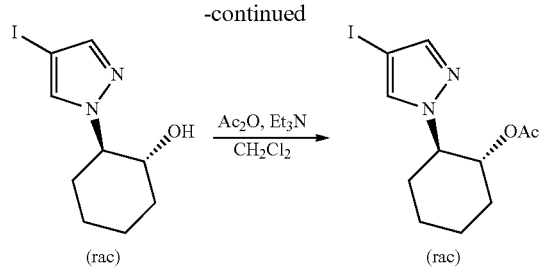

4-iodopyrazole (5.82 g, 30 mmol) and cyclohexene epoxide (2.94 g, 30 mmol) were heated to 160° C. and reacted for 5 h. The mixture was cooled to the room temperature, n-hexane (50 mL) was added, and the solution was heated to reflux for 10 min. The supernatant was poured out and cooled until a white solid was precipitated. The solid was collected by filtration and dried to obtain a white solid (5.3 g, 61%) The obtained white solid (1.5 g, 5.0 mmol) was dissolved in dichloromethane (15 mL), at 0° C., triethylamine (2.8 mL, 20 mmol), DMAP (61 mg, 0.5 mmol), and acetic anhydride (1.02 g, 10 mmol) were added in sequence, and the solution reacted at the room temperature overnight. Saturated sodium bicarbonate was added to quench the reaction, the solution was extracted three times with ethyl acetate, organic phases were combined, and the combined organic phase was washed with a saturated salt solution, dried with anhydrous Na$_2$SO$_4$, filtered, and concentrated. The residue was purified by column chromatography (petroleum ether: ethyl acetate=10:1 to 5:1) to obtain a colorless liquid (1.5 g, 90%).

Synthesis of an intermediate 7

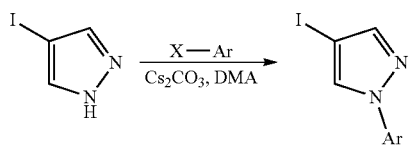

4-iodopyrazole (1.0 eq) and X—Ar (1.1 eq) were dissolved in DMA, cesium carbonate (1.1 eq) was added, and the solution was heated to 100° C. and reacted until the raw materials disappeared. The solution was cooled to the room temperature, water was added, and the solution was stirred for 30 min. The solution was filtered by suction, and the solid was washed twice with water and dried to obtain a product.

The following intermediates were synthesized from corresponding synthetic raw materials X—Ar by the synthesis method:

| Reaction raw material X-Ar | Reaction product | Reaction raw material X-Ar | Reaction product |
|---|---|---|---|
| 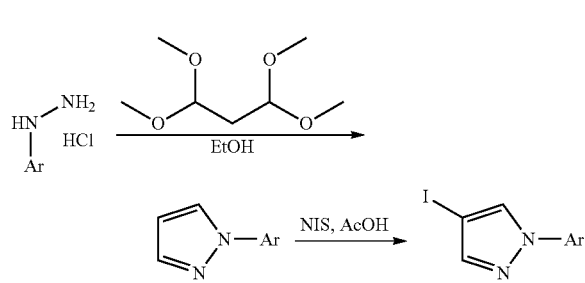 | | | |

Synthesis of an intermediate 8

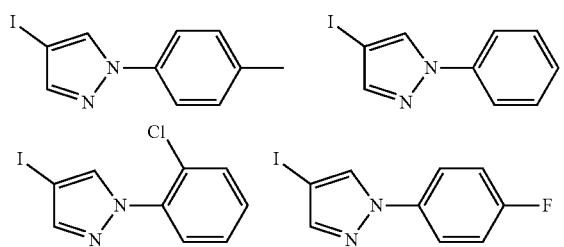

A hydrazine hydrochloride (1.0 eq) and 1,1,3,3-tetramethoxypropane (1.0 eq) were dissolved in 95% ethanol, and the solution was heated to 70° C. and reacted for 8 h. The solution was cooled to the room temperature and concentrated under reduced pressure, saturated sodium bicarbonate was added, and the mixture was stirred for 30 min. The mixture was extracted three times with ethyl acetate, organic phases were combined, and the combined organic phase was washed with a saturated salt solution, dried with anhydrous $Na_2SO_4$, filtered, and concentrated. The residue was dissolved in acetic acid, NIS (1.2 eq) was added, and the solution reacted at the room temperature for 1-2 h. Saturated sodium bisulfite was added to quench the reaction, water was added, and the solution was stirred for 30 min. The solution was filtered by suction, and the solid was washed twice with water and dried to obtain a product.

The following intermediates were synthesized from corresponding hydrazine hydrochlorides by the synthesis method:

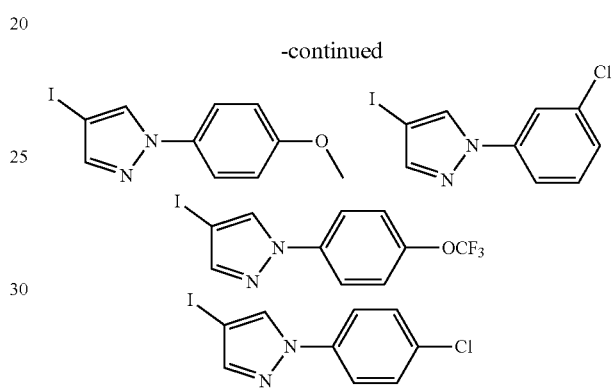

-continued

Synthesis of an intermediate 9

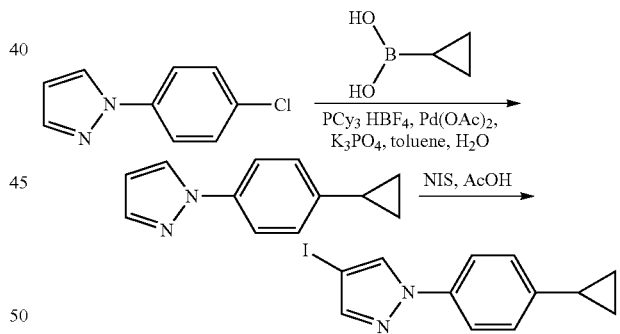

1-(4-chlorophenyl)-1H-pyrazole (178 mg, 1.0 mmol) was dissolved in a mixture of toluene (4 mL) and water (0.2 mL), cyclopropylboronic acid (129 mg, 1.5 mmol), palladium acetate (11 mg, 0.05 mmol), tricyclohexylphosphorus fluoroborate (37 mg, 0.1 mmol), and potassium phosphate (954 mg, 4.5 mmol) were added in sequence, nitrogen gas replacement was performed, and the solution was heated to 100° C. and reacted for 18 h. The solution was cooled to the room temperature, water was added, the solution was extracted three times with petroleum ether, organic phases were combined, and the combined organic phase was washed with a saturated salt solution, dried with anhydrous $Na_2SO_4$, filtered, and concentrated to obtain a yellow solid (180 mg, a crude product). The obtained solid was dissolved in glacial acetic acid (1 mL), NIS (286 mg, 1.3 mmol) was added, and the solution reacted at the room temperature for 1 h. A saturated sodium bisulfite aqueous solution was added to quench the reaction, water was added, and the solution was stirred for 30 min. The solution was filtered by suction, and the filter cake was washed twice with water and dried to obtain a yellow solid (300 mg, 97%).

Synthesis of an intermediate 10

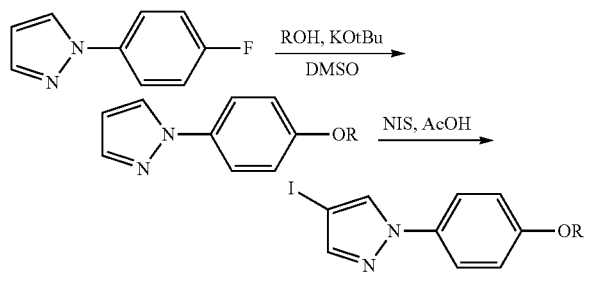

In the atmosphere of nitrogen gas, 1-(4-fluorophenyl)-1H-pyrazole (1.0 eq) and corresponding alcohol (1.15 eq) were dissolved in DMSO, potassium tert-butoxide (1.1 eq) was added, and the solution was heated to 100° C. and reacted for 3 h. The solution was cooled to the room temperature, water was added to quench the reaction, the solution was stirred for 30 min until a solid was precipitated, and the solid was collected by suction filtration and dried. The obtained solid was dissolved in glacial acetic acid, NIS (1.25 eq) was added, and the solution reacted at the room temperature for 1 h. A saturated sodium bisulfite aqueous solution was added to quench the reaction, water was added, and the solution was stirred for 30 min. The solution was filtered by suction, and the filter cake was washed twice with water and dried to obtain a product.

The following intermediates were synthesized from corresponding starting materials ROH by the synthesis method:

Synthesis of an intermediate 11

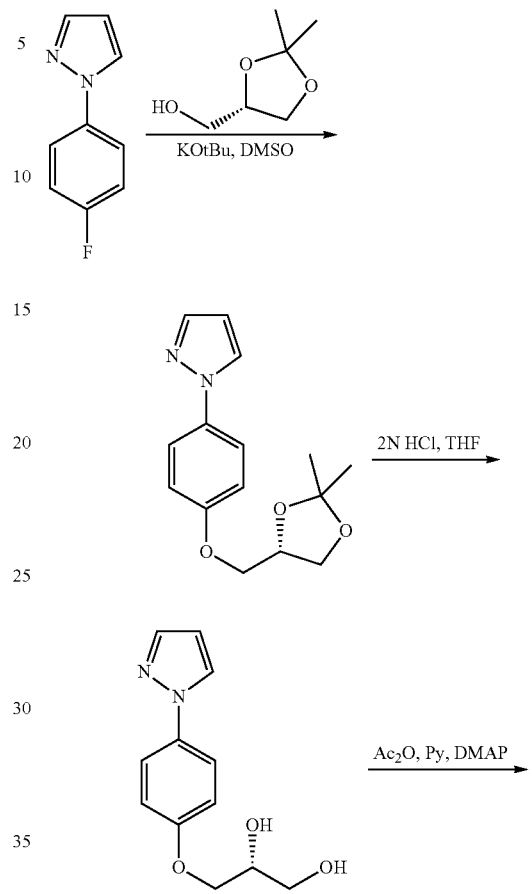

| Reaction raw material ROH | Reaction product | Reaction raw material ROH | Reaction product |
|---|---|---|---|
| EtOH | | | |
| | | | |
| | | | |
| CD₃OD | | | |

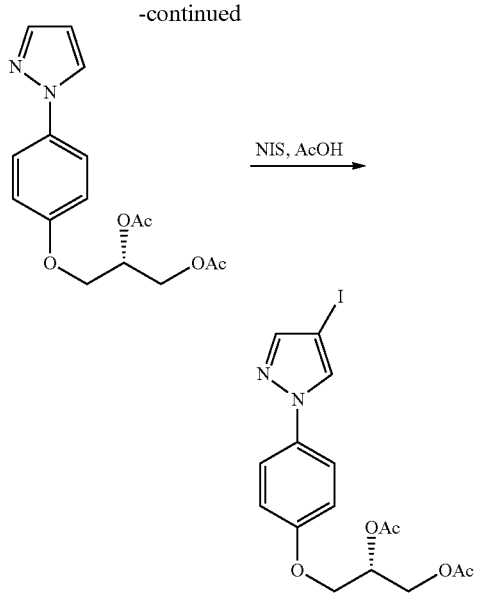

In the atmosphere of nitrogen gas, 1-(4-fluorophenyl)-1H-pyrazole (2.43 g, 15 mmol) and (S)-fork glycerinol (2.28 g, 17.3 mmol) were dissolved in DMSO (8 mL), potassium tert-butoxide (2.0 g, 16.5 mmol) was added, and the solution was heated to 90° C. and reacted for 3 h. The solution was cooled to the room temperature, water was added to quench to the reaction, the solution was stirred for 30 min until a solid was precipitated, and the solid was collected by suction filtration and dried to obtain a yellow solid (3.85 g, 94%). The obtained solid was dissolved in THF (10 mL), 2 N HCl (5 mL) was added, and the solution was stirred at the room temperature overnight. The solution was diluted with ethyl acetate, washed with saturated sodium bicarbonate, washed with saturated sodium chloride, dried with anhydrous sodium sulfate, and concentrated under reduced pressure to obtain a white solid (2.67 g, 76%). The obtained solid (2.67 g, 11.4 mmol) was dissolved in pyridine (20 mL), DMAP (139 mg, 1.14 mmol) and acetic anhydride (2.9 g, 28.5 mmol) were added, and the solution was stirred at the room temperature overnight. A saturated salt solution was added to quench the reaction, and the solution was stirred for 15 min. The solution was extracted three times with ethyl acetate, organic phases were combined, and the combined organic phase was washed twice with 1 N HCl, washed with saturated sodium bicarbonate, washed with a saturated salt solution, dried with anhydrous sodium sulfate, and concentrated under reduced pressure. The obtained yellow liquid was dissolved in acetic acid (5 mL), NIS (2.7 g, 11.8 mmol) was added, and the solution reacted at the room temperature for 1 h. A saturated sodium bisulfite aqueous solution was added to quench the reaction, water was added, and the solution was stirred for 30 min. The solution was filtered by suction, and the filter cake was washed twice with water and dried to obtain a yellow solid (4.83 g, 96%).

Synthesis of an intermediate 12

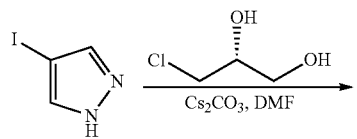

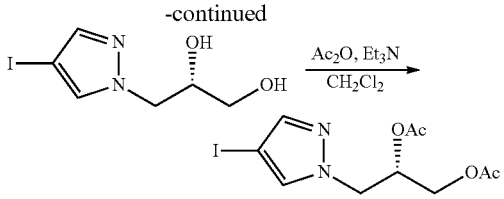

4-iodopyrazole (3.88 g, 20 mmol) and (R)-3-chloro-1,2-propanediol (3.32 g, 30 mmol) were dissolved in acetonitrile (60 mL), potassium carbonate (5.52 g, 40 mmol) and potassium iodide (1.66 g, 10 mmol) were added, and the solution was heated to reflux overnight. The solution was cooled to the room temperature, ethyl acetate was added, the solution was filtered by suction, and the filter cake was washed twice with ethyl acetate. Filtrates were combined, and the combined filtrate was dried with anhydrous sodium sulfate and concentrated under reduced pressure. The obtained oily product was dissolved in dichloromethane (50 mL), triethylamine (10 g, 100 mmol) and DMAP (224 mg, 2.0 mmol) were added, and the solution was cooled to 0° C. Acetic anhydride (8.2 g, 80 mmol) was added, and the solution was heated to the room temperature and stirred overnight. Saturated sodium bicarbonate was added to quench the reaction, and the solution was extracted three times with ethyl acetate. Organic phases were combined, the combined organic phase was washed with a saturated salt solution, dried with anhydrous $Na_2SO_4$, filtered, and concentrated, and the residue was purified by column chromatography (petroleum ether: ethyl acetate=5:1 to 3:1) to obtain a pale-yellow oily product (6.6 g, 94%).

Synthesis of an intermediate 13

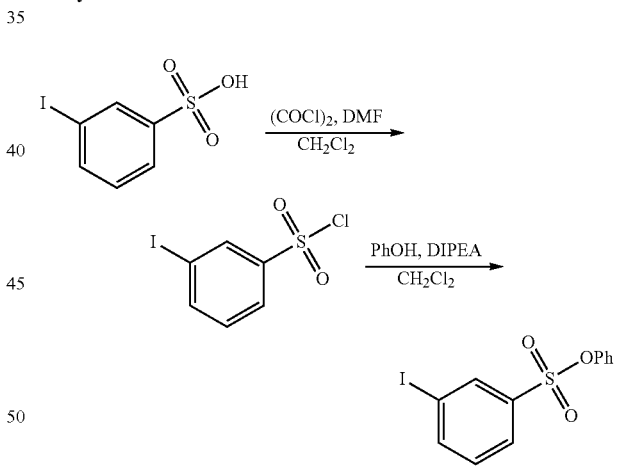

3-iodobenzenesulfonic acid (2.84 mg, 10 mmol) was dissolved in dichloromethane (20 mL), and DMF (15 mg, 0.2 mmol) was added. Nitrogen gas replacement was performed, the solution was heated to 45° C., oxalyl chloride (1.59 g, 12.5 mmol) was added dropwise, and the solution reacted at 45° C. for 2.5 h. The solution was cooled to 0° C., water (9 mL) was added to quench the reaction, and the solution was extracted with ethyl acetate. The organic phase was washed with water until a pH value was equal to 4-5, washed three times with saturated potassium carbonate, dried with anhydrous sodium sulfate, and concentrated under reduced pressure to obtain a yellow liquid (2.6 g, 86%). A dichloromethane solution (20 mL) of DIPEA (2.2 mL, 12 mmol) and phenol (846 mg, 9.0 mmol) was prestirred for 10 min, a dichloromethane solution (30 mL) of the above yellow liquid (2.6 g) was added, and the solution was stirred at the room temperature until the raw materials disappeared. 1 N HCl was added to quench the reaction, the solution was extracted three times with ethyl acetate, organic phases were combined, and the combined organic phase was washed with a saturated salt solution, dried with anhydrous Na$_2$SO$_4$, filtered, and concentrated to obtain a yellow oily product (3.1 g, 100%).

Synthesis of an intermediate 14

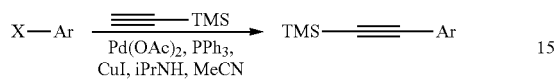

Halogenated aromatic hydrocarbon (1.0 eq) was dissolved in MeCN, palladium acetate (0.025 eq), CuI (0.04 eq), PPh$_3$ (0.1 eq), and diisopropylamine (1.5 eq) were added, nitrogen gas replacement was performed, at the room temperature, trimethylsilylacetylene (1.4 eq) was added, and the solution was heated to 80° C. and reacted until the raw materials disappeared. The solution was cooled to the room temperature, diluted with ethyl acetate, and filtered by suction, and the filter cake was washed once with ethyl acetate. Filtrates were combined, and the combined filtrate was concentrated under reduced pressure. The residue was purified by column chromatography to obtain a product.

The following intermediates were synthesized from corresponding synthetic raw materials I—Ar by the synthesis method:

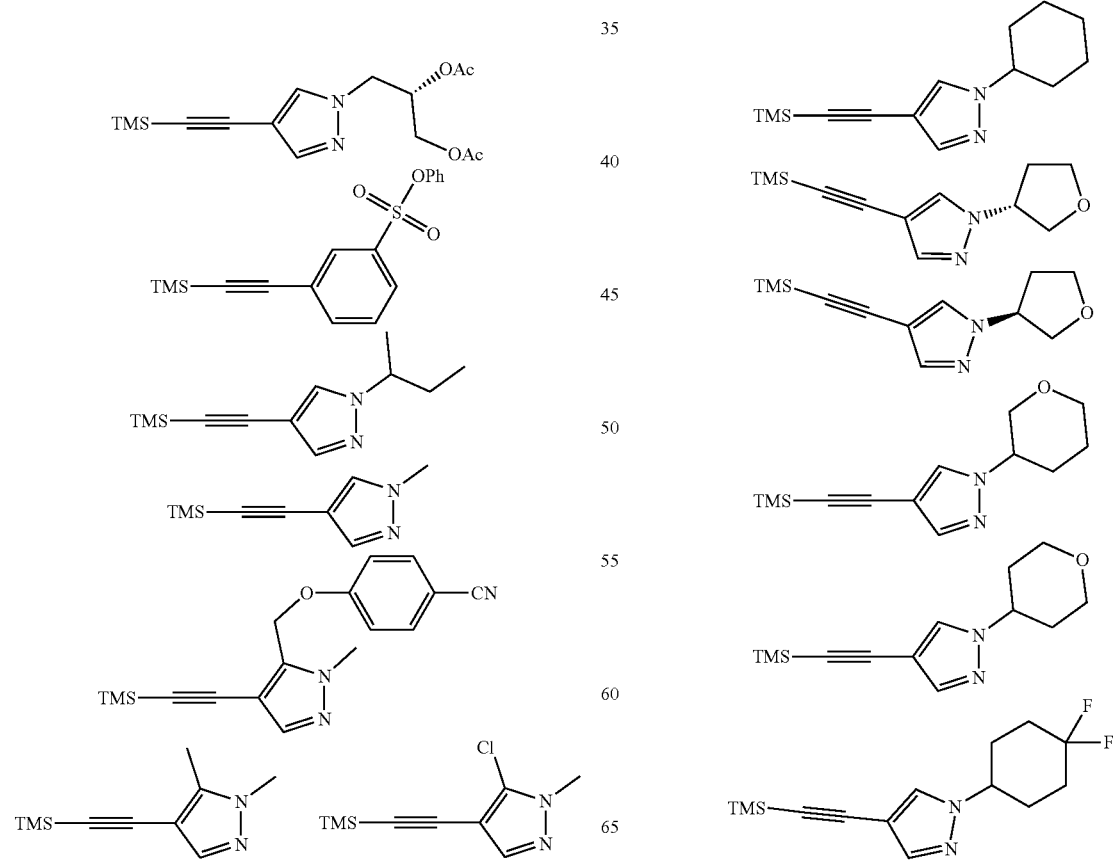

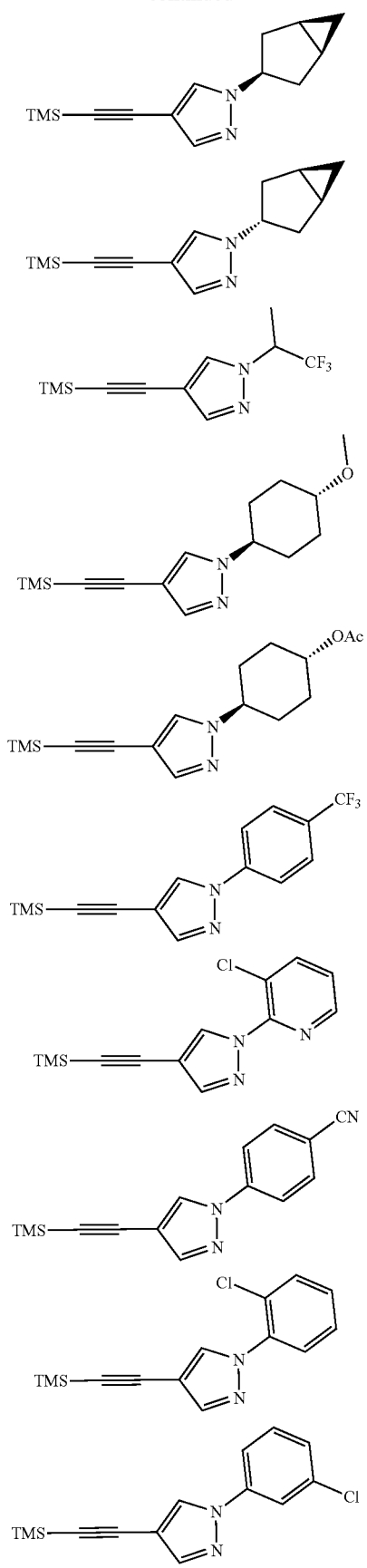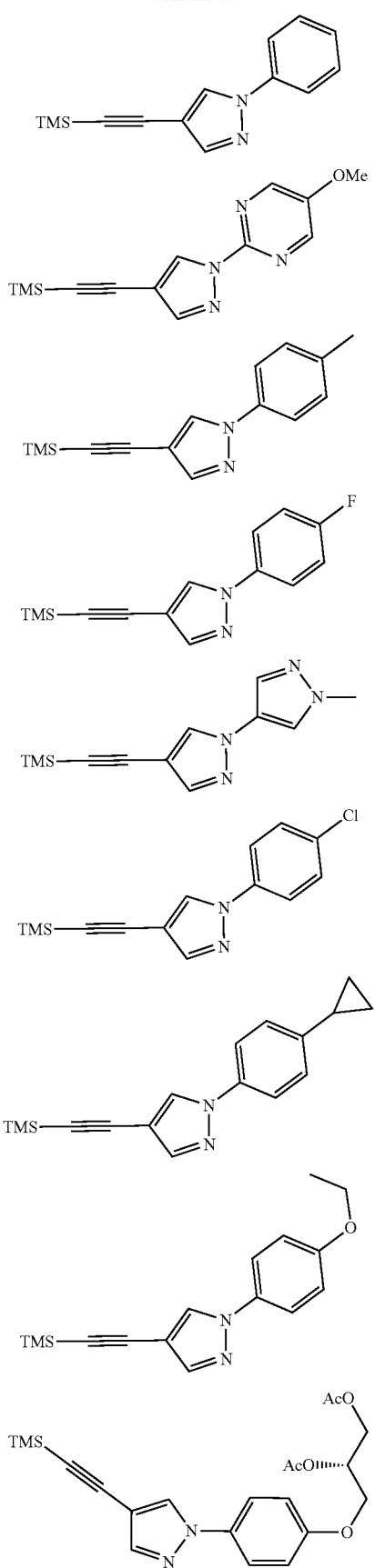

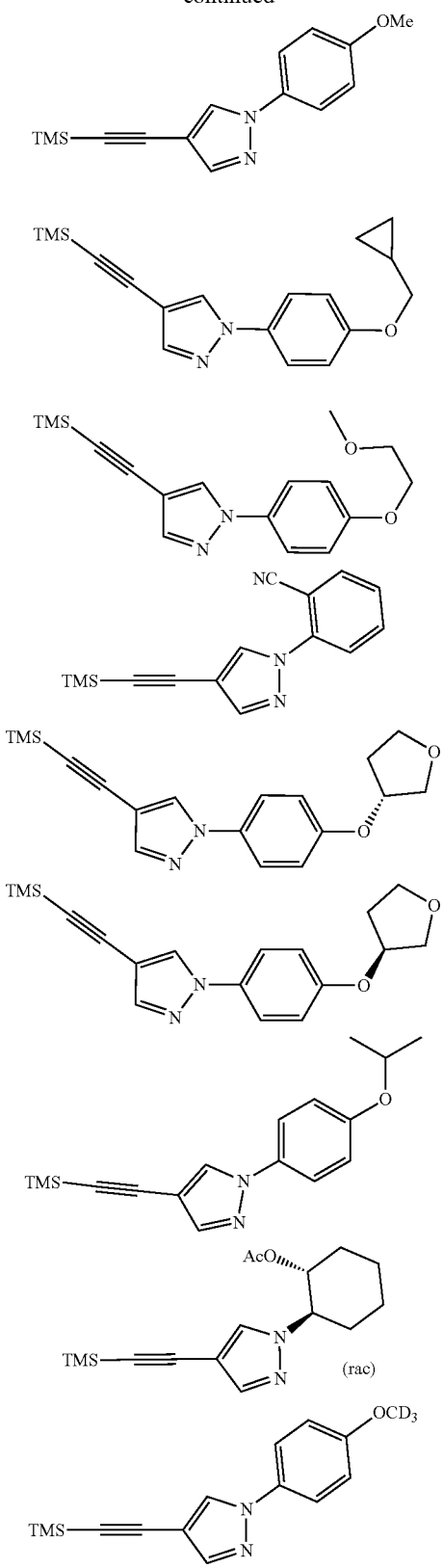
The following intermediates were synthesized from corresponding synthetic raw materials Br—Ar by the synthesis method:
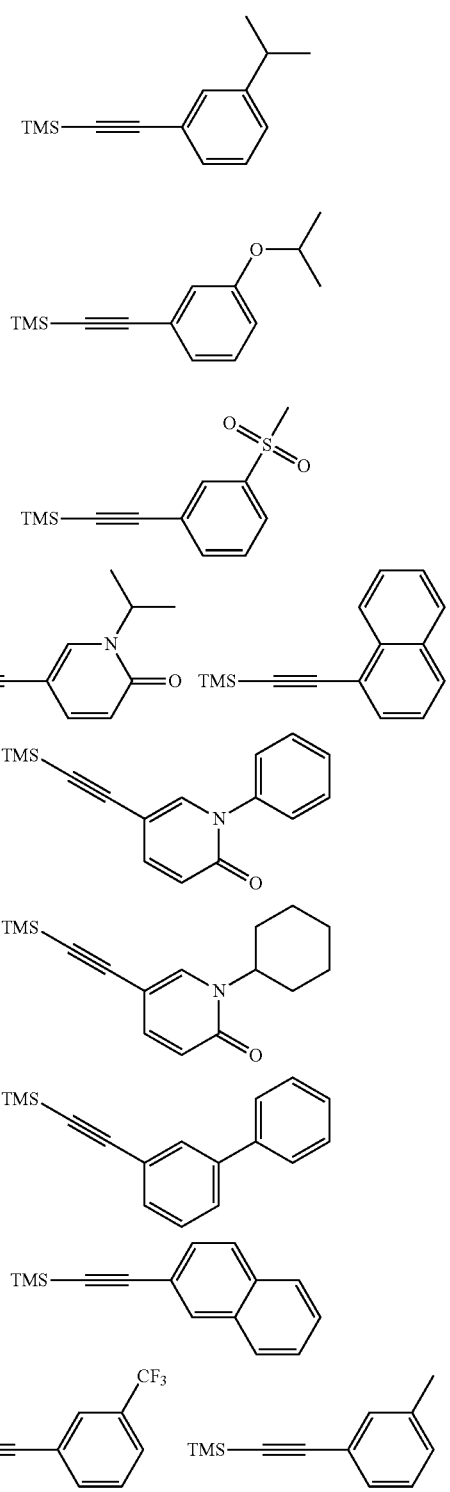
Synthesis of an intermediate 15
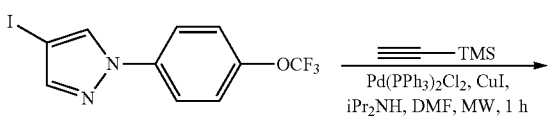

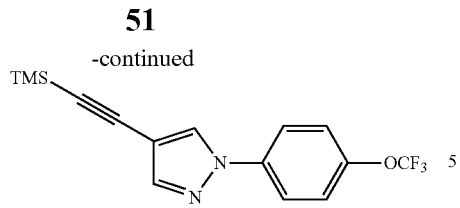

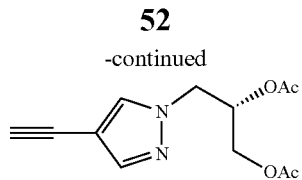

4-iodo-1-(4-trifluoromethoxyphenyl)-1H-pyrazole (390 mg, 1.1 mmol), trimethylsilylacetylene (220 mg, 2.2 mmol), bis(triphenylphosphine)palladium dichloride (39 mg, 0.055 mmol), CuI (11 mg, 0.055 mmol), and diisopropylamine (0.46 mL, 3.3 mmol) were dispersed in DMF (5 mL), in the atmosphere of nitrogen gas, the solution was microwave-heated to 120° C. and reacted for 1 h. The solution was cooled to the room temperature, diluted with ethyl ether, washed twice with water, washed with a saturated salt solution, dried with anhydrous Na$_2$SO$_4$, filtered, and concentrated. The residue was purified by column chromatography (petroleum ether: ethyl acetate=20:1 to 10:1) to obtain a brown solid (290 mg, 81%).

Synthesis of an intermediate 16

Trimethylsilyl alkyne (1.0 eq) and acetic acid (1.2 eq) were dissolved in THF (5 mL), nitrogen gas replacement was performed, at 0° C., a 1 M THF solution (1.2 eq) of TBAF was added, and the solution was heated to the room temperature and reacted for 2 h. Saturated sodium bicarbonate was added to quench the reaction, the solution was extracted three times with ethyl acetate, organic phases were combined, and the combined organic phase was washed three times with a saturated salt solution, dried with anhydrous Na$_2$SO$_4$, filtered, and concentrated to obtain a product.

The following intermediates were synthesized from corresponding synthetic raw materials by the synthesis method:

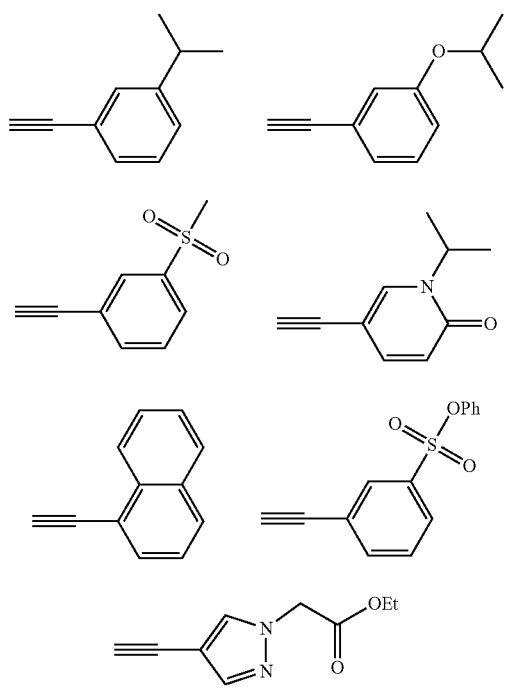

Synthesis of an intermediate 17

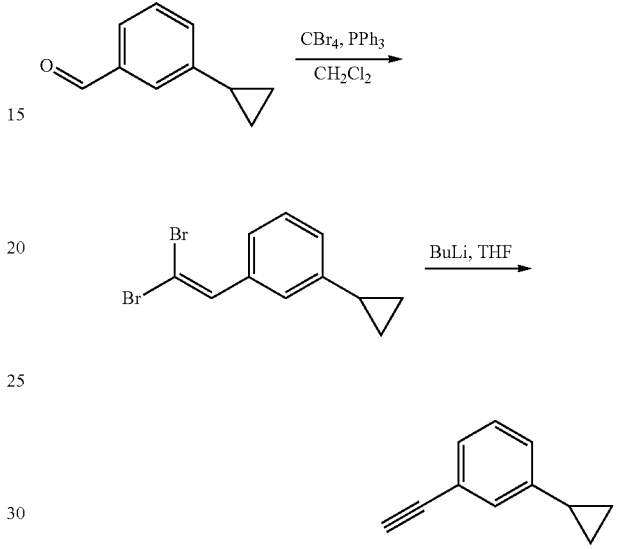

CBr$_4$ (3.87 g, 11.6 mmol) was dissolved in dichloromethane (50 mL), at 0° C., PPh$_3$ (6.0 g, 23.2 mmol) was added, a dichloromethane solution (50 mL) of 3-cyclopropylbenzaldehyde (1.7 g, 11.6 mmol) was added, and the solution was heated to the room temperature and reacted for 2 h. Methanol was added to quench the reaction, and the solution was concentrated under reduced pressure. The residue was diluted with petroleum ether, washed with a saturated salt solution, dried with anhydrous Na$_2$SO$_4$, filtered, and concentrated, and the residue was purified by column chromatography (petroleum ether) to obtain a yellow oily product (2.8 g, 80%). The obtained oily product (1.4 g, 4.6 mmol) was dissolved in anhydrous THF (5 mL), nitrogen gas replacement was performed, at −78° C., butyl lithium (a 2.5 M THF solution, 4 mL, 10 mmol) was added dropwise, and the solution reacted for 30 min. Saturated ammonium chloride was added to quench the reaction, and the solution was extracted three times with ethyl ether. Organic phases were combined, and the combined organic phase was washed once with a saturated salt solution, dried with anhydrous Na$_2$SO$_4$, filtered, and concentrated. The residue was purified by column chromatography (petroleum ether: ethyl acetate=1:0 to 20:1) to obtain a pale-yellow oily product (620 mg, 95%).

Example 1

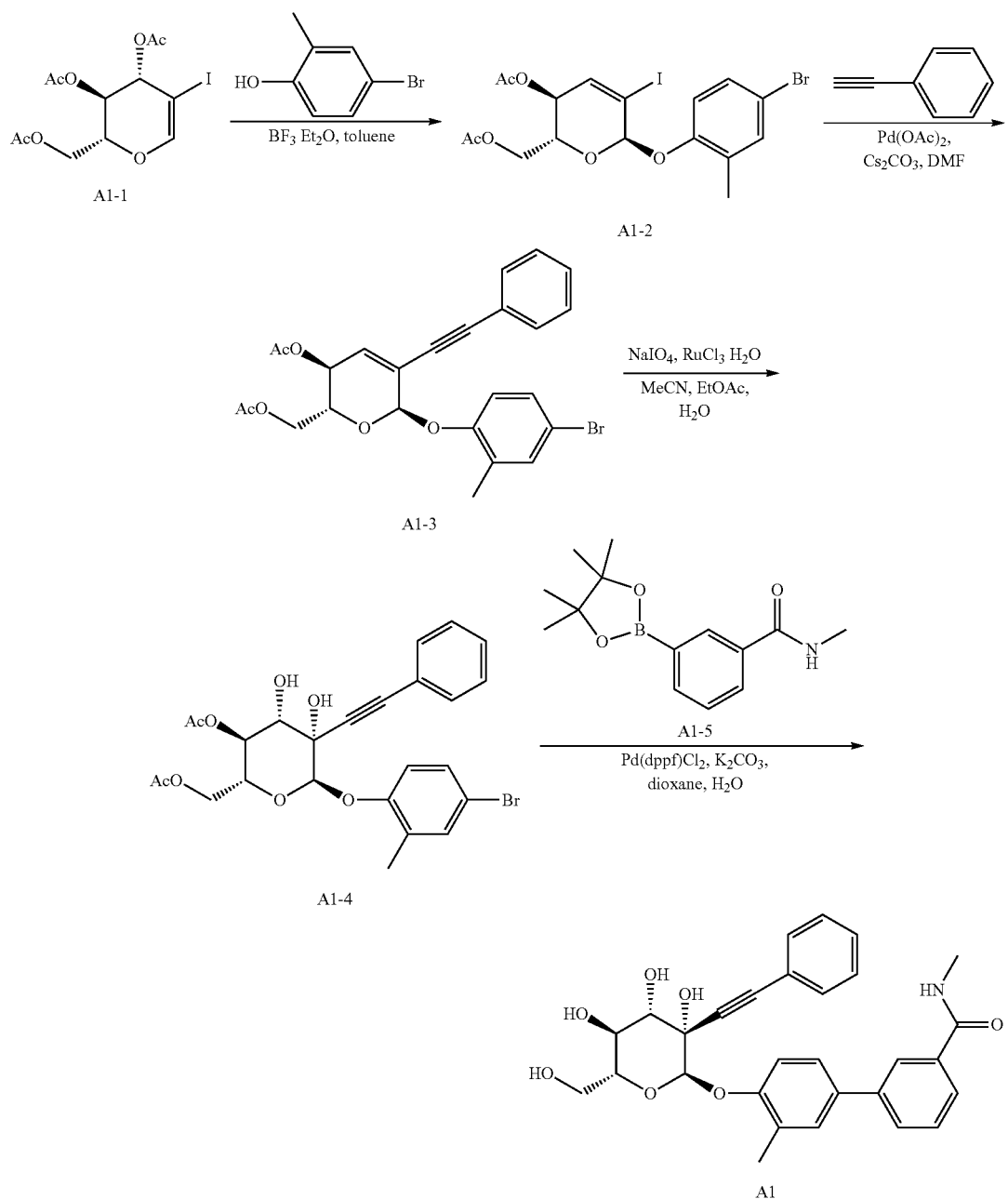

1) Synthesis of an intermediate A1-2

A compound A1-1 (2.8 g, 7 mmol, synthesized with reference to S. Dharuman et al., Org. Lett. 2014, 16, 1172-1175) and 4-bromo-2-methylphenol (1.3 g, 7 mmol) were dissolved in anhydrous toluene (6 mL), boron trifluoride ethyl ether (200 mg, 1.4 mmol) was added, and the solution was stirred at the room temperature overnight. Saturated $NaHCO_3$ was added to quench the reaction, and the solution was extracted three times with ethyl acetate. Organic phases were combined, and the combined organic phase was washed with a saturated salt solution, dried with anhydrous $Na_2SO_4$, filtered, and concentrated, and the residue was purified by column chromatography (petroleum ether: ethyl acetate=10:1 to 5:1) to obtain a yellow oily product (1.2 g, 34%).

2) Synthesis of an intermediate A1-3

A1-2 (280 mg, 0.56 mmol), phenylacetylene (88 mg, 0.84 mmol), palladium acetate (4.8 mg, 0.02 mmol), and cesium carbonate (272 mg, 0.84 mmol) were dispersed in anhydrous DMF (1.5 mL), nitrogen gas replacement was performed, and the solution was stirred at the room temperature overnight. Saturated $NaHCO_3$ was added to quench the reaction, the solution was extracted three times with ethyl acetate, organic phases were combined, and the combined organic phase was washed three times with a saturated salt solution. The organic phase was dried with anhydrous sodium sulfate, filtered, and concentrated. The residue was purified by column chromatography (petroleum ether: ethyl acetate=10: 1) to obtain a yellow oily product (200 mg, 72%).

3) Synthesis of an intermediate A1-4

A1-3 (200 mg, 0.42 mmol) was dissolved in a mixture of ethyl acetate/acetonitrile (4 mL/4 mL), at 0° C., a solution that was newly prepared by dissolving NaIO$_4$ (135 mg, 0.63 mmol) and ruthenium trichloride monohydrate (7 mg, 0.034 mmol) in water (1.4 mL) was added, and the solution reacted at 0° C. for 5 min. Saturated sodium thiosulfate was added to quench the reaction, and the solution was extracted three times with ethyl acetate. Organic phases were combined, and the combined organic phase was washed with a saturated salt solution, dried with anhydrous sodium sulfate, filtered, and concentrated. The residue was purified by column chromatography (petroleum ether: ethyl acetate=3:1 to 1:1) to obtain a yellow oily product (110 mg, 52%).

4) Synthesis of a product A1

The intermediate A1-4 (110 mg, 0.22 mmol) and A1-5 (86 mg, 0.33 mmol, synthesized with reference to WO2017156508) were dissolved in a mixture of dioxane/water (1 mL/0.2 mL), potassium carbonate (91 mg, 0.66 mmol) and Pd(dppf)Cl$_2$ (7 mg, 0.01 mmol) were added, nitrogen gas replacement was performed, and the solution was heated to 100° C. and stirred overnight. The solution was cooled to the room temperature, a 2 N NaOH aqueous solution (0.5 mL) was added, and the solution was stirred at the room temperature for 2 h. The solution was purified by using a reversed phase rapid preparative chromatograph (Biotage) to obtain a yellow solid (20 mg, 18%).

Example 2

Referring to the synthesis method in Example 1, compounds A2 and A3 were synthesized by replacing phenyl acetylene with cyclopropyl acetylene or 4-ethynyl-N-methylpyrazole at step 2).

Example 3

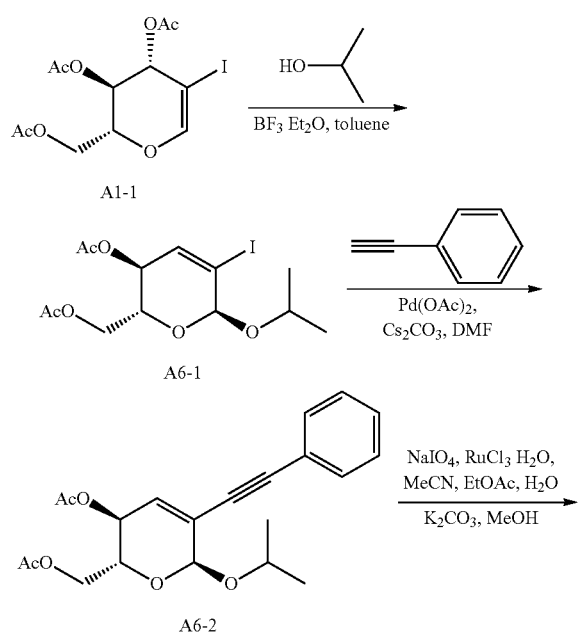

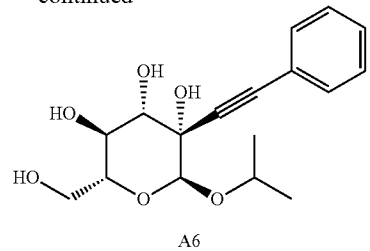

A6

1) Synthesis of an intermediate A6-1

The compound A1-1 (199 mg, 0.5 mmol) and isopropanol (36 mg, 0.6 mmol) were dissolved in anhydrous toluene (2 mL). At −15° C., boron trifluoride ethyl ether (142 mg, 1.0 mmol) was added dropwise, and the solution was heated to the room temperature and reacted for 2 h. Saturated NaHCO$_3$ was added to quench the reaction, and the solution was extracted three times with ethyl acetate. Organic phases were combined, the combined organic phase was washed with a saturated salt solution, dried with anhydrous Na$_2$SO$_4$, filtered, and concentrated, and the residue was purified by column chromatography (petroleum ether: ethyl acetate=10:1 to 5:1) to obtain a yellow oily product (90 mg, 45%).

2) Synthesis of an intermediate A6-2

A6-1 (90 mg, 0.23 mmol), phenylacetylene (28 mg, 0.28 mmol), palladium acetate (2.7 mg, 0.012 mmol), and cesium carbonate (113 mg, 0.35 mmol) were dispersed in anhydrous DMF (1 mL), nitrogen gas replacement was performed, and the solution was stirred at the room temperature for 1 h. Saturated NaHCO$_3$ was added to quench the reaction, the solution was extracted three times with ethyl acetate, organic phases were combined, and the combined organic phase was washed three times with a saturated salt solution. The organic phase was dried with anhydrous sodium sulfate, filtered, and concentrated. The residue was purified by column chromatography (petroleum ether: ethyl acetate=10:1) to obtain a yellow oily product (80 mg, 94%).

3) Synthesis of a product A6

A6-2 (80 mg, 0.22 mmol) was dissolved in a mixture of ethyl acetate/acetonitrile (2 mL/2 mL), at 0° C., a solution that was newly prepared by dissolving NaIO$_4$ (71 mg, 0.33 mmol) and ruthenium chloride monohydrate (3.5 mg, 0.017 mmol) in water (0.7 mL) was added, and the solution reacted at 0° C. for 5 min. Saturated sodium thiosulfate was added to quench the reaction, and the solution was extracted three times with ethyl acetate. Organic phases were combined, and the combined organic phase was washed with a saturated salt solution and concentrated under reduced pressure. The residue was dissolved in methanol (1 mL), potassium carbonate (10 mg, 0.07 mmol) was added, and the solution was stirred at the room temperature overnight. The solution was concentrated under reduced pressure, and the residue was purified by column chromatography (petroleum ether: ethyl acetate=1:1 to ethyl acetate to ethyl acetate: methanol=10:1) to obtain a pale-yellow solid (20 mg, 26%).

Example 4

Referring to the synthesis method in Example 3, compounds A4, A5, A7 to A9, A11 to A13, and A56 to A58 were synthesized by replacing isopropanol with corresponding alcohol or phenol at step 1) and replacing phenylacetylene with corresponding alkyne at step 2).

Example 5

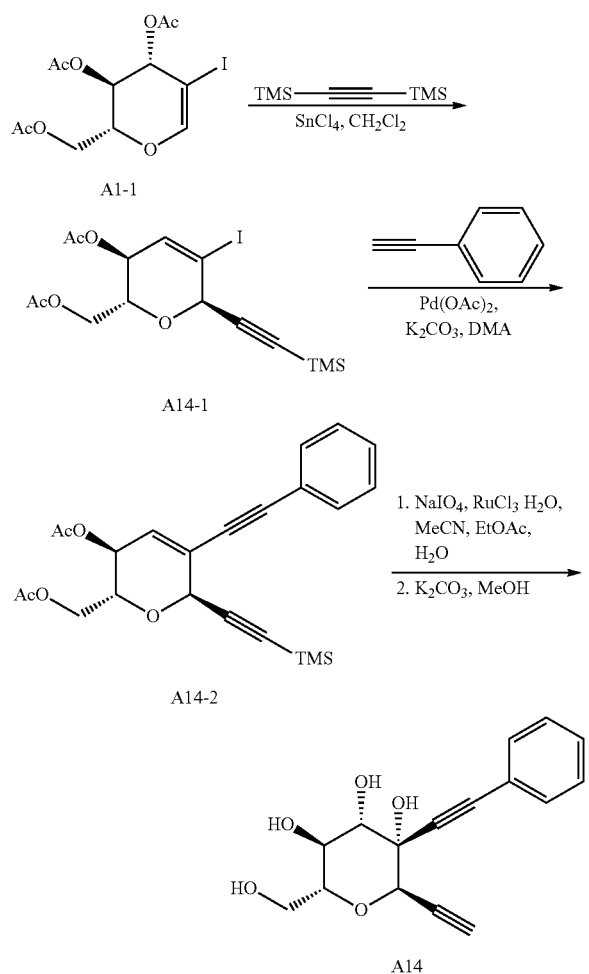

1) Synthesis of an intermediate A14-1

The compound A1-1 (199 mg, 0.5 mmol) and bis(trimethylsilyl)acetylene (0.24 mL, 1.0 mmol) were dissolved in anhydrous dichloromethane (4 mL), at −25° C., tin tetrachloride (0.09 mL, 0.75 mmol) was added, and the solution was heated to −15° C. and reacted for 2 h. Saturated NaHCO$_3$ (6 mL) and water (6 mL) were added to quench the reaction, and the solution was heated to the room temperature and stirred for 1 h. The solution was extracted three times with ethyl acetate, organic phases were combined, and the combined organic phase was washed with a saturated salt solution, dried with anhydrous Na$_2$SO$_4$, filtered, and concentrated. The residue was purified by column chromatography (petroleum ether: ethyl acetate=10:1 to 5:1) to obtain a pale-red oily product (200 mg, 90%).

2) Synthesis of an intermediate A14-2

A14-1 (1.0 g, 2.3 mmol), phenylacetylene (286 mg, 2.8 mmol), palladium acetate (27 mg, 0.12 mmol), and potassium carbonate (483 mg, 3.5 mmol) were dispersed in anhydrous DMA (10 mL), nitrogen gas replacement was performed, and the solution was stirred at the room temperature overnight. Saturated NaHCO$_3$ was added to quench the reaction, the solution was extracted three times with ethyl acetate, organic phases were combined, and the combined organic phase was washed three times with a saturated salt solution. The organic phase was dried with anhydrous sodium sulfate, filtered, and concentrated. The residue was purified by column chromatography (petroleum ether: ethyl acetate=10:1) to obtain a yellow oily product (566 mg, 60%).

3) Synthesis of a product A14

A14-2 (150 mg, 0.36 mmol) was dissolved in a mixture of ethyl acetate/acetonitrile (3 mL/3 mL), at 0° C., a solution that was newly prepared by dissolving NaIO$_4$ (117 mg, 0.55 mmol) and ruthenium trichloride monohydrate (6 mg, 0.03 mmol) in water (1.2 mL) was added, and the solution reacted at 0° C. for 5 min. Saturated sodium thiosulfate was added to quench the reaction, and the solution was extracted three times with ethyl acetate. Organic phases were combined, and the combined organic phase was washed with a saturated salt solution and concentrated under reduced pressure. The residue was dissolved in methanol (1 mL), potassium carbonate (10 mg, 0.07 mmol) was added, and the solution was stirred at the room temperature overnight. The solution was concentrated under reduced pressure, and the residue was purified by column chromatography (petroleum ether: ethyl acetate=1:1 to ethyl acetate to ethyl acetate: methanol=10:1) to obtain a pale-yellow solid (12 mg, 12%).

Example 6

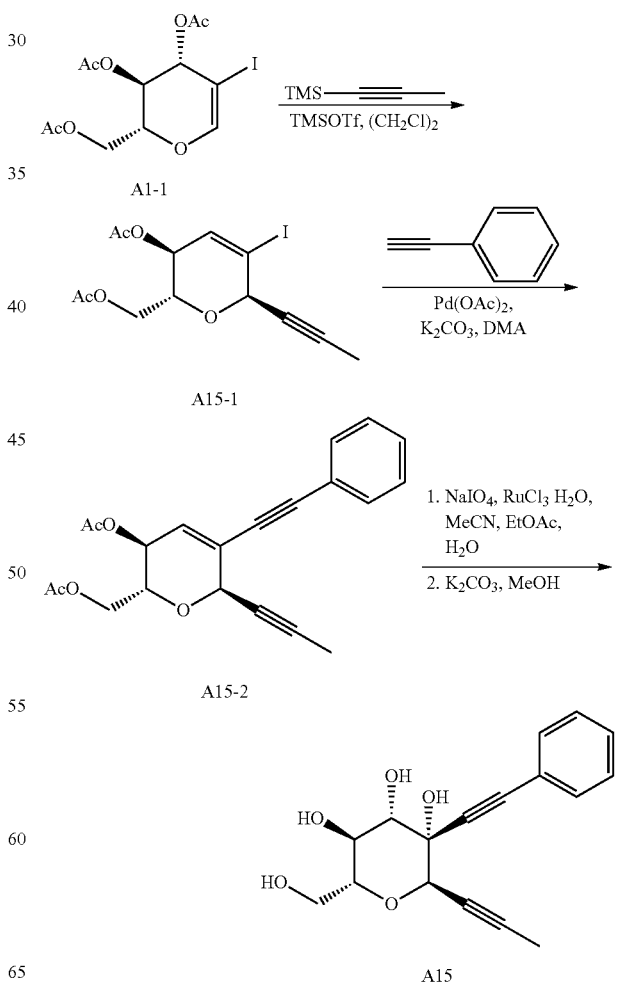

1) Synthesis of an intermediate A15-1

The compound A1-1 (300 mg, 0.75 mmol) and trimethylsilylpropyne (101 mg, 0.9 mmol) were dissolved in anhydrous 1,2-dichloroethane (5 mL), at the room temperature, a solution that was prepared by dissolving TMSOTf (100 mg, 0.45 mmol) in 1,2-dichloroethane (1 mL) was added dropwise, and the solution was heated to 80° C. and reacted for 30 min. The solution was cooled to the room temperature, triethylamine was added to quench the reaction, and the solution was concentrated under reduced pressure. The residue was purified by column chromatography (petroleum ether: ethyl acetate=10:1 to 7:1) to obtain a yellow oily product (260 mg, 92%).

2) Synthesis of an intermediate A15-2

A1-1 (260 mg, 0.69 mmol), phenylacetylene (85 mg, 0.83 mmol), palladium acetate (8 mg, 0.035 mmol), and potassium carbonate (143 mg, 1.04 mmol) were dispersed in anhydrous DMF (2 mL), nitrogen gas replacement was performed, and the solution was stirred at the room temperature overnight. Saturated NaHCO$_3$ was added to quench the reaction, the solution was extracted three times with ethyl ether, organic phases were combined, and the combined organic phase was washed three times with a saturated salt solution. The organic phase was dried with anhydrous sodium sulfate, filtered, and concentrated. The residue was purified by column chromatography (petroleum ether: ethyl acetate=10:1) to obtain a yellow oily product (210 mg, 86%).

3) Synthesis of a product A15

A15-2 (210 mg, 0.60 mmol) was dissolved in a mixture of ethyl acetate/acetonitrile (5 mL/5 mL), at 0° C., a solution that was newly prepared by dissolving NaIO$_4$ (193 mg, 0.9 mmol) and ruthenium trichloride monohydrate (10 mg, 0.047 mmol) in water (2 mL) was added, and the solution reacted at 0° C. for 5 min. Saturated sodium thiosulfate was added to quench the reaction, and the solution was extracted three times with ethyl acetate. Organic phases were combined, and the combined organic phase was washed with a saturated salt solution and concentrated under reduced pressure. The residue was dissolved in methanol (1 mL), potassium carbonate (10 mg, 0.07 mmol) was added, and the solution was stirred at the room temperature overnight. The solution was concentrated under reduced pressure, and the residue was purified by column chromatography (petroleum ether: ethyl acetate=1:1 to ethyl acetate to ethyl acetate: methanol=10:1) to obtain a pale-yellow solid (30 mg, 17%).

Example 7

Referring to the synthesis method in Example 6, compounds A10, A17 to A55, A59 to A68, A70 to A75, A78 to A85, A87, A88, A90, and A92 to A107 were synthesized by replacing trimethylsilylpropyne with corresponding trimethylsilyl alkyne at step 1) and replacing phenylacetylene with corresponding alkyne at step 2).

Example 8

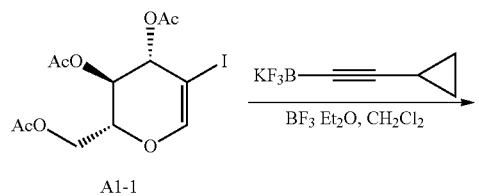

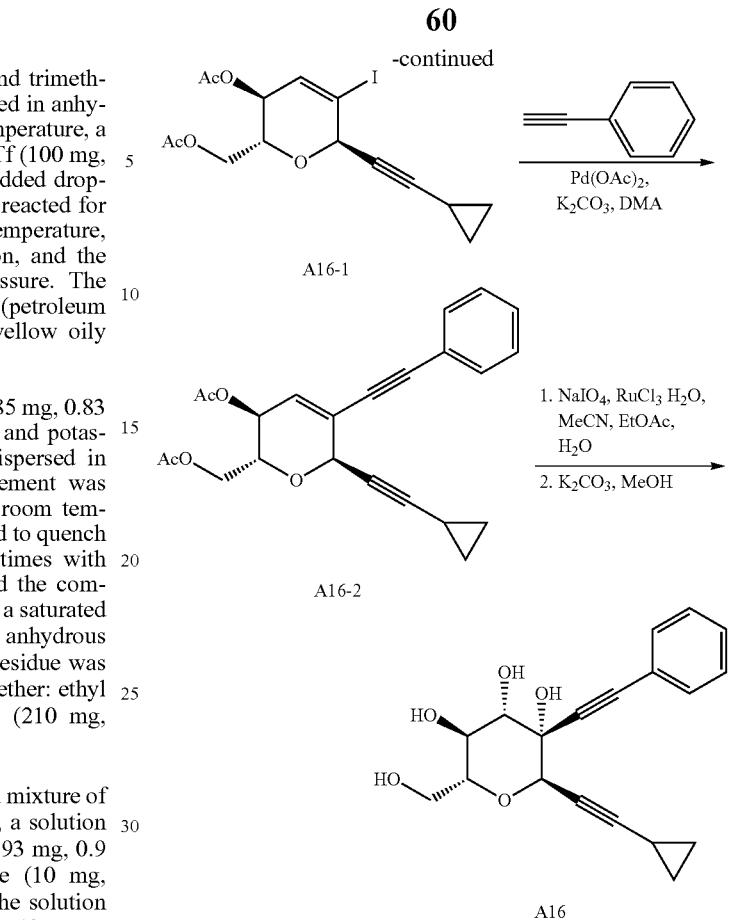

1) Synthesis of an intermediates A16-1

The compound A1-1 (800 mg, 2.0 mmol) and potassium cyclopropylacetenyl fluoroborate (413 mg, 2.4 mmol) were dissolved in anhydrous acetonitrile (6 mL), at 0° C., boron trifluoride ethyl ether (341 mg, 2.4 mmol) was added dropwise, and the solution was heated to the room temperature and reacted for 1 h. Saturated NaHCO$_3$ was added to quench the reaction, the solution was extracted three times with ethyl acetate, organic phases were combined, and the combined organic phase was washed with a saturated salt solution, dried with anhydrous Na$_2$SO$_4$, filtered, and concentrated. The residue was purified by column chromatography (petroleum ether: ethyl acetate=10:1 to 5:1) to obtain a colorless oily product (660 mg, 82%).

2) Synthesis of an intermediate A16-2

A16-1 (202 mg, 0.5 mmol), phenylacetylene (61 mg, 0.6 mmol), palladium acetate (6 mg, 0.025 mmol), and cesium carbonate (245 mg, 0.75 mmol) were dispersed in anhydrous DMF (2.5 mL), nitrogen gas replacement was performed, and the solution was stirred at the room temperature for 3 h. Saturated NaHCO$_3$ was added to quench the reaction, the solution was extracted three times with ethyl ether, organic phases were combined, and the combined organic phase was washed three times with a saturated salt solution. The organic phase was dried with anhydrous sodium sulfate, filtered, and concentrated. The residue was purified by column chromatography (petroleum ether: ethyl acetate=10:1 to 5:1) to obtain a yellow oily product (133 mg, 70%).

3) Synthesis of a product A16

A16-2 (133 mg, 0.35 mmol) was dissolved in a mixture of ethyl acetate/acetonitrile (3.5 mL/3.5 mL), at 0° C., a solution that was newly prepared by dissolving NaIO$_4$ (75 mg, 0.35 mmol) and ruthenium trichloride monohydrate (3 mg, 0.015 mmol) in water (1 mL) was added, and the solution reacted at 0° C. for 5 min. TLC showed that most of the raw materials did not react, a solution that was newly prepared by dissolving NaIO$_4$ (75 mg, 0.35 mmol) and ruthenium trichloride monohydrate (3 mg, 0.015 mmol) in water (1 mL) was added, and the solution reacted for 5 min. Saturated sodium thiosulfate was added to quench the reaction, and the solution was extracted three times with ethyl acetate. Organic phases were combined, and the combined organic phase was washed with a saturated salt solution and concentrated under reduced pressure. The residue was dissolved in methanol (1 mL), potassium carbonate (10 mg, 0.07 mmol) was added, and the solution was stirred at the room temperature overnight. The solution was concentrated under reduced pressure, and the residue was purified by column chromatography (petroleum ether: ethyl acetate=1:1 to ethyl acetate to ethyl acetate: methanol=10:1) to obtain a pale-yellow liquid (30 mg, 26%).

Example 9

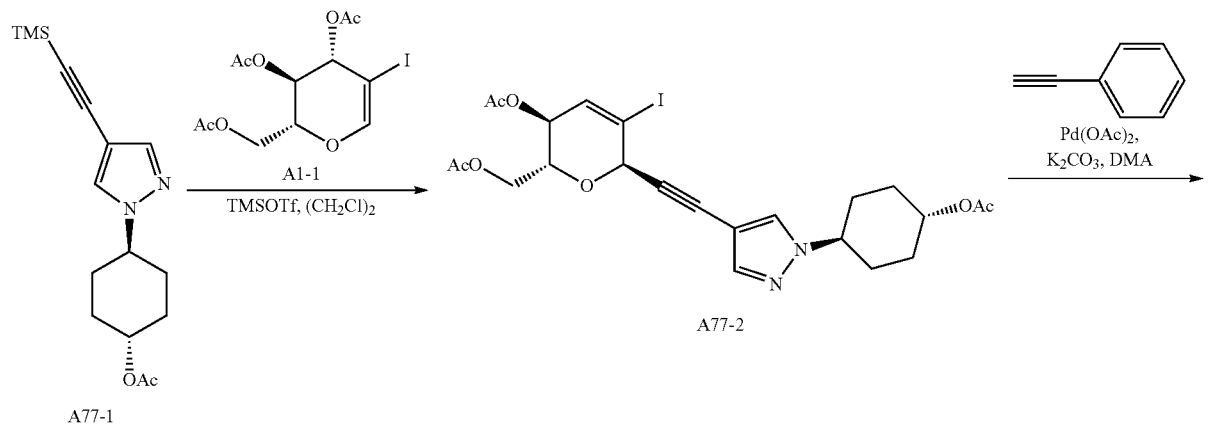

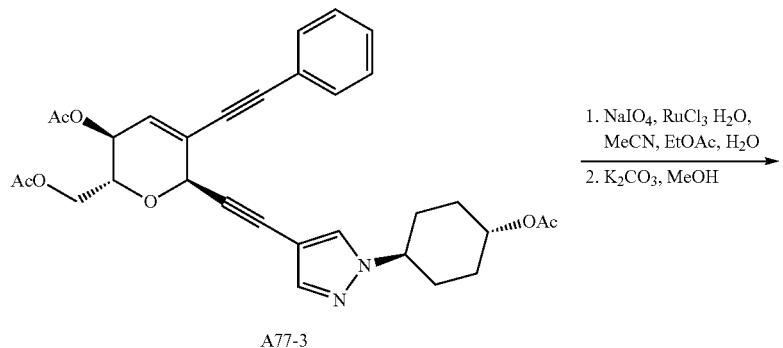

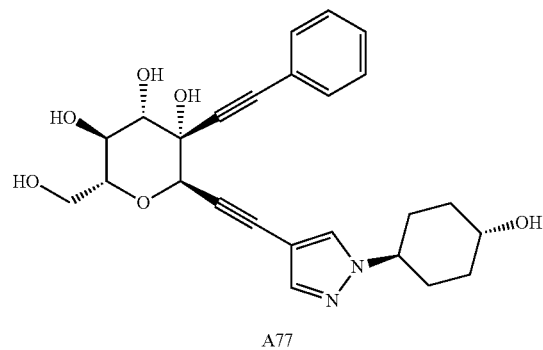

1) Synthesis of an intermediate A77-2

The compound A1-1 (2.75 g, 6.9 mmol) and A77-1 (2.52 g, 8.3 mmol) were dissolved in anhydrous 1,2-dichloroethane (30 mL), at the room temperature, a solution that was prepared by dissolving TMSOTf (921 mg, 4.2 mmol) in 1,2-dichloroethane (3 mL) was added dropwise, and the solution was heated to 80° C. and reacted for 30 min. The solution was cooled to the room temperature, triethylamine was added to quench the reaction, and the solution was concentrated under reduced pressure. The residue was purified by column chromatography (petroleum ether: ethyl acetate=5:1 to 3:1) to obtain a yellow oily product (1.5 g, 38%).

2) Synthesis of an intermediate A77-3

A77-2 (443 mg, 0.78 mmol), phenylacetylene (120 mg, 1.2 mmol), palladium acetate (9 mg, 0.04 mmol), and potassium carbonate (161 mg, 1.2 mmol) were dispersed in anhydrous DMF (2 mL), nitrogen gas replacement was performed, and the solution was stirred at the room temperature overnight. Saturated NaHCO$_3$ was added to quench the reaction, the solution was extracted three times with ethyl ether, organic phases were combined, and the combined organic phase was washed three times with a saturated salt solution. The organic phase was dried with anhydrous sodium sulfate, filtered, and concentrated. The residue was purified by column chromatography (petroleum ether: ethyl acetate=5:1 to 3:1) to obtain a brown oily product (260 mg, 61%).

3) Synthesis of a product A77

A77-3 (260 mg, 0.48 mmol) was dissolved in a mixture of ethyl acetate/acetonitrile (9 mL/9 mL), at 0° C., a solution that was newly prepared by dissolving NaIO$_4$ (205 mg, 0.96 mmol) and ruthenium trichloride monohydrate (9 mg, 0.045 mmol) in water (3 mL) was added, and the solution reacted at 0° C. for 10 min. Saturated sodium thiosulfate was added to quench the reaction, and the solution was extracted three times with ethyl acetate. Organic phases were combined, and the combined organic phase was washed with a saturated salt solution and concentrated under reduced pressure. The residue was dissolved in methanol (1 mL), potassium carbonate (10 mg, 0.07 mmol) was added, and the solution was stirred at the room temperature overnight. The solution was concentrated under reduced pressure, and the residue was purified by using a reversed phase rapid preparative chromatograph (H$_2$O/MeOH=5%-95%) to obtain a pale-yellow solid (20 mg, 9%).

Example 10

Referring to the synthesis method in Example 9, compounds A69 and A76 were synthesized by replacing A77-1 with corresponding trimethylsilyl alkyne at step 1) and replacing phenylacetylene with corresponding alkyne at step 2).

Example 11

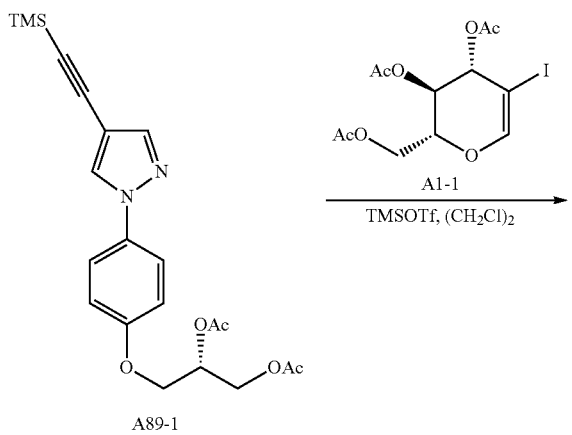

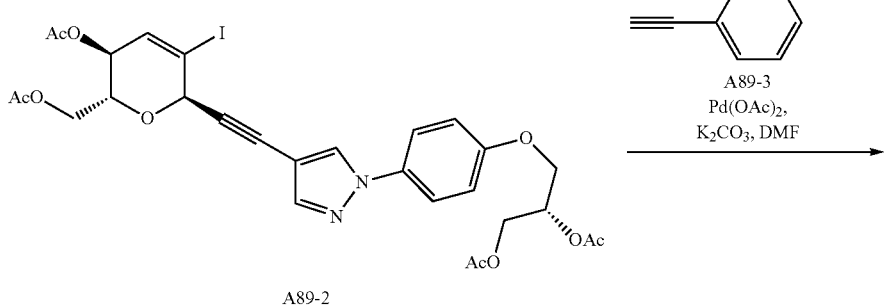

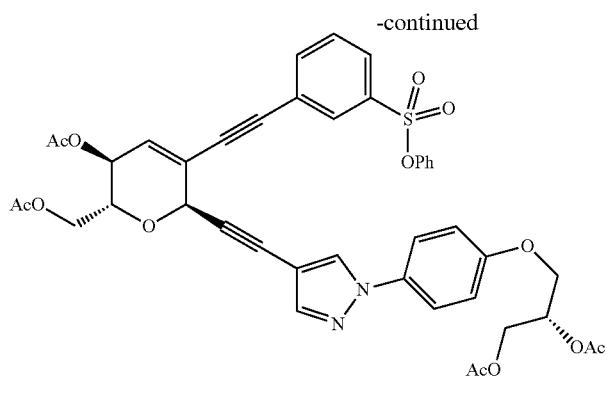

A89-4

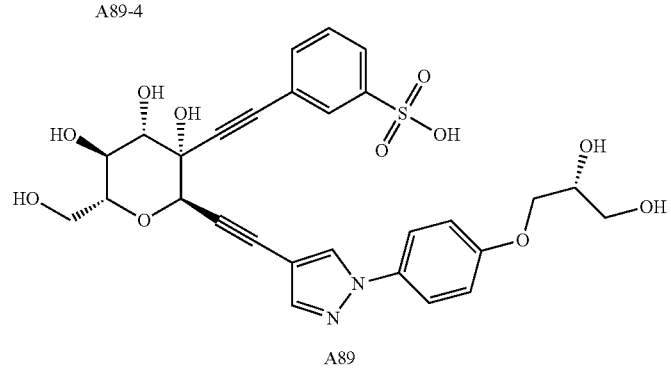

A89

1) Synthesis of an intermediate A89-2

The compound A1-1 (4.3 g, 10.8 mmol) and A89-1 (4.5 g, 10.8 mmol) were dissolved in anhydrous 1,2-dichloroethane (30 mL), at the room temperature, a solution that was prepared by dissolving TMSOTf (1.44 g, 6.5 mmol) in 1,2-dichloroethane (3 mL) was added dropwise, and the solution was heated to 80° C. and reacted for 30 min. The solution was cooled to the room temperature, triethylamine was added to quench the reaction, and the solution was concentrated under reduced pressure. The residue was purified by column chromatography (petroleum ether: ethyl acetate=5:1 to 2:1) to obtain a brown oily product (2.5 g, 34%).

2) Synthesis of an intermediate A8-4

A89-2 (340 mg, 0.5 mmol), A89-3 (155 mg, 0.6 mmol), palladium acetate (6 mg, 0.025 mmol), and potassium carbonate (104 mg, 0.75 mmol) were dispersed in anhydrous DMF (1.5 mL), nitrogen gas replacement was performed, and the solution was stirred at the room temperature overnight. Saturated NaHCO$_3$ was added to quench the reaction, the solution was extracted three times with ethyl acetate, organic phases were combined, and the combined organic phase was washed five times with a saturated salt solution. The organic phase was dried with anhydrous sodium sulfate, filtered, and concentrated. The residue was purified by column chromatography (petroleum ether: ethyl acetate=3:1 to 1:1) to obtain a brown oily product (360 mg, 89%).

3) Synthesis of a product A89

A89-4 (360 mg, 0.44 mmol) was dissolved in a mixture of ethyl acetate/acetonitrile (8 mL/8 mL), at 0° C., a solution that was newly prepared by dissolving NaIO$_4$ (94 mg, 0.44 mmol) and ruthenium trichloride monohydrate (4.6 mg, 0.022 mmol) in water (1.5 mL) was added, the solution reacted at 0° C. for 10 min, a solution that was newly prepared by dissolving NaIO$_4$ (47 mg, 0.22 mmol) and ruthenium trichloride monohydrate (2.3 mg, 0.011 mmol) in water (0.75 mL) was added, and the solution reacted for 10 min. Saturated sodium thiosulfate was added to quench the reaction, and the solution was extracted three times with ethyl acetate. Organic phases were combined, and the combined organic phase was washed with a saturated salt solution and concentrated under reduced pressure. The residue was dissolved in THF (1 mL), a 3 N sodium hydroxide aqueous solution (1.4 mL, 4.2 mmol) was added, and the solution was heated to 70° C. and stirred overnight. The solution was cooled to the room temperature, 2 N HCl (2.2 mL, 4.4 mmol) was added, and the solution was purified by using a reversed phase rapid preparative chromatograph (H$_2$O/MeOH=5%-95%) to obtain a pale-yellow solid (15 mg, 6%).

Example 12

Referring to the synthesis method in Example 11, compounds A86 and A91 were synthesized by replacing A89-3 with

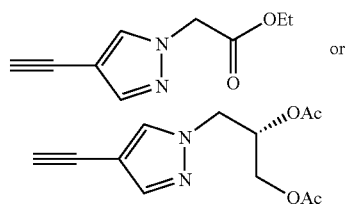

at step 2).

Table 1 Analytical structures and spectral data of 2-alkynylmannose derivatives A1 to A107 synthesized in Examples 1 to 12

| Compound No. | Compound structure | ¹HNMR | Mass spectrum molecular weight |
|---|---|---|---|
| A1 | | ¹H NMR (400 MHz, MeOH-d₄) δ 8.03 (s, 1H), 7.74 (dd, J = 6.4, 6.4 Hz, 2H), 7.53-7.45 (m, 3H), 7.45-7.37 (m, 3H), 7.35-7.29 (m, 3H), 5.49 (s, 1H), 4.09 (d, J = 6.0 Hz, 1H), 3.90-3.70 (m, 4H), 2.94 (s, 3H), 2.38 (s, 3H). | 504.1 [M + H]⁺ |
| A2 | 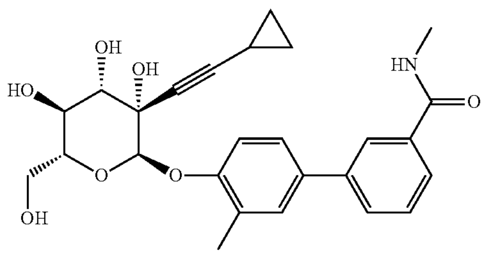 [SMILES: CNC(=O)c1cccc(-c2ccc(O[C@H]3O[C@H](CO)[C@@H](O)[C@H](O)[C@@]3(O)C#CC3CC3)c(C)c2)c1] | ¹H NMR (400 MHz, MeOH-d₄) δ 8.03 (s, 1H), 7.78-7.70 (m, 2H), 7.55-7.43 (m, 3H), 7.33 (d, J = 8.0 Hz, 1H), 5.32 (s, 1H), 3.93 (d, J = 6.4 Hz, 1H), 3.84-3.62 (m, 4H), 2.95 (s, 3H), 2.38 (s, 3H), 1.40-1.28 (m, 1H), 0.81-0.71 (m, 2H), 0.62 (s, 2H). | 467.8 [M + H]⁺ |
| A3 | 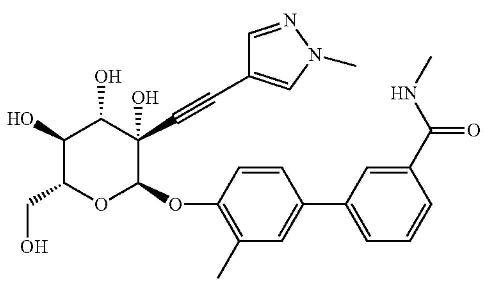 [SMILES: CNC(=O)c1cccc(-c2ccc(O[C@H]3O[C@H](CO)[C@@H](O)[C@H](O)[C@@]3(O)C#Cc3cnn(C)c3)c(C)c2)c1] | ¹H NMR (400 MHz, MeOH-d₄) δ 8.02 (s, 1H), 7.77-7.68 (m, 3H), 7.54-7.42 (m, 4H), 7.45-7.37 (m, 3H), 7.37 (d, J = 8.4 Hz, 3H), 5.43 (s, 1H), 4.06 (d, J = 7.6 Hz, 1H), 3.90-3.70 (m, 7H), 2.94 (s, 3H), 2.36 (s, 3H). | 507.7 [M + H]⁺ |
| A4 | 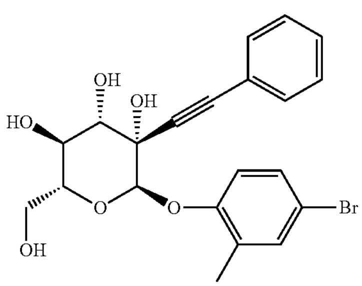 [SMILES: Cc1cc(Br)ccc1O[C@H]1O[C@H](CO)[C@@H](O)[C@H](O)[C@@]1(O)C#Cc1ccccc1] | ¹H NMR (400 MHz, MeOH-d₄) δ 7.44-7.34 (m, 2H), 7.34-7.16 (m, 6H), 6.91 (dd, J = 7.2, 7.2 Hz, 1H), 5.42 (s, 1H), 4.05 (d, J = 5.6 Hz, 1H), 3.90-3.65 (m, 4H), 2.27 (s, 3H). | 471.1 [M + Na]⁺ |
| A5 | 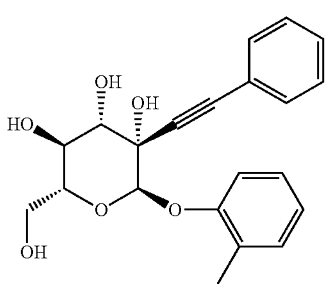 [SMILES: Cc1ccccc1O[C@H]1O[C@H](CO)[C@@H](O)[C@H](O)[C@@]1(O)C#Cc1ccccc1] | ¹H NMR (400 MHz, MeOH-d₄) δ 7.44-7.36 (m, 2H), 7.34-7.26 (m, 4H), 7.16-7.07 (m, 2H), 6.91 (dd, J = 7.2, 7.2 Hz, 1H), 5.44 (s, 1H), 4.09 (d, J = 6.0 Hz, 1H), 3.88-3.68 (m, 4H), 3.59 (dd, J = 9.2, 9.2 Hz, 1H), 2.29 (s, 3H). | 370.7 [M + H]⁺ |

-continued

| Compound No. | Compound structure | ¹HNMR | Mass spectrum molecular weight |
|---|---|---|---|
| A6 | 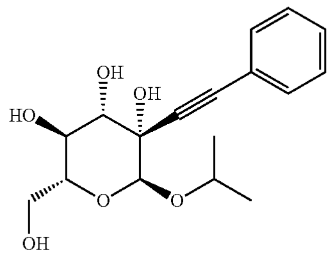 [SMILES: CC(C)O[C@H]1O[C@H](CO)[C@@H](O)[C@H](O)[C@@]1(O)C#Cc1ccccc1] | ¹H NMR (400 MHz, MeOH-d₄) δ 7.48-7.40 (m, 2H), 7.36-7.28 (m, 3H), 4.84 (s, 1H), 4.00 (dq, J = 6.0, 6.0 Hz, 1H), 3.87-3.72 (m, 4H), 1.26 (d, J = 6.4 Hz, 3H), 1.23 (d, J = 6.4 Hz, 3H). | 339.8 [M + NH₄]⁺ |
| A7 | 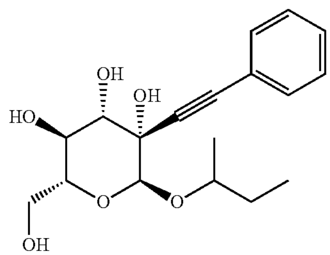 [SMILES: CCC(C)O[C@H]1O[C@H](CO)[C@@H](O)[C@H](O)[C@@]1(O)C#Cc1ccccc1] | ¹H NMR (400 MHz, MeOH-d₄) δ 7.48-7.40 (m, 2H), 7.36-7.28 (m, 3H), 4.85 (s, 1H), 3.87-3.68 (m, 5H), 3.61 (dd, J = 9.2, 9.2 Hz, 1H), 1.71-1.49 (m, 2H), 1.25 (d, J = 6.4 Hz, 1.5H), 1.21 (d, J = 6.4 Hz, 1.5H), 1.02-0.92 (m, 3H). | 353.8 [M + NH₄]⁺ |
| A8 | 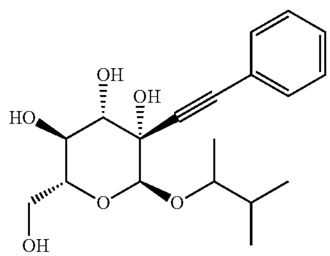 [SMILES: CC(C)C(C)O[C@H]1O[C@H](CO)[C@@H](O)[C@H](O)[C@@]1(O)C#Cc1ccccc1] | ¹H NMR (400 MHz, MeOH-d₄) δ 7.48-7.40 (m, 2H), 7.36-7.28 (m, 3H), 4.86 (s, 1H), 3.88-3.76 (m, 3H), 3.76-3.65 (m, 2H), 3.65-3.56 (m, 1H), 1.90-1.75 (m, 1H), 1.21 (d, J = 6.4 Hz, 1.5H), 1.17 (d, J = 6.4 Hz, 1.5H), 1.02-0.92 (m, 6H). | 367.8 [M + NH₄]⁺ |
| A9 | 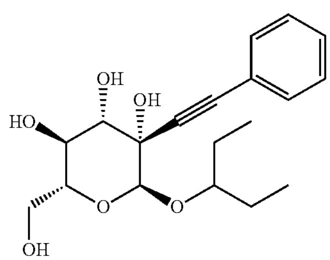 [SMILES: CCC(CC)O[C@H]1O[C@H](CO)[C@@H](O)[C@H](O)[C@@]1(O)C#Cc1ccccc1] | ¹H NMR (400 MHz, MeOH-d₄) δ 7.48-7.40 (m, 2H), 7.36-7.28 (m, 3H), 4.85 (s, 1H), 3.87-3.76 (m, 3H), 3.76-3.69 (m, 1H), 3.69-3.56 (m, 2H), 1.74-1.52 (m, 4H), 0.96 (t, J = 7.2 Hz, 6H). | 367.8 [M + NH₄]⁺ |
| A10 | 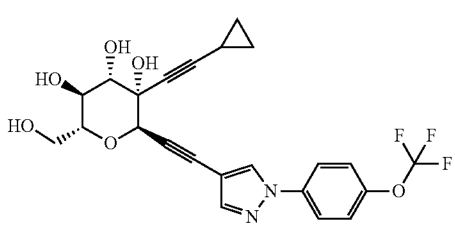 [SMILES: OC[C@H]1O[C@H](C#Cc2cnn(-c3ccc(OC(F)(F)F)cc3)c2)[C@](O)(C#CC2CC2)[C@@H](O)[C@@H]1O] | ¹H NMR (400 MHz, DMSO-d₆ + D₂O) δ 8.78 (s, 1H), 7.95 (d, J = 8.8 Hz, 2H), 7.92 (s, 1H), 7.51 Xd, J = 8.8 Hz, 2H), 4.61 (s, 1H), 3.67-3.56 (m, 3H), 3.43 (dd, J = 12.0, 6.0 Hz, 1H), 3.28 (dd, J = 9.6, 9.6 Hz, 1H), 1.32-1.24 (m, 1H), 0.77-0.70 (m, 2H), 0.55-0.50 (m, 2H). | 479.1 [M + H]⁺ |
| A11 | 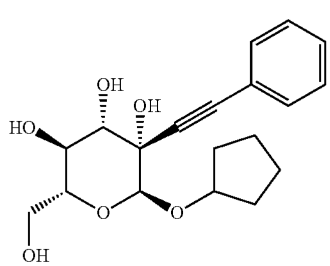 [SMILES: OC[C@H]1O[C@H](OC2CCCC2)[C@](O)(C#Cc2ccccc2)[C@@H](O)[C@@H]1O] | ¹H NMR (400 MHz, MeOH-d₄) δ 7.48-7.40 (m, 2H), 7.36-7.28 (m, 3H), 4.80 (s, 1H), 4.38-4.30 (m, 1H), 3.88-3.76 (m, 2H), 3.76-3.67 (m, 2H), 3.59 (dd, J = 9.2, 9.2 Hz, 1H), 1.94-1.84 (m, 1H), 1.84-1.62 (m, 5H), 1.62-1.50 (m, 2H). | 370.8 [M + Na]⁺ |

| Compound No. | Compound structure | ¹HNMR | Mass spectrum molecular weight |
|---|---|---|---|
| A12 | 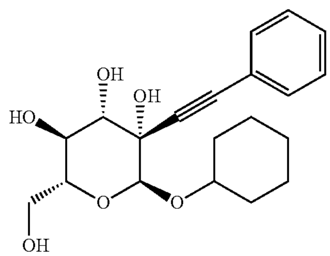 [SMILES: OC[C@H]1O[C@H](OC2CCCCC2)[C@](O)(C#Cc2ccccc2)[C@@H](O)[C@@H]1O] | ¹H NMR (400 MHz, MeOH-d₄) δ 7.48-7.40 (m, 2H), 7.36-7.28 (m, 3H), 4.84 (s, 1H), 3.88-3.80 (m, 2H), 3.80-3.67 (m, 3H), 3.59 (dd, J = 9.2, 9.2 Hz, 1H), 1.92-1.70 (m, 4H), 1.60-1.42 (m, 3H), 1.42-1.25 (m, 3H). | |
| A13 | 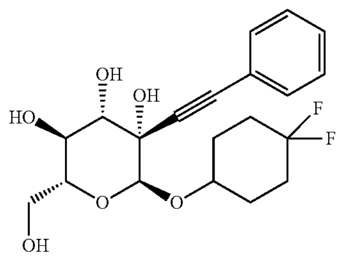 [SMILES: OC[C@H]1O[C@H](OC2CCC(F)(F)CC2)[C@](O)(C#Cc2ccccc2)[C@@H](O)[C@@H]1O] | ¹H NMR (400 MHz, MeOH-d₄) δ 7.48-7.40 (m, 2H), 7.36-7.28 (m, 3H), 4.84 (s, 1H), 4.06-3.98 (m, 1H), 3.90-3.80 (m, 2H), 3.76-3.66 (m, 2H), 3.58 (dd, J = 9.2, 9.2 Hz, 1H), 2.35-1.97 (m, 3H), 1.97-1.70 (m, 5H). | 415.8 [M + NH₄]⁺ |
| A14 | 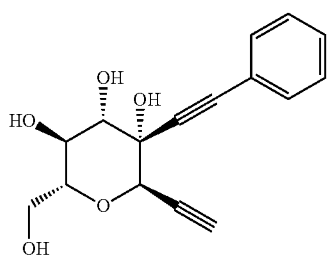 [SMILES: C#C[C@H]1O[C@H](CO)[C@@H](O)[C@H](O)[C@@]1(O)C#Cc1ccccc1] | | 289.1 [M + H]⁺ |
| A15 | 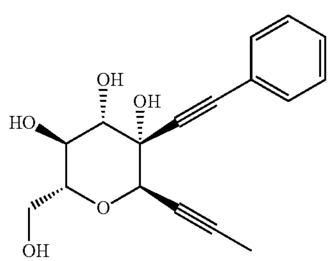 [SMILES: CC#C[C@H]1O[C@H](CO)[C@@H](O)[C@H](O)[C@@]1(O)C#Cc1ccccc1] | ¹H NMR (400 MHz, MeOH-d₄) δ 7.49-7.40 (m, 2H), 7.38-7.26 (m, 3H), 4.62 (s, 1H), 3.96-3.79 (m, 3H), 3.72 (dd, J = 11.2, 5.2 Hz, 1H), 3.56 (dd, J = 9.6, 9.6 Hz, 1H), 1.90 (s, 3H). | 319.8 [M + NH₄]⁺ |
| A16 | 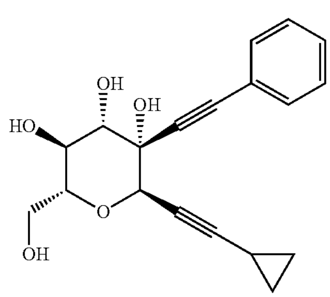 [SMILES: OC[C@H]1O[C@H](C#CC2CC2)[C@](O)(C#Cc2ccccc2)[C@@H](O)[C@@H]1O] | ¹H NMR (400 MHz, MeOH-d₄) δ 7.49-7.40 (m, 2H), 7.38-7.26 (m, 3H), 4.62 (s, 1H), 3.93-3.79 (m, 3H), 3.71 (dd, J = 11.6, 5.6 Hz, 1H), 3.55 (dd, J = 9.6, 9.6 Hz, 1H), 1.40-1.23 (m, 1H), 0.86-0.77 (m, 2H), 0.65 (s, 2H). | 345.8 [M + NH₄]⁺ |

-continued

| Compound No. | Compound structure | ¹HNMR | Mass spectrum molecular weight |
|---|---|---|---|
| A17 | 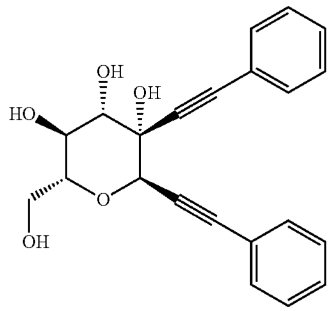 [SMILES: OC[C@H]1O[C@H](C#Cc2ccccc2)[C@](O)(C#Cc2ccccc2)[C@@H](O)[C@@H]1O] | ¹H NMR (400 MHz, DMSO-d$_6$ + D$_2$O) δ 7.45-7.30 (m, 10H), 4.81 (s, 1H), 3.78 (d, J = 9.2 Hz, 1H), 3.76-3.67 (m, 3H), 3.47 (dd, J = 11.6, 6.0 Hz, 1H), 3.36 (dd, J = 9.2, 9.2 Hz, 1H). | 381.8 [M + NH$_4$]$^+$ |
| A18 | 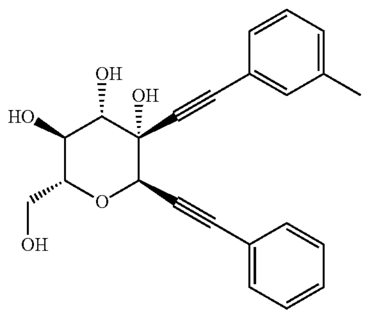 [SMILES: Cc1cccc(C#C[C@@]2(O)[C@@H](C#Cc3ccccc3)O[C@H](CO)[C@@H](O)[C@@H]2O)c1] | ¹H NMR (400 MHz, MeOH-d$_4$) δ 7.45 (d, J = 6.8 Hz, 2H), 7.40-7.30 (m, 3H), 7.28-7.12 (m, 4H), 4.92 (s, 1H), 4.03 (d, J = 9.2 Hz, 1H), 4.00-3.93 (m, 1H), 3.90 (d, J = 12.0 Hz, 1H), 3.76 (dd, J = 11.6, 5.6 Hz, 1H), 3.63 (dd, J = 9.2, 9.2 Hz, 1H). | 395.8 [M + NH$_4$]$^+$ |
| A19 | 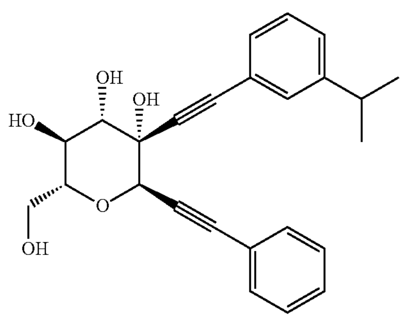 [SMILES: CC(C)c1cccc(C#C[C@@]2(O)[C@@H](C#Cc3ccccc3)O[C@H](CO)[C@@H](O)[C@@H]2O)c1] | | 423.8 [M + NH$_4$]$^+$ |
| A20 | 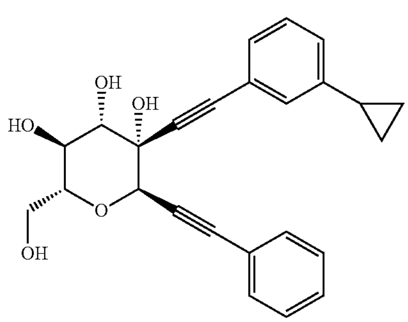 [SMILES: OC[C@H]1O[C@H](C#Cc2ccccc2)[C@](O)(C#Cc2cccc(C3CC3)c2)[C@@H](O)[C@@H]1O] | | 421.8 [M + NH$_4$]$^+$ |

| Compound No. | Compound structure | ¹HNMR | Mass spectrum molecular weight |
|---|---|---|---|
| A21 | 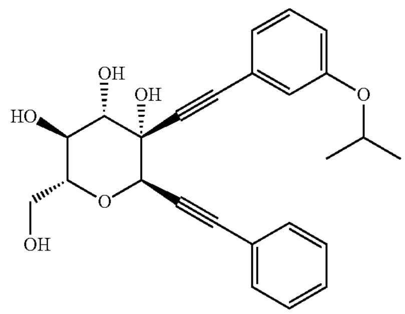 [SMILES: CC(C)Oc1cccc(C#C[C@@]2(O)[C@@H](C#Cc3ccccc3)O[C@H](CO)[C@@H](O)[C@@H]2O)c1] | | 439.8 [M + NH₄]⁺ |
| A22 | 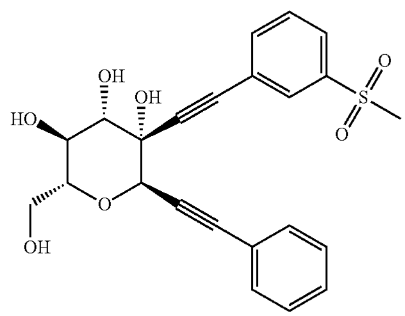 [SMILES: CS(=O)(=O)c1cccc(C#C[C@@]2(O)[C@@H](C#Cc3ccccc3)O[C@H](CO)[C@@H](O)[C@@H]2O)c1] | ¹H NMR (400 MHz, MeOH-d₄) δ 8.04 (s, 1H), 7.92 (d, J = 7.6 Hz, 1H), 7.76 (d, J = 7.6 Hz, 1H), 7.61 (dd, J = 7.6, 7.6 Hz, 1H), 7.50-7.43 (m, 2H), 7.38-7.30 (m, 3H), 4.95 (s, 1H), 4.04 (d, J = 9.2 Hz, 1H), 4.00-3.93 (m, 1H), 3.91 (d, J = 11.6 Hz, 1H), 3.75 (dd, J = 11.6, 5.6 Hz, 1H), 3.63 (dd, J = 9.2, 9.2 Hz, 1H). | 459.7 [M + NH₄]⁺ |
| A23 | 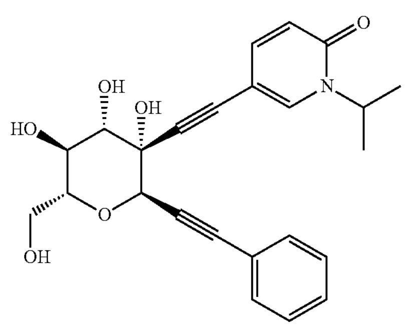 [SMILES: CC(C)n1cc(C#C[C@@]2(O)[C@@H](C#Cc3ccccc3)O[C@H](CO)[C@@H](O)[C@@H]2O)ccc1=O] | | 423.7 [M + H]⁺ |
| A24 | 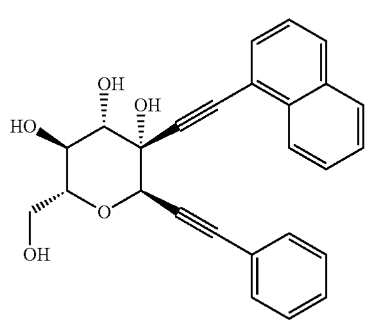 [SMILES: OC[C@H]1O[C@H](C#Cc2ccccc2)[C@](O)(C#Cc2cccc3ccccc23)[C@@H](O)[C@@H]1O] | ¹H NMR (400 MHz, MeOH-d₄) δ 8.41 (d, J = 8.4 Hz, 1H), 7.84 (dd, J = 7.2, 7.2 Hz, 2H), 7.69 (d, J = 7.2 Hz, 1H), 7.53-7.28 (m, 7H), 7.14 (dd, J = 7.2, 7.2 Hz, 1H), 5.04 (s, 1H), 4.17 (d, J = 9.2 Hz, 1H), 4.08-4.00 (m, 1H), 3.93 (d, J = 11.6 Hz, 1H), 3.79 (dd, J = 11.6, 5.6 Hz, 1H), 3.69 (dd, J = 9.2, 9.2 Hz, 1H). | 431.8 [M + NH₄]⁺ |

| Compound No. | Compound structure | ¹HNMR | Mass spectrum molecular weight |
|---|---|---|---|
| A25 | 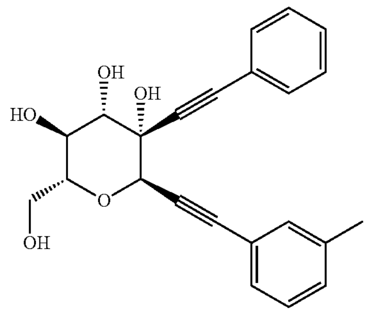 [SMILES: Cc1cccc(C#C[C@H]2O[C@H](CO)[C@@H](O)[C@H](O)[C@@]2(O)C#Cc2ccccc2)c1] | | 395.8 [M + NH₄]⁺ |
| A26 | 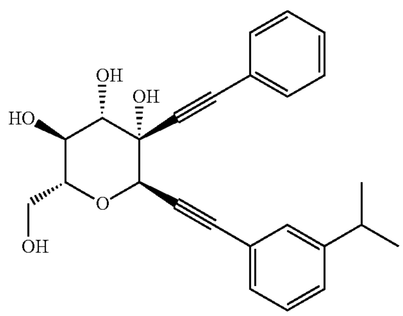 [SMILES: CC(C)c1cccc(C#C[C@H]2O[C@H](CO)[C@@H](O)[C@H](O)[C@@]2(O)C#Cc2ccccc2)c1] | | 423.8 [M + NH₄]⁺ |
| A27 | 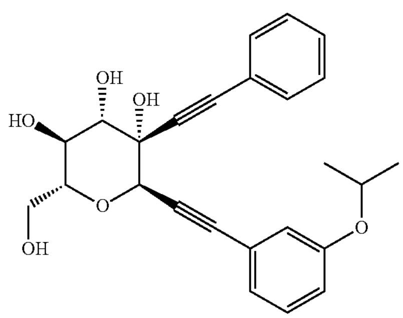 [SMILES: CC(C)Oc1cccc(C#C[C@H]2O[C@H](CO)[C@@H](O)[C@H](O)[C@@]2(O)C#Cc2ccccc2)c1] | | 439.7 [M + NH₄]⁺ |
| A28 | 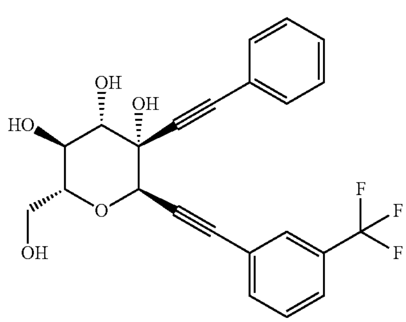 [SMILES: OC[C@H]1O[C@H](C#Cc2cccc(C(F)(F)F)c2)[C@](O)(C#Cc2ccccc2)[C@@H](O)[C@@H]1O] | | 449.7 [M + NH₄]⁺ |

-continued

| Compound No. | Compound structure | ¹HNMR | Mass spectrum molecular weight |
|---|---|---|---|
| A29 | 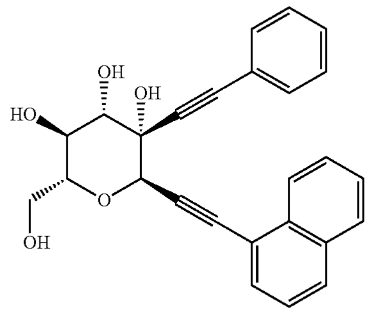 [SMILES: OC[C@H]1O[C@H](C#Cc2cccc3ccccc23)[C@](O)(C#Cc2ccccc2)[C@@H](O)[C@@H]1O] | ¹H NMR (400 MHz, DMSO-d$_6$ + D$_2$O) δ 8.25 (d, J = 8.8 Hz, 1H), 7.95 (dd, J = 12.0, 12.0 Hz, 2H), 7.70 (d, J = 6.8 Hz, 1H), 7.51 (dd, J = 1.6, 7.6 Hz, 2H), 7.46-7.39 (m, 2H), 7.38-7.30 (m, 3H), 7.23 (dd, J = 7.6, 7.6 Hz, 1H), 4.99 (s, 1H), 3.86 (d, J = 8.8 Hz, 1H), 3.85-3.75 (m, 2H), 3.51 (dd, J = 11.6, 5.6 Hz, 1H), 3.40 (dd, J = 9.2, 9.2 Hz, 1H). | 431.7 [M + NH$_4$]$^+$ |
| A30 | 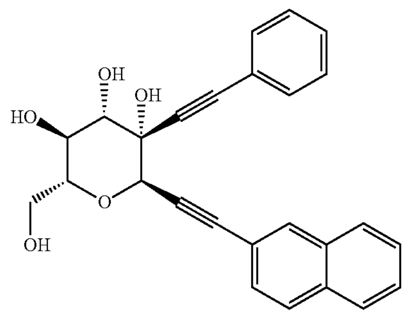 [SMILES: OC[C@H]1O[C@H](C#Cc2ccc3ccccc3c2)[C@](O)(C#Cc2ccccc2)[C@@H](O)[C@@H]1O] | ¹H NMR (400 MHz, MeOH-d$_4$) δ 7.98 (s, 1H), 7.88-7.79 (m, 2H), 7.80-7.72 (m, 1H), 7.49-7.40 (m, 2H), 7.55-7.43 (m, 5H), 7.38-7.26 (m, 3H), 4.98 (s, 1H), 4.09 (d, J = 8.8 Hz, 1H), 4.08-3.97 (m, 1H), 3.93 (d, J = 11.6 Hz, 1H), 3.78 (dd, J = 11.6, 5.2 Hz, 1H), 3.66 (dd, J = 9,6, 9.6 Hz, 1H). | 431.7 [M + NH$_4$]$^+$ |
| A31 | 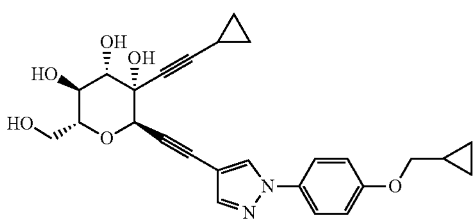 [SMILES: OC[C@H]1O[C@H](C#Cc2cnn(-c3ccc(OCC4CC4)cc3)c2)[C@](O)(C#CC2CC2)[C@@H](O)[C@@H]1O] | ¹H NMR (400 MHz, DMSO-d$_6$ + D$_2$O) δ 8.58 (s, 1H), 7.82 (s, 1H), 7.68 (d, J = 8.8 Hz, 2H), 7.02 (d, J = 8.8 Hz, 2H), 4.59 (s, 1H), 3.89-3.70 (m, 2H), 3.67-3.56 (m, 3H), 3.43 (dd, J = 12.0, 6.0 Hz, 1H), 3.27 (dd, J = 9.6, 9.6 Hz, 1H), 1.32-1.15 (m, 2H), 0.77-0.70 (m, 2H), 0.59-0.49 (m, 4H). | 465.2 [M + H]$^+$ |
| A32 | 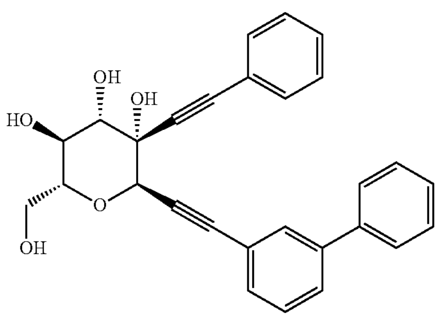 [SMILES: OC[C@H]1O[C@H](C#Cc2cccc(-c3ccccc3)c2)[C@](O)(C#Cc2ccccc2)[C@@H](O)[C@@H]1O] | ¹H NMR (400 MHz, DMSO-d$_6$ + D$_2$O) δ 7.68 (d, J = 6.8 Hz, 1H), 7.62 (s, 1H), 7.54 (d, J = 6.4 Hz, 2H), 7.52-7.29 (m, 10H), 4.84 (s, 1H), 3.85-3.75 (m, 2H), 3.55-3.43 (m, 2H), 3.36 (dd, J = 9.2, 9.2 Hz, 1H). | 457.7 [M + NH$_4$]$^+$ |
| A33 | 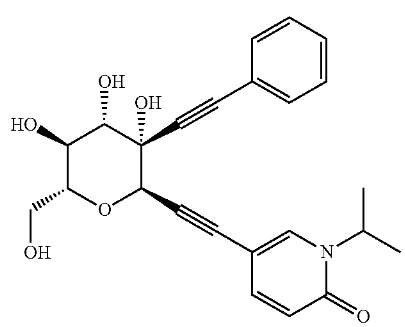 [SMILES: CC(C)n1cc(C#C[C@H]2O[C@H](CO)[C@@H](O)[C@H](O)[C@@]2(O)C#Cc2ccccc2)ccc1=O] | | 423.7 [M + H]$^+$ |

-continued

| Compound No. | Compound structure | ¹HNMR | Mass spectrum molecular weight |
|---|---|---|---|
| A34 | 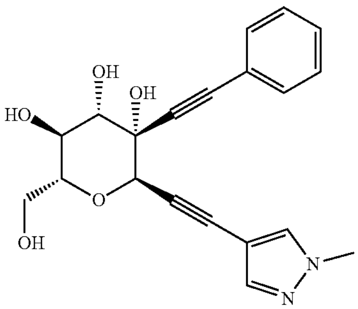 [SMILES: Cn1cc(C#C[C@H]2O[C@H](CO)[C@@H](O)[C@H](O)[C@@]2(O)C#Cc2ccccc2)cn1] | ¹H NMR (400 MHz, MeOH-d₄) δ 7.77 (s, 1H), 7.54 (s, 1H), 7.47-7.40 (m, 2H), 7.38-7.26 (m, 3H), 4.82 (s, 1H), 3.98 (d, J = 9.2 Hz, 1H), 3.95-3.82 (m, 5H), 3.73 (dd, J = 11.2, 5.6 Hz, 1H), 3.60 (dd, J = 9.6, 9.6 Hz, 1H). | 368.8 [M + H]⁺ |
| A35 | 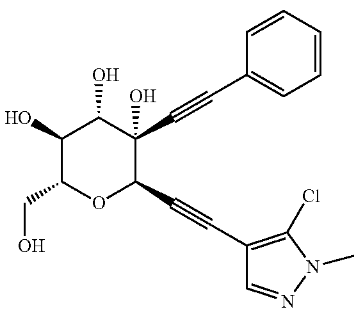 [SMILES: Cn1ncc(C#C[C@H]2O[C@H](CO)[C@@H](O)[C@H](O)[C@@]2(O)C#Cc2ccccc2)c1Cl] | ¹H NMR (400 MHz, MeOH-d₄) δ 7.60 (s, 1H), 7.47-7.38 (m, 2H), 7.37-7.27 (m, 3H), 4.82 (s, 1H), 4.02 (d, J = 9.2 Hz, 1H), 3.96-3.90 (m, 1H), 3.88 (d, J = 12.0 Hz, 1H), 3.82 (s, 3H), 3.74 (dd, J = 11.2, 5.6 Hz, 1H), 3.62 (dd, J = 9.6, 9.6 Hz, 1H). | 402.7 [M + H]⁺ |
| A36 | 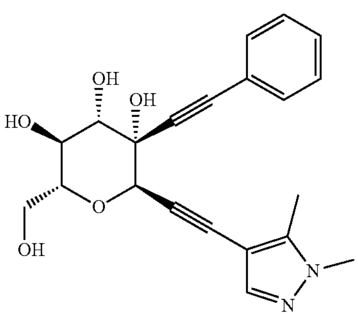 [SMILES: Cc1c(C#C[C@H]2O[C@H](CO)[C@@H](O)[C@H](O)[C@@]2(O)C#Cc2ccccc2)cnn1C] | | 382.8 [M + H]⁺ |
| A37 | 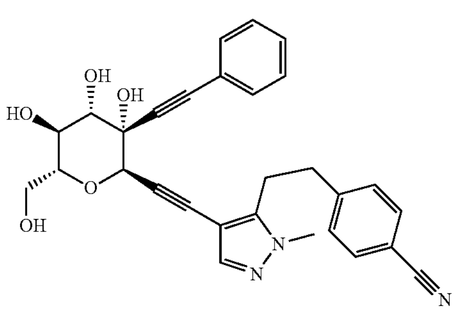 [SMILES: Cn1ncc(C#C[C@H]2O[C@H](CO)[C@@H](O)[C@H](O)[C@@]2(O)C#Cc2ccccc2)c1CCc1ccc(C#N)cc1] | | 499.7 [M + H]⁺ |

-continued

| Compound No. | Compound structure | ¹HNMR | Mass spectrum molecular weight |
|---|---|---|---|
| A38 | 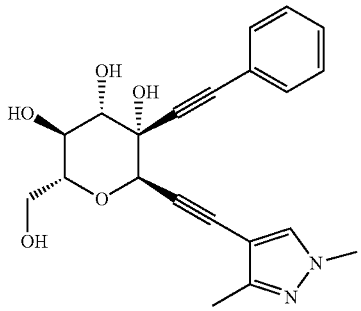 [SMILES: Cc1nn(C)cc1C#C[C@H]1O[C@H](CO)[C@@H](O)[C@H](O)[C@@]1(O)C#Cc1ccccc1] | | 382.8 [M + H]⁺ |
| A39 | 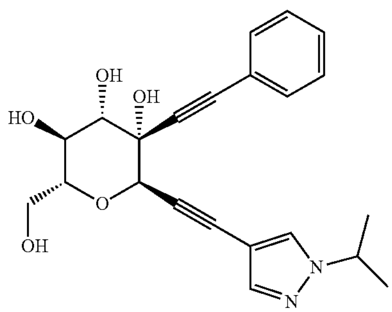 [SMILES: CC(C)n1cc(C#C[C@H]2O[C@H](CO)[C@@H](O)[C@H](O)[C@@]2(O)C#Cc2ccccc2)cn1] | ¹H NMR (400 MHz, MeOH-d₄) δ 7.85 (s, 1H), 7.55 (s, 1H), 7.47-7.40 (m, 2H), 7.38-7.26 (m, 3H), 4.81 (s, 1H), 4.56-4.43 (m, 1H), 3.99 (d, J = 8.8 Hz, 1H), 3.95-3.82 (m, 2H), 3.74 (dd, J = 11.6, 5.6 Hz, 1H), 3.61 (dd, J = 9.6, 9.6 Hz, 1H), 1.46 (d, J = 6.4 Hz, 6H). | 396.8 [M + H]⁺ |
| A40 | 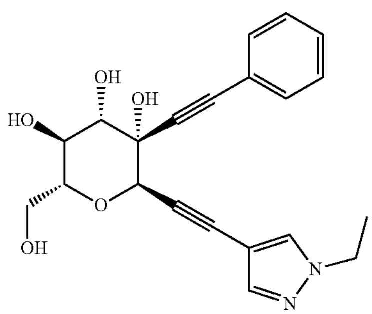 [SMILES: CCn1cc(C#C[C@H]2O[C@H](CO)[C@@H](O)[C@H](O)[C@@]2(O)C#Cc2ccccc2)cn1] | ¹H NMR (400 MHz, MeOH-d₄) δ 7.83 (s, 1H), 7.56 (s, 1H), 7.47-7.40 (m, 2H), 7.38-7.26 (m, 3H), 4.82 (s, 1H), 4.16 (q, J = 7.2 Hz, 2H), 3.99 (d, J = 9.2 Hz, 1H), 3.95-3.82 (m, 2H), 3.74 (dd, J = 11.6, 5.6 Hz, 1H), 3.60 (dd, J = 9.6, 9.6 Hz, 1H), 1.43 (t, J = 7.2 Hz, 3H). | 382.8 [M + H]⁺ |
| A41 | 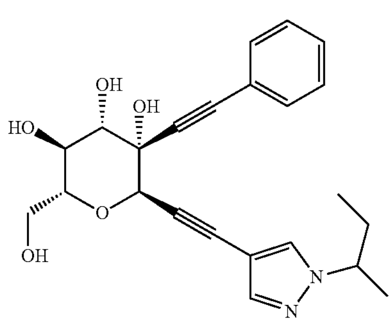 [SMILES: CCC(C)n1cc(C#C[C@H]2O[C@H](CO)[C@@H](O)[C@H](O)[C@@]2(O)C#Cc2ccccc2)cn1] | ¹H NMR (400 MHz, MeOH-d₄) δ 7.84 (s, 1H), 7.56 (s, 1H), 7.47-7.40 (m, 2H), 7.38-7.26 (m, 3H), 4.82 (s, 1H), 4.30-4.17 (m, 1H), 4.00 (d, J = 8.8 Hz, 1H), 3.95-3.82 (m, 2H), 3.74 (dd, J = 11.6, 5.6 Hz, 1H), 3.60 (dd, J = 9.6, 9.6 Hz, 1H), 1.93-1.70 (m, 2H), 1.45 (d, J = 6.4 Hz, 3H), 0.76 (t, J = 6.4 Hz, 3H). | 410.8 [M + H]⁺ |

-continued

| Compound No. | Compound structure | ¹HNMR | Mass spectrum molecular weight |
|---|---|---|---|
| A42 | 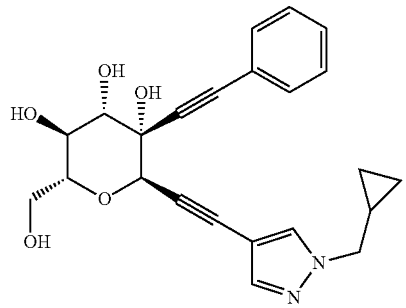 [SMILES: OC[C@H]1O[C@H](C#Cc2cnn(CC3CC3)c2)[C@](O)(C#Cc2ccccc2)[C@@H](O)[C@@H]1O] | | 408.8 [M + H]⁺ |
| A43 | 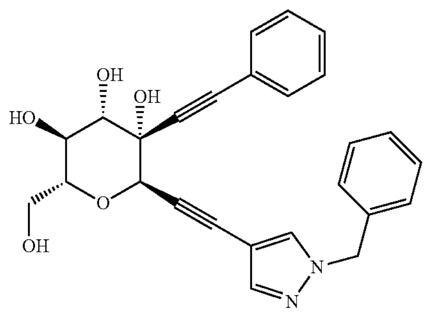 [SMILES: OC[C@H]1O[C@H](C#Cc2cnn(Cc3ccccc3)c2)[C@](O)(C#Cc2ccccc2)[C@@H](O)[C@@H]1O] | ¹H NMR (400 MHz, MeOH-d₄) δ 7.86 (s, 1H), 7.59 (s, 1H), 7.41 (d, J = 5.8 Hz, 2H), 7.37-7.24 (m, 6H), 7.22 (d, J = 5.4 Hz, 2H), 5.31 (s, 2H), 4.82 (s, 1H), 4.98 (d, J = 8.8 Hz, 1H), 3.95-3.82 (m, 2H), 3.73 (dd, J = 10.8, 5.6 Hz, 1H), 3.59 (dd, J = 9.2, 9.2 Hz, 1H). | 444.8 [M + H]⁺ |
| A44 | 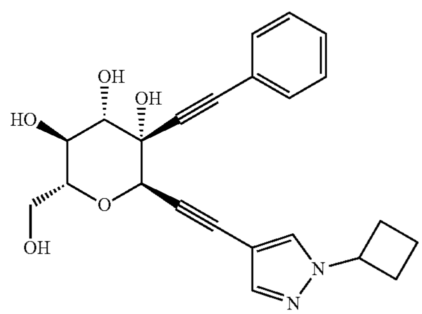 [SMILES: OC[C@H]1O[C@H](C#Cc2cnn(C3CCC3)c2)[C@](O)(C#Cc2ccccc2)[C@@H](O)[C@@H]1O] | ¹H NMR (400 MHz, MeOH-d₄) δ 7.87 (s, 1H), 7.57 (s, 1H), 7.47-7.40 (m, 2H), 7.38-7.26 (m, 3H), 4.92 (s, 1H), 4.84-4.72 (m, 1H), 3.99 (d, J = 9.2 Hz, 1H), 3.95-3.82 (m, 2H), 3.74 (dd, J = 11.6, 5.6 Hz, 1H), 3.61 (dd, J = 9.2, 9.2 Hz, 1H), 2.55-2.40 (m, 4H), 1.93-1.80 (m, 2H). | 408.8 [M + H]⁺ |
| A45 | 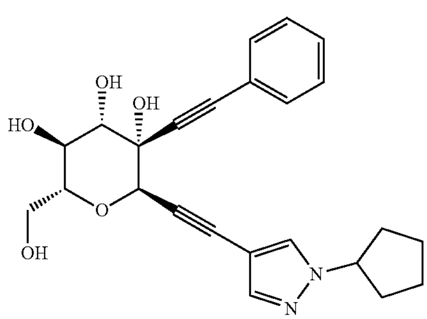 [SMILES: OC[C@H]1O[C@H](C#Cc2cnn(C3CCCC3)c2)[C@](O)(C#Cc2ccccc2)[C@@H](O)[C@@H]1O] | ¹H NMR (400 MHz, MeOH-d₄) δ 7.84 (s, 1H), 7.55 (s, 1H), 7.47-7.40 (m, 2H), 7.38-7.26 (m, 3H), 4.82 (s, 1H), 4.72-4.64 (m, 1H), 4.10-3.95 (m, 3H), 3.99 (d, J = 9.2 Hz, 1H), 3.95-3.82 (m, 2H), 3.73 (dd, J = 11.6, 5.6 Hz, 1H), 3.60 (dd, J = 9.6, 9.6 Hz, 1H), 2.25-2.05 (m, 2H), 2.00-1.78 (m, 4H), 1.77-1.65 (m, 2H). | 422.8 [M + H]⁺ |

-continued

| Compound No. | Compound structure | ¹HNMR | Mass spectrum molecular weight |
|---|---|---|---|
| A46 | 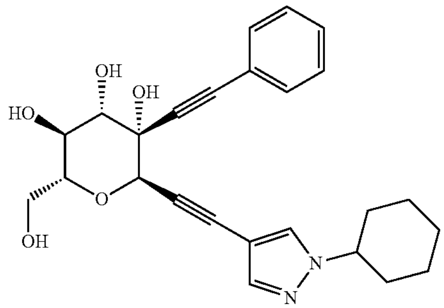 [SMILES: OC[C@H]1O[C@H](C#Cc2cnn(C3CCCCC3)c2)[C@](O)(C#Cc2ccccc2)[C@@H](O)[C@@H]1O] | | 436.8 [M + H]⁺ |
| A47 | 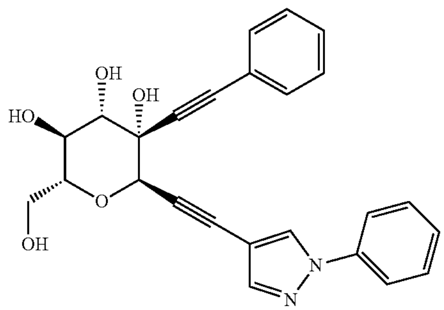 [SMILES: OC[C@H]1O[C@H](C#Cc2cnn(-c3ccccc3)c2)[C@](O)(C#Cc2ccccc2)[C@@H](O)[C@@H]1O] | ¹H NMR (400 MHz, MeOH-d₄) δ 8.44 (s, 1H), 7.88 (s, 1H), 7.73 (d, J = 8.0 Hz, 2H), 7.52-7.42 (m, 4H), 7.38-7.28 (m, 4H), 4.92 (s, 1H), 4.02 (d, J = 9.2 Hz, 1H), 4.00-3.92 (m, 1H), 3.90 (d, J = 12.0 Hz, 1H), 3.75 (dd, J = 12.0, 5.6 Hz, 1H), 3.62 (dd, J = 9.6, 9.6 Hz, 1H). | 430.8 [M + H]⁺ |
| A48 | 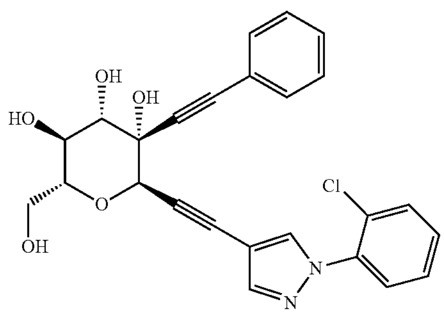 [SMILES: OC[C@H]1O[C@H](C#Cc2cnn(-c3ccccc3Cl)c2)[C@](O)(C#Cc2ccccc2)[C@@H](O)[C@@H]1O] | ¹H NMR (400 MHz, MeOH-d₄) δ 8.18 (s, 1H), 7.82 (s, 1H), 7.66-7.52 (m, 2H), 7.52-7.40 (m, 4H), 7.38-7.26 (m, 3H), 4.92 (s, 1H), 4.03 (d, J = 8.8 Hz, 1H), 4.00-3.92 (m, 1H), 3.90 (d, J = 12.0 Hz, 1H), 3.75 (dd, J = 11.6, 5.6 Hz, 1H), 3.62 (dd, J = 9.2, 9.2 Hz, 1H). | 464.8 [M + H]⁺ |
| A49 | 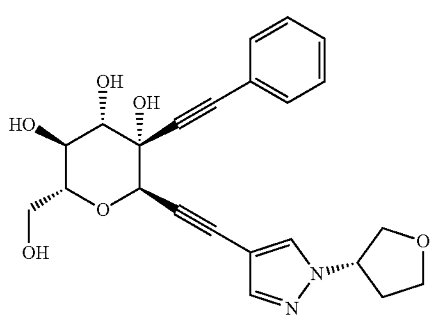 [SMILES: OC[C@H]1O[C@H](C#Cc2cnn([C@H]3CCOC3)c2)[C@](O)(C#Cc2ccccc2)[C@@H](O)[C@@H]1O] | | 424.7 [M + H]⁺ |

-continued

| Compound No. | Compound structure | ¹HNMR | Mass spectrum molecular weight |
|---|---|---|---|
| A50 | 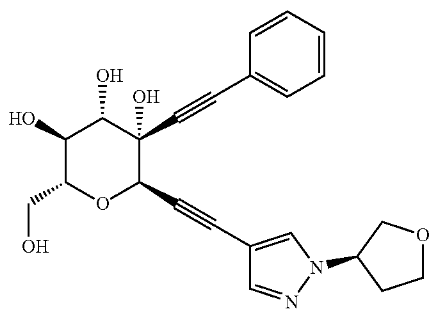 [SMILES: OC[C@H]1O[C@H](C#Cc2cnn([C@@H]3CCOC3)c2)[C@](O)(C#Cc2ccccc2)[C@@H](O)[C@@H]1O] | | 424.8 [M + H]⁺ |
| A51 | 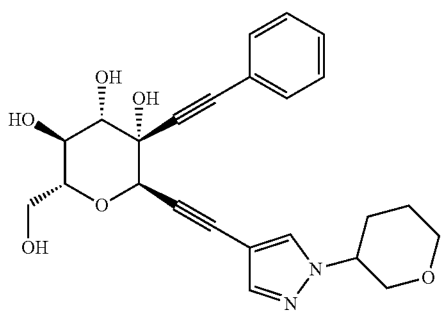 [SMILES: OC[C@H]1O[C@H](C#Cc2cnn(C3CCCOC3)c2)[C@](O)(C#Cc2ccccc2)[C@@H](O)[C@@H]1O] | | 438.9 [M + H]⁺ |
| A52 | 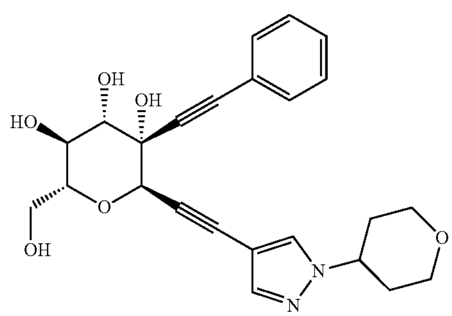 [SMILES: OC[C@H]1O[C@H](C#Cc2cnn(C3CCOCC3)c2)[C@](O)(C#Cc2ccccc2)[C@@H](O)[C@@H]1O] | ¹H NMR (400 MHz, MeOH-d₄) δ 7.89 (s, 1H), 7.58 (s, 1H), 7.47-7.40 (m, 2H), 7.38-7.26 (m, 3H), 4.82 (s, 1H), 4.46-4.33 (m, 1H), 4.10-3.95 (m, 3H), 3.95-3.83 (m, 2H), 3.73 (dd, J = 11.6, 5.6 Hz, 1H), 3.65-3.50 (m, 3H), 2.15-1.93 (m, 4H). | 438.8 [M + H]⁺ |
| A53 | 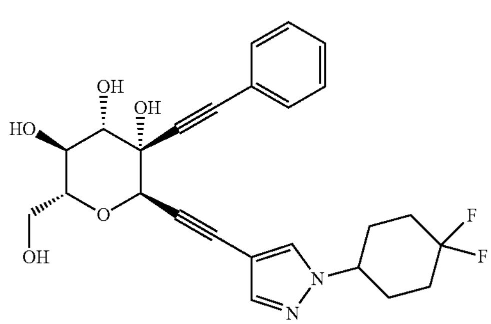 [SMILES: OC[C@H]1O[C@H](C#Cc2cnn(C3CCC(F)(F)CC3)c2)[C@](O)(C#Cc2ccccc2)[C@@H](O)[C@@H]1O] | | 473.0 [M + H]⁺ |

-continued

| Compound No. | Compound structure | ¹HNMR | Mass spectrum molecular weight |
|---|---|---|---|
| A54 | 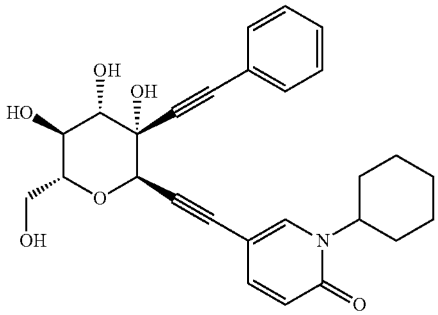 [SMILES: O=c1ccc(C#C[C@H]2O[C@H](CO)[C@@H](O)[C@H](O)[C@@]2(O)C#Cc2ccccc2)cn1C1CCCCC1] | | 463.8 [M + H]⁺ |
| A55 | 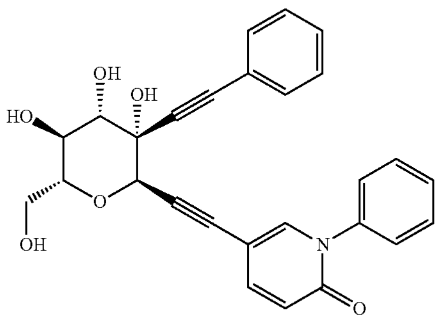 [SMILES: O=c1ccc(C#C[C@H]2O[C@H](CO)[C@@H](O)[C@H](O)[C@@]2(O)C#Cc2ccccc2)cn1-c1ccccc1] | | 457.7 [M + H]⁺ |
| A56 | 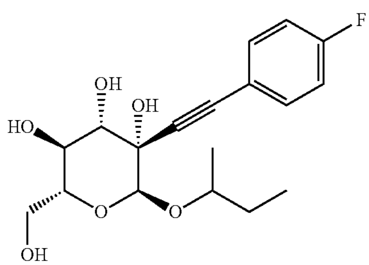 [SMILES: CCC(C)O[C@H]1O[C@H](CO)[C@@H](O)[C@H](O)[C@@]1(O)C#Cc1ccc(F)cc1] | ¹H NMR (400 MHz, MeOH-d₄) δ 7.47 (dd, J = 8.0, 5.6 Hz, 2H), 7.08 (dd, J = 8.4, 8.4 Hz, 2H), 4.85 (d, J = 4.8 Hz, 1H), 3.87-3.66 (m, 5H), 3.60 (dd, J = 8.8, 8.8 Hz, 1H), 1.71-1.49 (m, 2H), 1.30-1.18 (m, 3H), 1.04-0.92 (m, 3H). | |
| A57 | 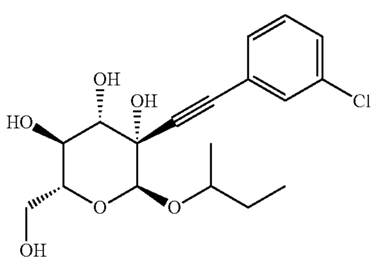 [SMILES: CCC(C)O[C@H]1O[C@H](CO)[C@@H](O)[C@H](O)[C@@]1(O)C#Cc1cccc(Cl)c1] | ¹H NMR (400 MHz, MeOH-d₄) δ 7.45 (s, 1H), 7.40-7.30 (m, 3H), 4.85 (s, 1H), 3.87-3.65 (m, 5H), 3.60 (dd, J = 9.2, 9.2 Hz, 1H), 1.71-1.49 (m, 2H), 1.29-1.15 (m, 3H), 1.02-0.92 (m, 3H). | |
| A58 | 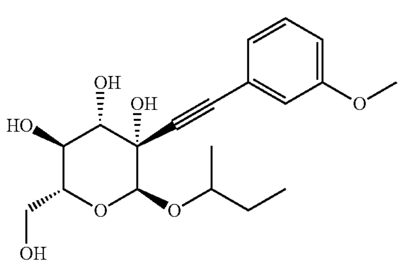 [SMILES: CCC(C)O[C@H]1O[C@H](CO)[C@@H](O)[C@H](O)[C@@]1(O)C#Cc1cccc(OC)c1] | ¹H NMR (400 MHz, MeOH-d₄) δ 7.23 (dd, J = 7.2, 7.2 Hz, 1H), 7.06-6.96 (m, 2H), 6.91 (d, J = 8.0 Hz, 1H), 4.85 (s, 1H), 3.90-3.66 (m, 8H), 3.60 (dd, J = 9.2, 9.2 Hz, 1H), 1.71-1.49 (m, 2H), 1.30-1.18 (m, 3H), 1.04-0.92 (m, 3H). | |

-continued

| Compound No. | Compound structure | ¹HNMR | Mass spectrum molecular weight |
|---|---|---|---|
| A59 | 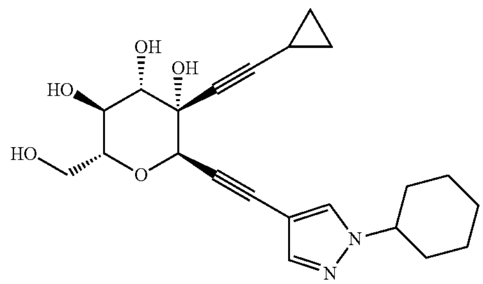 [SMILES: OC[C@H]1O[C@H](C#Cc2cnn(C3CCCCC3)c2)[C@](O)(C#CC2CC2)[C@@H](O)[C@@H]1O] | ¹H NMR (400 MHz, MeOH-d$_4$) δ 7.87 (s, 1H), 7.57 (s, 1H), 4.67 (s, 1H), 4.20-4.08 (m, 1H), 3.90-3.78 (m, 3H), 3.69 (dd, J = 11.2, 5.6 Hz, 1H), 3.51 (dd, J = 9.6, 9.6 Hz, 1H), 2.08 (d, J = 10.8 Hz, 2H), 1.90 (d, J = 12.4 Hz, 2H), 1.83-1.67 (m, 3H), 1.55-1.38 (m, 2H), 1.38-1.23 (m, 2H), 0.80-0.72 (m, 2H), 0.63 (s, 2H). | 400.9 [M+H]$^+$ |
| A60 | 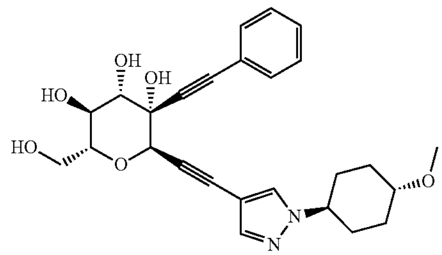 [SMILES: CO[C@H]1CC[C@H](n2cc(C#C[C@H]3O[C@H](CO)[C@@H](O)[C@H](O)[C@@]3(O)C#Cc3ccccc3)cn2)CC1] | ¹H NMR (400 MHz, MeOH-d$_4$) δ 7.85 (s, 1H), 7.55 (s, 1H), 7.47-7.38 (m, 2H), 7.37-7.27 (m, 3H), 4.81 (s, 1H), 4.25-4.08 (m, 1H), 3.98 (d, J = 8.8 Hz, 1H), 3.95-3.84 (m, 2H), 3.78-3.68 (m, 1H), 3.60 (dd, J = 8.8, 8.8 Hz, 1H), 3.37 (s, 3H), 2.25-2.05 (m, 4H), 1.90-1.76 (m, 2H), 1.47-1.28 (m, 2H). | 466.8 [M + H]$^+$ |
| A61 | 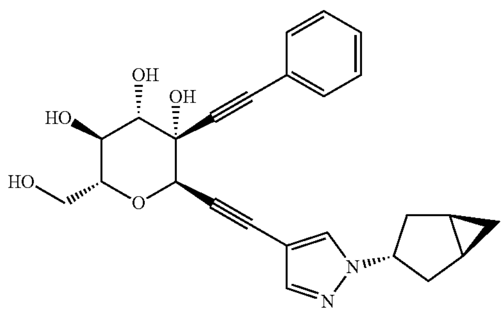 [SMILES: OC[C@H]1O[C@H](C#Cc2cnn([C@@H]3C[C@H]4C[C@H]4C3)c2)[C@](O)(C#Cc2ccccc2)[C@@H](O)[C@@H]1O] | ¹H NMR (400 MHz, MeOH-d$_4$) δ 7.81 (s, 1H), 7.55 (s, 1H), 7.42 (d, J = 7.2 Hz, 2H), 7.37-7.27 (m, 3H), 4.81 (s, 1H), 4.43-4.30 (m, 1H), 3.99 (d, J = 9.2 Hz, 1H), 3.95-3.83 (m, 2H), 3.73 (dd, J = 11.6, 5.6 Hz, 1H), 3.60 (dd, J = 11.2, 11.2 Hz, 1H), 2.35-2.15 (m, 4H), 1.50-1.38 (m, 2H), 0.53-0.42 (m, 1H), 0.35-0.27 (m, 1H). | 434.9 [M + H]$^+$ |
| A62 | 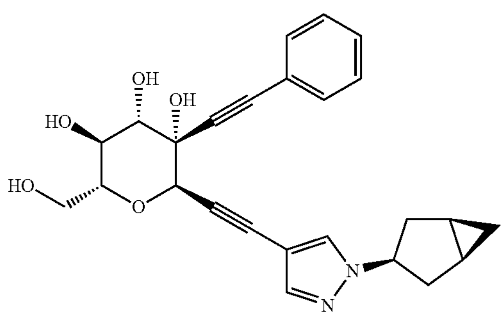 [SMILES: OC[C@H]1O[C@H](C#Cc2cnn([C@H]3C[C@H]4C[C@H]4C3)c2)[C@](O)(C#Cc2ccccc2)[C@@H](O)[C@@H]1O] | ¹H NMR (400 MHz, MeOH-d$_4$) δ 7.81 (s, 1H), 7.52 (s, 1H), 7.42 (d, J = 7.2 Hz, 2H), 7.37-7.27 (m, 3H), 4.81 (s, 1H), 3.99 (d, J = 8.8 Hz, 1H), 3.95-3.84 (m, 2H), 3.73 (dd, J = 11.2, 5.6 Hz, 1H), 3.60 (dd, J = 11.2, 11.2 Hz, 1H), 2.56-2.40 (m, 2H), 2.18-2.10 (m, 2H), 1.44-1.34 (m, 2H), 0.70-0.55 (m, 1H), 0.28-0.18 (m, 1H). | 434.7 [M + H]$^+$ |
| A63 | 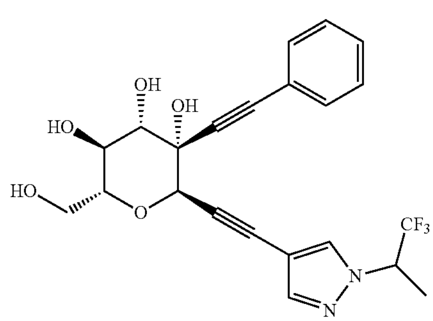 [SMILES: CC(n1cc(C#C[C@H]2O[C@H](CO)[C@@H](O)[C@H](O)[C@@]2(O)C#Cc2ccccc2)cn1)C(F)(F)F] | ¹H NMR (400 MHz, MeOH-d$_4$) δ 7.99 (s, 1H), 7.65 (s, 1H), 7.42 (d, J = 7.2 Hz, 2H), 7.37-7.27 (m, 3H), 5.20-5.10 (m, 1H), 4.81 (s, 1H), 3.99 (d, J = 9.2 Hz, 1H), 3.95-3.84 (m, 2H), 3.73 (dd, J = 11.2, 5.6 Hz, 1H), 3.61 (dd, J = 11.2, 11.2 Hz, 1H), 1.72 (d, J = 6.8 Hz, 3H). | 450.7 [M + H]$^+$ |

-continued

| Compound No. | Compound structure | ¹HNMR | Mass spectrum molecular weight |
|---|---|---|---|
| A64 | 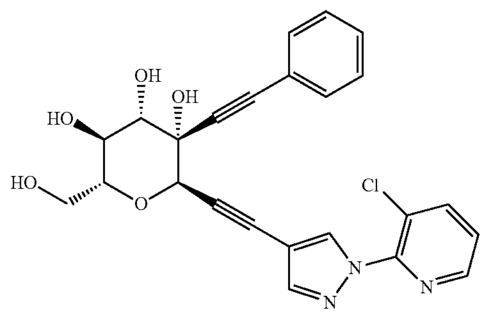 [SMILES: OC[C@H]1O[C@H](C#Cc2cnn(-c3ncccc3Cl)c2)[C@](O)(C#Cc2ccccc2)[C@@H](O)[C@@H]1O] | ¹H NMR (400 MHz, MeOH-d$_4$) δ 8.49 (d, J = 3.2 Hz, 1H), 8.39 (s, 1H), 8.12 (d, J = 8.0 Hz, 1H), 7.87 (s, 1H), 7.55-7.42 (m, 3H), 7.37-7.27 (m, 3H), 4.92 (s, 1H), 4.03 (d, J = 8.8 Hz, 1H), 4.00-3.92 (m, 1H), 3.91 (d, J = 12.0 Hz, 1H), 3.75 (dd, J = 11.6, 5.6 Hz, 1H), 3.62 (dd, J = 9.6, 9.6 Hz, 1H). | 466.1 [M + H]$^+$ |
| A65 | 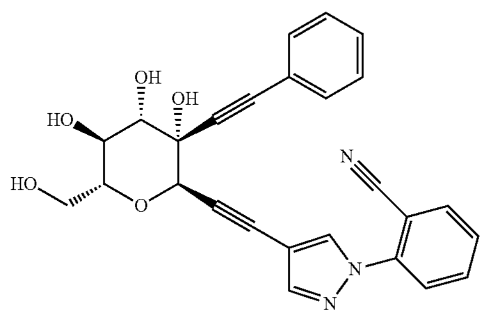 [SMILES: N#Cc1ccccc1-n1cc(C#C[C@H]2O[C@H](CO)[C@@H](O)[C@H](O)[C@@]2(O)C#Cc2ccccc2)cn1] | ¹H NMR (400 MHz, MeOH-d$_4$) δ 8.44 (s, 1H), 7.92 (d, J = 7.6 Hz, 1H), 7.89 (s, 1H), 7.83 (dd, J = 7.6, 7.6 Hz, 1H), 7.75 (d, J = 8.0 Hz, 1H), 7.60 (dd, J = 7.6, 7.6 Hz, 1H), 7.50-7.42 (m, 2H), 7.35-7.28 (m, 3H), 4.92 (s, 1H), 4.03 (d, J = 9.2 Hz, 1H), 4.00-3.92 (m, 1H), 3.90 (d, J = 11.6 Hz, 1H), 3.75 (dd, J = 12.0, 5.6 Hz, 1H), 3.62 (dd, J = 9.6, 9.6 Hz, 1H). | 478.1 [M + Na]$^+$ |
| A66 | 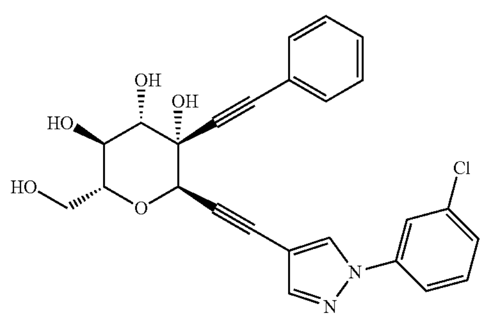 [SMILES: OC[C@H]1O[C@H](C#Cc2cnn(-c3cccc(Cl)c3)c2)[C@](O)(C#Cc2ccccc2)[C@@H](O)[C@@H]1O] | ¹H NMR (400 MHz, MeOH-d$_4$) δ 8.47 (s, 1H), 7.81 (s, 1H), 7.79 (s, 1H), 7.67 (d, J = 8.0 Hz, 1H), 7.50-7.41 (m, 3H), 7.36-7.28 (m, 4H), 4.92 (s, 1H), 4.03 (d, J = 8.8 Hz, 1H), 4.00-3.92 (m, 1H), 3.90 (d, J = 12.0 Hz, 1H), 3.76 (dd, J = 12.0, 5.6 Hz, 1H), 3.63 (dd, J = 9.6, 9.6 Hz, 1H). | 465.1 [M + H]$^+$ |
| A67 | 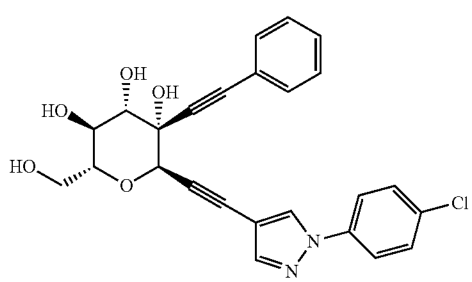 [SMILES: OC[C@H]1O[C@H](C#Cc2cnn(-c3ccc(Cl)cc3)c2)[C@](O)(C#Cc2ccccc2)[C@@H](O)[C@@H]1O] | ¹H NMR (400 MHz, MeOH-d$_4$) δ 8.44 (s, 1H), 7.78 (s, 1H), 7.43 (d, J = 8.4 Hz, 1H), 7.52-7.42 (m, 4H), 7.36-7.28 (m, 3H), 4.92 (s, 1H), 4.03 (d, J = 8.8 Hz, 1H), 4.00-3.92 (m, 1H), 3.90 (d, J = 12.0 Hz, 1H), 3.76 (dd, J = 12.0, 5.6 Hz, 1H), 3.63 (dd, J = 9.6, 9.6 Hz, 1H). | |
| A68 | 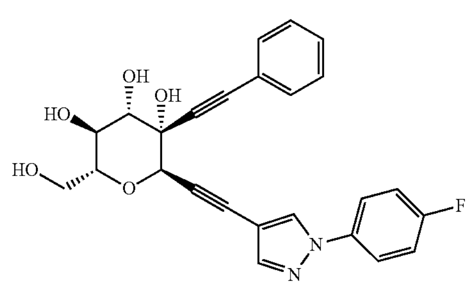 [SMILES: OC[C@H]1O[C@H](C#Cc2cnn(-c3ccc(F)cc3)c2)[C@](O)(C#Cc2ccccc2)[C@@H](O)[C@@H]1O] | ¹H NMR (400 MHz, MeOH-d$_4$) δ 8.40 (s, 1H), 7.78 (s, 1H), 7.74 (dd, J = 8.8, 4.0 Hz, 1H), 7.48-7.42 (m, 2H), 7.36-7.28 (m, 3H), 7.23 (dd, J = 8.8, 8.8 Hz, 1H), 4.92 (s, 1H), 4.02 (d, J = 8.8 Hz, 1H), 4.00-3.92 (m, 1H), 3.89 (d, J = 11.6 Hz, 1H), 3.75 (dd, J = 12.0, 5.6 Hz, 1H), 3.62 (dd, J = 9.6, 9.6 Hz, 1H). | 449.1 [M + H]$^+$ |

-continued

| Compound No. | Compound structure | ¹HNMR | Mass spectrum molecular weight |
|---|---|---|---|
| A69 | 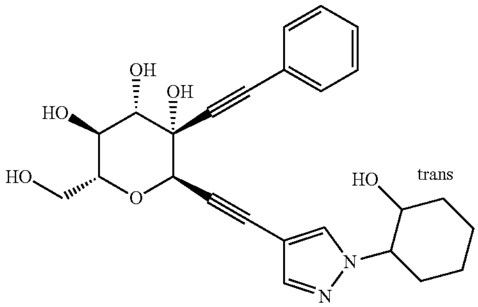 [SMILES: OC[C@H]1O[C@H](C#Cc2cnn(C3CCCCC3O)c2)[C@](O)(C#Cc2ccccc2)[C@@H](O)[C@@H]1O] | ¹H NMR (400 MHz, MeOH-d$_4$) δ 7.83 (s, 1H), 7.59 (s, 1H), 7.47-7.38 (m, 2H), 7.37-7.27 (m, 3H), 4.81 (s, 1H), 4.00 (d, J = 9.2 Hz, 1H), 3.97-3.84 (m, 3H), 3.84-2.72 (m, 3H), 3.61 (dd, J = 9.2, 9.2 Hz, 1H), 2.15-1.93 (m, 2H), 1.93-1.70 (m, 3H), 1.50-1.33 (m, 3H). | 452.7 [M + H] |
| A70 | 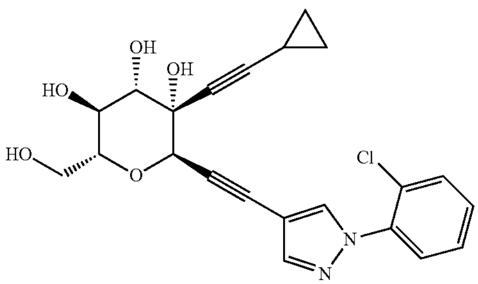 [SMILES: OC[C@H]1O[C@H](C#Cc2cnn(-c3ccccc3Cl)c2)[C@](O)(C#CC2CC2)[C@@H](O)[C@@H]1O] | ¹H NMR (400 MHz, MeOH-d$_4$) δ 8.20 (s, 1H), 7.85 (s, 1H), 7.69-7.54 (m, 2H), 7.54-7.45 (m, 2H), 4.72 (s, 1H), 3.93-3.80 (m, 3H), 3.71 (dd, J = 11.2, 5.6 Hz, 1H), 3.52 (dd, J = 9.6, 9.6 Hz, 1H), 1.36-1.30 (m, 1H), 0.83-0.75 (m, 2H), 0.66 (s, 2H). | 428.7 [M + H]$^+$ |
| A71 | 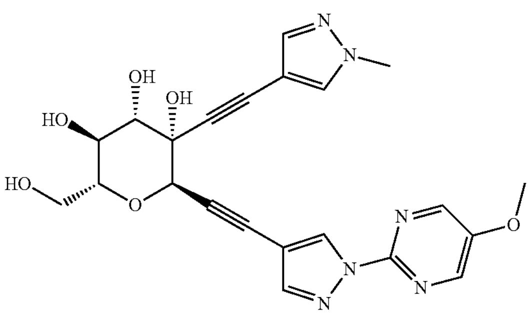 [SMILES: COc1cnc(-n2cc(C#C[C@H]3O[C@H](CO)[C@@H](O)[C@H](O)[C@@]3(O)C#Cc3cnn(C)c3)cn2)nc1] | ¹H NMR (400 MHz, DMSO-d$_6$ + D2O) δ 8.71 (s, 1H), 8.57 (s, 2H), 7.91 (s, 1H), 7.86 (s, 1H), 7.45 (s, 1H), 4.74 (s, 1H), 3.93 (s, 3H), 3.76 (s, 3H), 3.68-3.63 (m, 3H), 3.47 (dd, J = 11.6, 6.4 Hz, 1H), 3.34 (dd, J = 9.2, 9.2 Hz, 1H). | 467.1 [M + H]$^+$ |
| A72 | 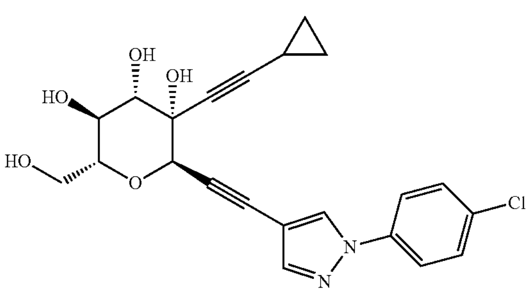 [SMILES: OC[C@H]1O[C@H](C#Cc2cnn(-c3ccc(Cl)cc3)c2)[C@](O)(C#CC2CC2)[C@@H](O)[C@@H]1O] | ¹H NMR (400 MHz, MeOH-d$_4$) δ 8.48 (s, 1H), 7.81 (s, 1H), 7.78 (d, J = 8.0 Hz, 2H), 7.51 (d, J = 8.0 Hz, 2H), 4.72 (s, 1H), 3.93-3.80 (m, 3H), 3.71 (dd, J = 11.2, 5.6 Hz, 1H), 3.53 (dd, J = 9.6, 9.6 Hz, 1H), 1.36-1.25 (m, 1H), 0.83-0.75 (m, 2H), 0.66 (s, 2H). | 428.7 [M + H]$^+$ |
| A73 | 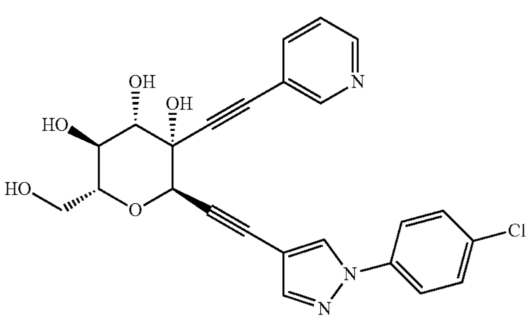 [SMILES: OC[C@H]1O[C@H](C#Cc2cnn(-c3ccc(Cl)cc3)c2)[C@](O)(C#Cc2cccnc2)[C@@H](O)[C@@H]1O] | | 465.7 [M + H]$^+$ |

| Compound No. | Compound structure | ¹HNMR | Mass spectrum molecular weight |
|---|---|---|---|
| A74 | 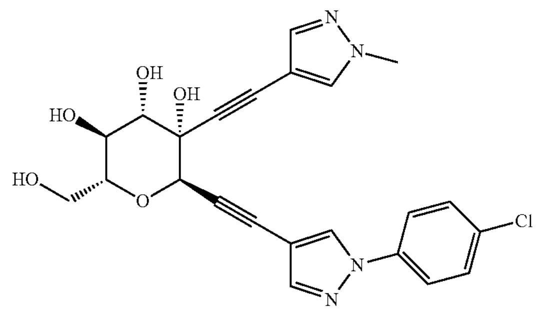 [SMILES: Cn1cc(C#C[C@@]2(O)[C@@H](C#Cc3cnn(-c4ccc(Cl)cc4)c3)O[C@H](CO)[C@@H](O)[C@@H]2O)cn1] | ¹H NMR (400 MHz, MeOH-d$_4$) δ 8.46 (s, 1H), 7.84-7.72 (m, 4H), 7.56 (s, 1H), 7.49 (d, J = 8.0 Hz, 2H), 4.81 (s, 1H), 4.20-4.10 (m, 2H), 4.00-3.86 (m, 3H), 3.74 (dd, J = 12.0, 5.6 Hz, 1H), 3.61 (dd, J = 9.2, 9.2 Hz, 1H), 1.36-1.25 (m, 1H), 0.83-0.75 (m, 2H), 0.66 (s, 2H). | 468.7 [M + H]⁺ |
| A75 | 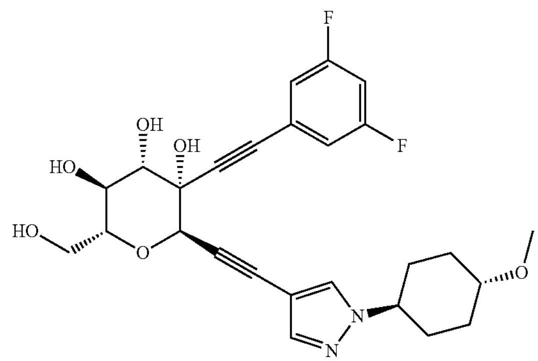 [SMILES: CO[C@H]1CC[C@H](n2cc(C#C[C@H]3O[C@H](CO)[C@@H](O)[C@H](O)[C@@]3(O)C#Cc3cc(F)cc(F)c3)cn2)CC1] | ¹H NMR (400 MHz, MeOH-d$_4$) δ 7.89 (s, 1H), 7.57 (s, 1H), 7.06-6.94 (m, 2H), 4.81 (s, 1H), 4.17 (dd, J = 7.6, 7.6 Hz, 1H), 3.98 (d, J = 9.2 Hz, 1H), 3.95-3.84 (m, 2H), 3.73 (dd, J = 11.2, 5.6 Hz, 1H), 3.60 (dd, J = 11.2, 11.2 Hz, 1H), 3.37 (s, 3H), 2.26-2.06 (m, 4H), 1.90-1.76 (m, 2H), 1.46-1.30 (m, 2H). | 502.7 [M + H]⁺ |
| A76 | 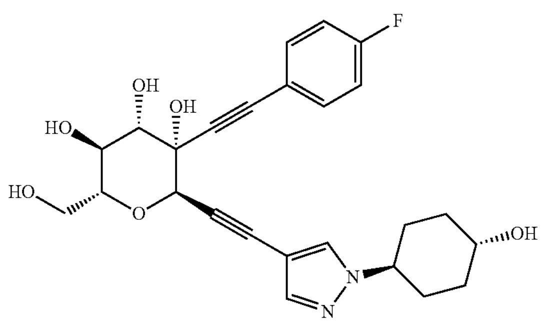 [SMILES: OC[C@H]1O[C@H](C#Cc2cnn([C@H]3CC[C@H](O)CC3)c2)[C@](O)(C#Cc2ccc(F)cc2)[C@@H](O)[C@@H]1O] | ¹H NMR (400 MHz, MeOH-d$_4$) δ 7.85 (s, 1H), 7.55 (s, 1H), 7.50-7.42 (m, 2H), 7.06 (dd, J = 8.4, 8.4 Hz, 2H), 4.81 (s, 1H), 4.14 (dd, J = 8.0, 8.0 Hz, 1H), 3.98 (d, J = 8.8 Hz, 1H), 3.95-3.84 (m, 2H), 3.73 (dd, J = 11.2, 5.6 Hz, 1H), 3.68-3.55 (m, 2H), 2.15-1.98 (m, 4H), 1.90-1.76 (m, 2H), 1.52-1.36 (m, 2H). | 470.8 [M + H]⁺ |
| A77 | 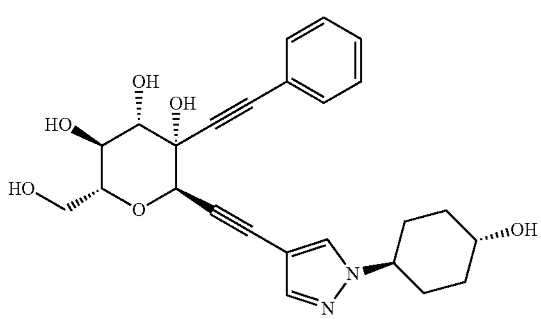 [SMILES: OC[C@H]1O[C@H](C#Cc2cnn([C@H]3CC[C@H](O)CC3)c2)[C@](O)(C#Cc2ccccc2)[C@@H](O)[C@@H]1O] | ¹H NMR (400 MHz, MeOH-d$_4$) δ 7.84 (s, 1H), 7.55 (s, 1H), 7.47-7.38 (m, 2H), 7.37-7.27 (m, 3H), 4.81 (s, 1H), 4.14 (dd, J = 10.8, 10.8 Hz, 1H), 3.98 (d, J = 8.8 Hz, 1H), 3.95-3.84 (m, 2H), 3.73 (dd, J = 11.2, 5.6 Hz, 1H), 3.68-3.55 (m, 2H), 2.15-1.98 (m, 4H), 1.90-1.76 (m, 2H), 1.52-1.36 (m, 2H). | 452.8 [M + H]⁺ |

-continued

| Compound No. | Compound structure | ¹HNMR | Mass spectrum molecular weight |
|---|---|---|---|
| A78 | 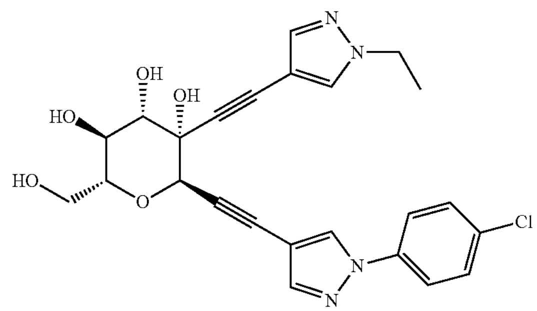 [SMILES: CCn1cc(C#C[C@@]2(O)[C@@H](C#Cc3cnn(-c4ccc(Cl)cc4)c3)O[C@H](CO)[C@@H](O)[C@@H]2O)cn1] | ¹H NMR (400 MHz, MeOH-d₄) δ 8.45 (s, 1H), 7.84-7.72 (m, 4H), 7.56 (s, 1H), 7.49 (d, J = 8.0 Hz, 2H), 4.81 (s, 1H), 4.20-4.10 (m, 2H), 4.00-3.86 (m, 3H), 3.74 (dd, J = 12.0, 5.6 Hz, 1H), 3.61 (dd, J = 9.2, 9.2 Hz, 1H), 1.40 (t, J = 7.2 Hz, 3H). | 483.1 [M + H]⁺ |
| A79 | 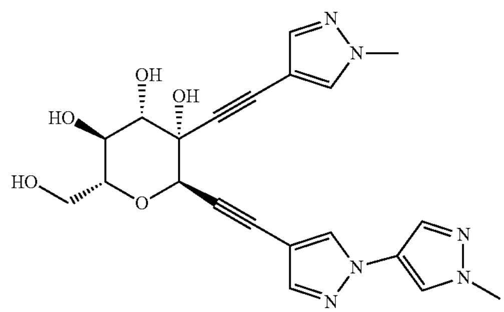 [SMILES: Cn1cc(C#C[C@@]2(O)[C@@H](C#Cc3cnn(-c4cnn(C)c4)c3)O[C@H](CO)[C@@H](O)[C@@H]2O)cn1] | ¹H NMR (400 MHz, DMSO-d₆ + D₂O) δ 8.38 (s, 1H), 8.10 (s, 1H), 7.85 (s, 1H), 7.79 (s, 1H), 7.76 (s, 1H), 7.48 (s, 1H), 4.72 (s, 1H), 3.83 (s, 6H), 3.70-3.62 (m, 3H), 3.46 (dd, J = 11.6, 6.4 Hz, 1H), 3.34 (dd, J = 9.2, 9.2 Hz, 1H). | 439.2 [M + H]⁺ |
| A80 | 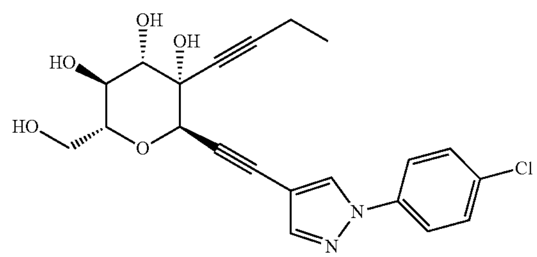 [SMILES: CCC#C[C@@]1(O)[C@@H](C#Cc2cnn(-c3ccc(Cl)cc3)c2)O[C@H](CO)[C@@H](O)[C@@H]1O] | ¹H NMR (400 MHz, MeOH-d₄) δ 8.48 (s, 1H), 7.81 (s, 1H), 7.77 (d, J = 8.4 Hz, 2H), 7.50 (d, J = 8.4 Hz, 2H), 4.75 (s, 1H), 3.94-3.80 (m, 3H), 3.72 (dd, J = 11.6, 5.6 Hz, 1H), 3.55 (dd, J = 9.2, 9.2 Hz, 1H), 2.26 (q, J = 7.2 Hz, 2H), 1.14 (t, J = 7.2 Hz, 3H). | 417.1 [M + H]⁺ |
| A81 | 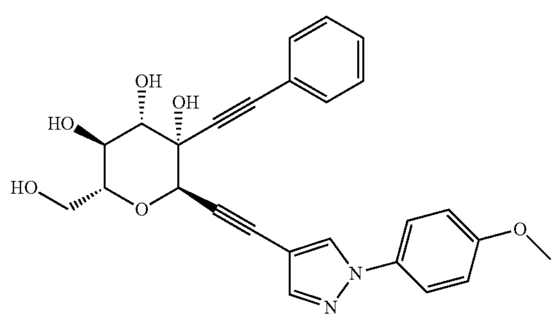 [SMILES: COc1ccc(-n2cc(C#C[C@H]3O[C@H](CO)[C@@H](O)[C@H](O)[C@@]3(O)C#Cc3ccccc3)cn2)cc1] | ¹H NMR (400 MHz, MeOH-d₄) δ 8.31 (s, 1H), 7.75 (s, 1H), 7.62 (d, J = 8.8 Hz, 2H), 7.50-7.42 (m, 2H), 7.38-7.28 (m, 3H), 7.08-6.98 (m, 2H), 4.85 (s, 1H), 4.05-3.80 (m, 7H), 3.79-3.70 (m, 1H), 3.62 (dd, J = 9.2, 9.2 Hz, 1H). | 461.2 [M + H]⁺ |
| A82 | 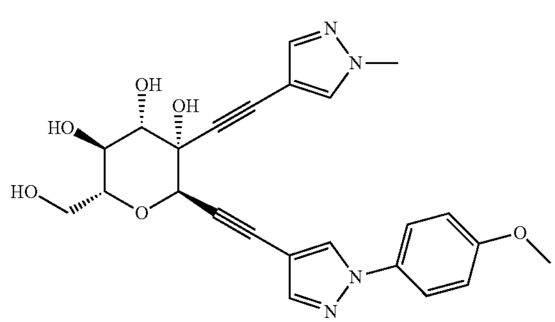 [SMILES: COc1ccc(-n2cc(C#C[C@H]3O[C@H](CO)[C@@H](O)[C@H](O)[C@@]3(O)C#Cc3cnn(C)c3)cn2)cc1] | ¹H NMR (400 MHz, MeOH-d₄) δ 8.31 (s, 1H), 7.75 (s, 1H), 7.62 (d, J = 8.8 Hz, 2H), 7.55 (s, 1H), 7.03 (d, J = 8.8 Hz, 2H), 4.85 (s, 1H), 4.00-3.86 (m, 3H), 3.85 (s, 3H), 3.84 (s, 3H), 3.74 (dd, J = 11.6, 5.6 Hz, 1H), 3.60 (dd, J = 9.6, 9.6 Hz, 1H). | 465.2 [M + H]⁺ |

-continued

| Compound No. | Compound structure | ¹HNMR | Mass spectrum molecular weight |
|---|---|---|---|
| A83 | 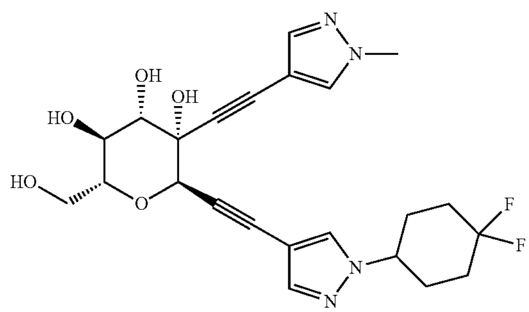 [SMILES: Cn1cc(C#C[C@@]2(O)[C@@H](C#Cc3cnn(C4CCC(F)(F)CC4)c3)O[C@H](CO)[C@@H](O)[C@@H]2O)cn1] | ¹H NMR (400 MHz, MeOH-d₄) δ 7.88 (s, 1H), 7.34 (s, 1H), 7.56 (s, 1H), 7.52 (s, 1H), 4.81 (s, 1H), 4.40-4.27 (m, 1H), 4.00-3.80 (m, 5H), 3.77-3.65 (m, 1H), 3.58 (dd, J = 11.2, 11.2 Hz, 1H), 2.25-1.88 (m, 8H). | 477.2 [M + H]⁺ |
| A84 | 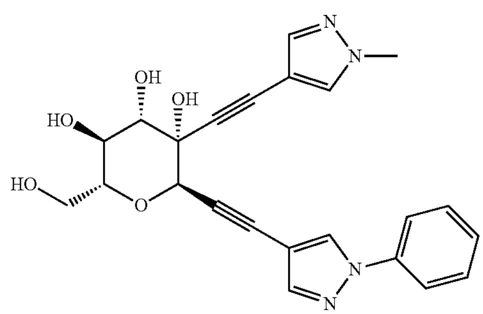 [SMILES: Cn1cc(C#C[C@@]2(O)[C@@H](C#Cc3cnn(-c4ccccc4)c3)O[C@H](CO)[C@@H](O)[C@@H]2O)cn1] | ¹H NMR (400 MHz, MeOH-d₄) δ 8.44 (s, 1H), 7.79 (s, 1H), 7.77-7.70 (m, 3H), 7.55 (s, 1H), 7.53-7.45 (m, 2H), 7.39-7.30 (m, 1H), 4.81 (s, 1H), 4.02-3.91 (m, 2H), 3.91-3.80 (m, 4H), 3.78-3.70 (m, 1H), 3.61 (dd, J = 11.2, 11.2 Hz, 1H). | 435.1 [M + H]⁺ |
| A85 | 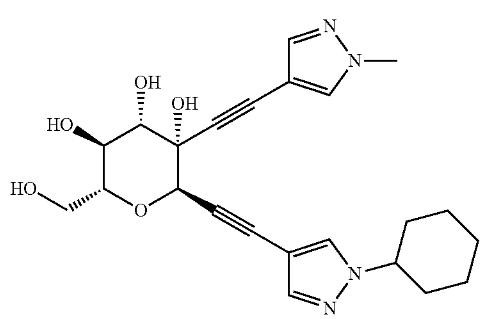 [SMILES: Cn1cc(C#C[C@@]2(O)[C@@H](C#Cc3cnn(C4CCCCC4)c3)O[C@H](CO)[C@@H](O)[C@@H]2O)cn1] | ¹H NMR (400 MHz, MeOH-d₄) δ 7.85 (s, 1H), 7.74 (s, 1H), 7.54 (s, 1H), 7.52 (s, 1H), 4.81 (s, 1H), 4.20-4.05 (m, 1H), 4.00-3.80 (m, 6H), 3.77-3.65 (m, 1H), 3.58 (dd, J = 11.2, 11.2 Hz, 1H), 2.07 (d, J = 11.6 Hz, 2H), 1.89 (d, J = 11.6 Hz, 2H), 1.80-1.66 (m, 3H), 1.54-1.38 (m, 2H), 1.37-1.24 (m, 1H). | 441.2 [M + H]⁺ |
| A86 | 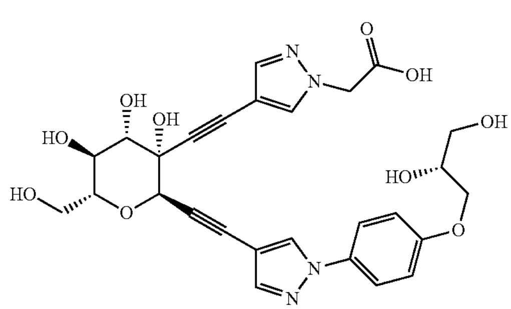 [SMILES: O=C(O)Cn1cc(C#C[C@@]2(O)[C@@H](C#Cc3cnn(-c4ccc(OC[C@H](O)CO)cc4)c3)O[C@H](CO)[C@@H](O)[C@@H]2O)cn1] | | 443.1 [M + H]⁺ |
| A87 | 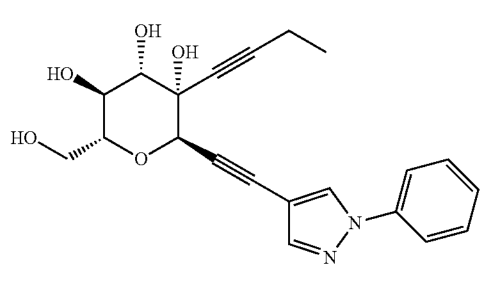 [SMILES: CCC#C[C@@]1(O)[C@@H](C#Cc2cnn(-c3ccccc3)c2)O[C@H](CO)[C@@H](O)[C@@H]1O] | ¹H NMR (400 MHz, MeOH-d₄) δ 8.46 (s, 1H), 7.80 (s, 1H), 7.76 (d, J = 7.6 Hz, 2H), 7.50 (dd, J = 7.6, 7.6 Hz, 2H), 7.36 (dd, J = 7.2, 7.2 Hz, 1H), 4.75 (s, 1H), 3.93-3.80 (m, 3H), 3.71 (dd, J = 12.0, 5.6 Hz, 1H), 3.55 (dd, J = 9.6, 9.6 Hz, 1H), 2.27 (q, J = 7.6 Hz, 2H), 1.14 (t, J = 7.6 Hz, 3H). | 382.8 [M + H]⁺ |

-continued

| Compound No. | Compound structure | ¹HNMR | Mass spectrum molecular weight |
|---|---|---|---|
| A88 | 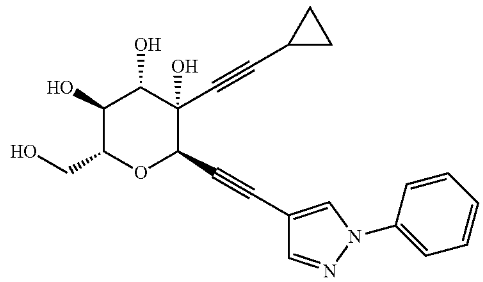 [SMILES: OC[C@H]1O[C@H](C#Cc2cnn(-c3ccccc3)c2)[C@](O)(C#CC2CC2)[C@@H](O)[C@@H]1O] | ¹H NMR (400 MHz, MeOH-$d_4$) δ 8.46 (s, 1H), 7.81 (s, 1H), 7.76 (d, J = 7.6 Hz, 2H), 7.50 (dd, J = 7.6, 7.6 Hz, 2H), 7.36 (dd, J = 7.2, 7.2 Hz, 1H), 4.72 (s, 1H), 3.93-3.80 (m, 3H), 3.71 (dd, J = 12.0, 5.6 Hz, 1H), 3.53 (dd, J = 9.6, 9.6 Hz, 1H), 1.40-1.23 (m, 1H), 0.83-0.75 (m, 2H), 0.66 (s, 2H). | 395.2 [M + H]$^+$ |
| A89 | 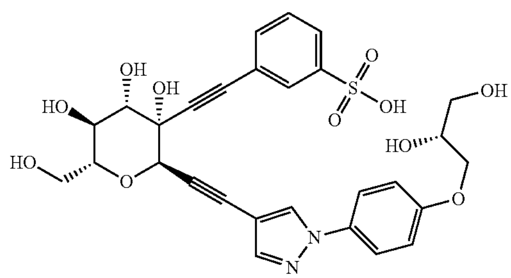 [SMILES: O=S(=O)(O)c1cccc(C#C[C@@]2(O)[C@@H](C#Cc3cnn(-c4ccc(OC[C@H](O)CO)cc4)c3)O[C@H](CO)[C@@H](O)[C@@H]2O)c1] | ¹H NMR (400 MHz, DMSO-$d_6$ + $D_2O$) δ 8.58 (s, 1H), 7.83 (s, 1H), 7.78-7.68 (m, 3H), 7.62-7.55 (m, 1H), 7.38-7.33 (m, 2H), 7.02 (d, J = 8.4 Hz, 2H), 4.81 (s, 1H), 4.05-3.97 (m, 2H), 3.92-3.84 (m, 2H), 3.70-3.64 (m, 1H), 3.52-3.40 (m, 4H), 3.36 (d, J = 9.2 Hz, 1H). | 459.1 [M − H]$^-$ |
| A90 | 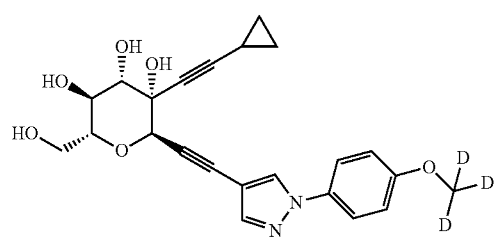 [SMILES: [2H]C([2H])([2H])Oc1ccc(-n2cc(C#C[C@H]3O[C@H](CO)[C@@H](O)[C@H](O)[C@@]3(O)C#CC3CC3)cn2)cc1] | ¹H NMR (400 MHz, DMSO-$d_6$ + $D_2O$) δ 8.64 (s, 1H), 7.73 (d, J = 7.6 Hz, 1H), 7.05 (d, J = 7.6 Hz, 1H), 4.60 (s, 1H), 3.78 (s, 1H), 3.72-3.68 (m, 2H), 3.43 (dd, J = 10.4, 6.0 Hz, 1H), 3.27 (dd, J = 9.2, 9.2 Hz, 1H), 1.33-1.23 (m, 1H), 0.77-0.68 (m, 2H), 0.53 (s, 2H). | 428.2 [M + H]$^+$ |
| A91 | 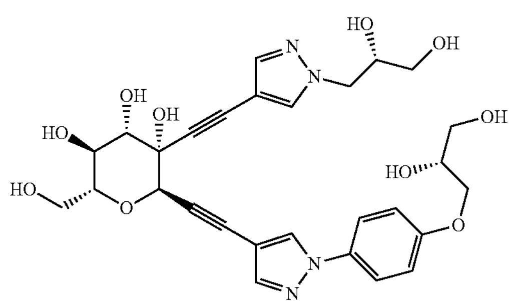 [SMILES: OC[C@@H](O)COc1ccc(-n2cc(C#C[C@H]3O[C@H](CO)[C@@H](O)[C@H](O)[C@@]3(O)C#Cc3cnn(C[C@H](O)CO)c3)cn2)cc1] | | 585.2 [M + H]$^+$ |
| A92 | 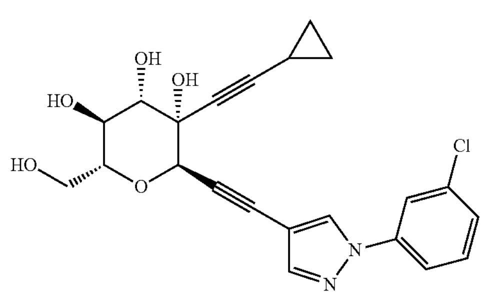 [SMILES: OC[C@H]1O[C@H](C#Cc2cnn(-c3cccc(Cl)c3)c2)[C@](O)(C#CC2CC2)[C@@H](O)[C@@H]1O] | ¹H NMR (400 MHz, MeOH-$d_4$) δ 8.52 (s, 1H), 7.87 (s, 1H), 7.82 (s, 1H), 7.73 (d, J = 8.0 Hz, 1H), 7.48 (dd, J = 8.4, 8.4 Hz, 1H), 7.36 (d, J = 8.0 Hz, 1H), 4.72 (s, 1H), 3.93-3.80 (m, 3H), 3.71 (dd, J = 12.0, 5.6 Hz, 1H), 3.54 (dd, J = 9.2, 9.2 Hz, 1H), 1.36-1.27 (m, 1H), 0.82-0.73 (m, 2H), 0.66 (s, 2H). | 451.1 [M + Na]$^+$ |

-continued

| Compound No. | Compound structure | ¹HNMR | Mass spectrum molecular weight |
|---|---|---|---|
| A93 | 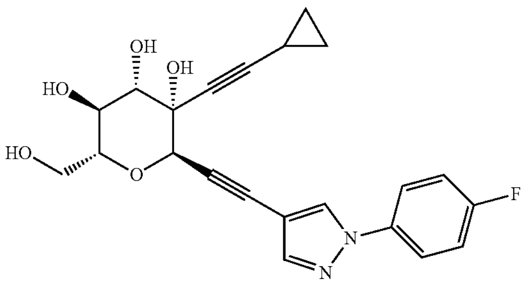 [SMILES: OC[C@H]1O[C@H](C#Cc2cnn(-c3ccc(F)cc3)c2)[C@](O)(C#CC2CC2)[C@@H](O)[C@@H]1O] | ¹H NMR (400 MHz, MeOH-d$_4$) δ 8.43 (s, 1H), 7.80 (s, 1H), 7.78 (dd, J = 4.0, 4.0 Hz, 2H), 7.25 (dd, J = 8.4, 8.4 Hz, 2H), 4.72 (s, 1H), 3.93-3.80 (m, 3H), 3.71 (dd, J = 12.0, 5.6 Hz, 1H), 3.54 (dd, J = 9.2, 9.2 Hz, 1H), 1.36-1.27 (m, 1H), 0.82-0.73 (m, 2H), 0.66 (s, 2H). | 413.1 [M + H]$^+$ |
| A94 | 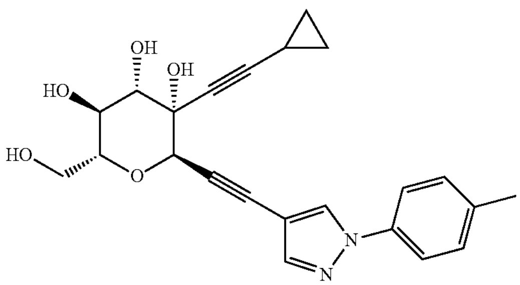 [SMILES: Cc1ccc(-n2cc(C#C[C@H]3O[C@H](CO)[C@@H](O)[C@H](O)[C@@]3(O)C#CC3CC3)cn2)cc1] | ¹H NMR (400 MHz, DMSO-d$_6$ + D$_2$O) δ 8.69 (s, 1H), 7.85 (s, 1H), 7.69 (d, J = 7.6 Hz, 2H), 7.30 (d, J = 8.0 Hz, 2H), 4.60 (s, 1H), 3.68-3.55 (m, 3H), 3.43 (dd, J = 11.2, 6.0 Hz, 1H), 3.27 (dd, J = 9.2, 9.2 Hz, 1H), 2.32 (s, 3H), 1.34-1.24 (m, 1H), 0.80-0.67 (m, 2H), 0.52 (s, 2H). | 409.2 [M + H]$^+$ |
| A95 | 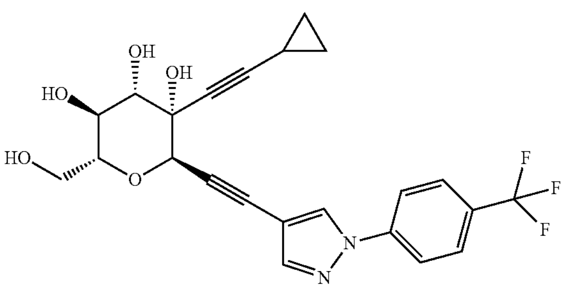 [SMILES: OC[C@H]1O[C@H](C#Cc2cnn(-c3ccc(C(F)(F)F)cc3)c2)[C@](O)(C#CC2CC2)[C@@H](O)[C@@H]1O] | ¹H NMR (400 MHz, MeOH-d$_4$) δ 8.61 (s, 1H), 8.01 (d, J = 8.4 Hz, 2H), 7.86 (s, 1H), 7.81 (d, J = 8.0 Hz, 2H), 4.72 (s, 1H), 3.93-3.80 (m, 3H), 3.71 (dd, J = 12.0, 5.6 Hz, 1H), 3.54 (dd, J = 9.6, 9.6 Hz, 1H), 1.36-1.27 (m, 1H), 0.82-0.73 (m, 2H), 0.66 (s, 2H). | 485.1 [M + Na]$^+$ |
| A96 | 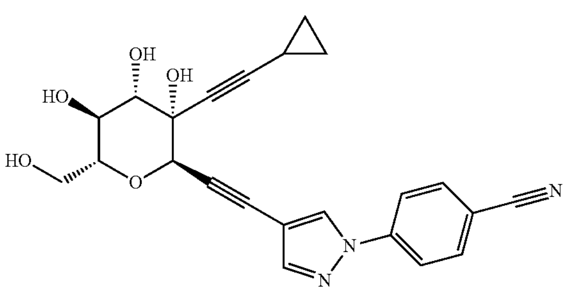 [SMILES: N#Cc1ccc(-n2cc(C#C[C@H]3O[C@H](CO)[C@@H](O)[C@H](O)[C@@]3(O)C#CC3CC3)cn2)cc1] | ¹H NMR (400 MHz, MeOH-d$_4$) δ 8.63 (s, 1H), 8.01 (J = 8.4 Hz, 2H), 7.86 (s, 1H), 7.87 (J = 8.4 Hz, 2H), 4.73 (s, 1H), 3.90-3.80 (m, 3H), 3.71 (dd, J = 12.0, 5.6 Hz, 1H), 3.54 (dd, J = 9.6, 9.6 Hz, 1H), 1.36-1.25 (m, 1H), 0.82-0.73 (m, 2H), 0.67 (s, 2H). | 442.1 [M + Na]$^+$ |
| A97 | 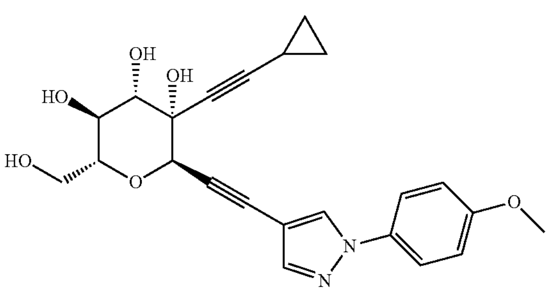 [SMILES: COc1ccc(-n2cc(C#C[C@H]3O[C@H](CO)[C@@H](O)[C@H](O)[C@@]3(O)C#CC3CC3)cn2)cc1] | ¹H NMR (400 MHz, DMSO-d$_6$ + D$_2$O) δ 8.66 (s, 1H), 7.83 (s, 1H), 7.74 (d, J = 8.8 Hz, 2H), 7.05 (d, J = 9.2 Hz, 2H), 4.61 (s, 1H), 3.79 (s, 3H), 3.67-3.56 (m, 3H), 3.43 (dd, J = 12.0, 6.0 Hz, 1H), 3.27 (dd, J = 9.6, 9.6 Hz, 1H), 1.36-1.25 (m, 1H), 0.77-0.68 (m, 2H), 0.57-0.50 (m, 2H). | 425.2 [M + H]$^+$ |

-continued

| Compound No. | Compound structure | ¹HNMR | Mass spectrum molecular weight |
|---|---|---|---|
| A98 | 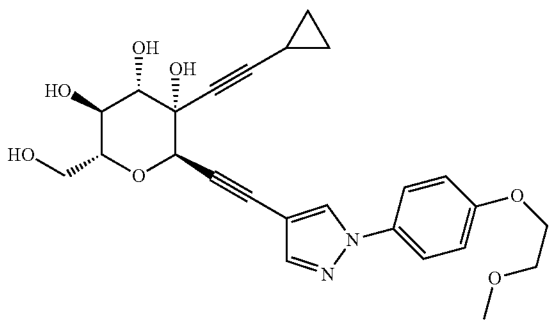 [SMILES: COCCOc1ccc(-n2cc(C#C[C@H]3O[C@H](CO)[C@@H](O)[C@H](O)[C@@]3(O)C#CC3CC3)cn2)cc1] | ¹H NMR (400 MHz, DMSO-d$_6$ + D$_2$O) δ 8.67 (s, 1H), 7.84 (s, 1H), 7.74 (d, J = 8.8 Hz, 2H), 7.07 (d, J = 9.2 Hz, 2H), 4.61 (s, 1H), 4.16-4.10 (m, 2H), 3.69-3.58 (m, 5H), 3.44 (dd, J = 11.6, 6.0 Hz, 1H), 3.31 (s, 1H), 3.28 (dd, J = 9.6, 9.6 Hz, 1H), 1.36-1.25 (m, 1H), 0.77-0.71 (m, 2H), 0.57-0.51 (m, 2H). | 469.2 [M + H]⁺ |
| A99 | 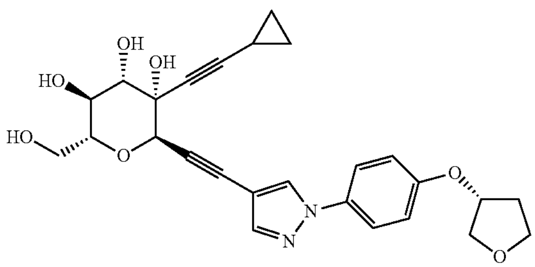 [SMILES: OC[C@H]1O[C@H](C#Cc2cnn(-c3ccc(O[C@@H]4CCOC4)cc3)c2)[C@](O)(C#CC2CC2)[C@@H](O)[C@@H]1O] | ¹H NMR (400 MHz, DMSO-d$_6$ + D$_2$O) δ 8.62 (s, 1H), 7.83 (s, 1H), 7.71 (d, J = 8.8 Hz, 2H), 7.03 (d, J = 8.8 Hz, 2H), 5.04 (s, 1H), 4.59 (s, 1H), 3.90-3.75 (m, 4H), 3.68-3.55 (m, 3H), 3.43 (dd, J = 12.0, 6.4 Hz, 1H), 3.27 (dd, J = 9.2, 9.2 Hz, 1H), 2.29-2.16 (m, 1H), 2.00-1.88 (m, 1H), 1.34-1.22 (m, 1H), 0.77-0.67 (m, 2H), 0.52 (s, 2H). | 481.2 [M + H]⁺ |
| A100 | 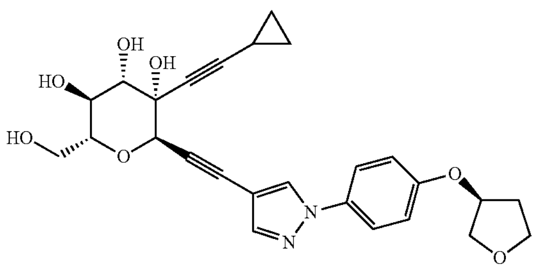 [SMILES: OC[C@H]1O[C@H](C#Cc2cnn(-c3ccc(O[C@H]4CCOC4)cc3)c2)[C@](O)(C#CC2CC2)[C@@H](O)[C@@H]1O] | ¹H NMR (400 MHz, DMSO-d$_6$ + D$_2$O) δ 8.60 (s, 1H), 7.83 (s, 1H), 7.77-7.61 (m, 2H), 7.03 (d, J = 7.2 Hz, 2H), 5.03 (s, 1H), 4.56 (s, 1H), 3.80-3.70 (m, 4H), 3.68-3.55 (m, 3H), 3.50-3.38 (m, 1H), 3.27 (dd, J = 9.2, 9.2 Hz, 1H), 2.28-2.15 (m, 1H), 2.00-1.88 (m, 1H), 1.32-1.22 (m, 1H), 0.80-0.65 (m, 2H), 0.52 (s, 2H). | 481.2 [M + H]⁺ |
| A101 | 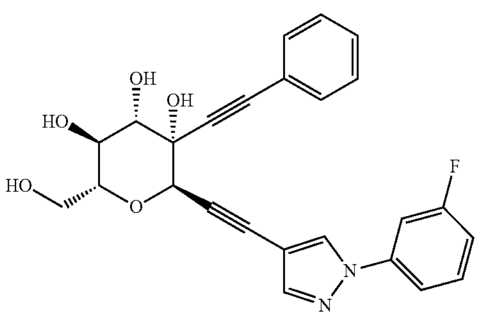 [SMILES: OC[C@H]1O[C@H](C#Cc2cnn(-c3cccc(F)c3)c2)[C@](O)(C#Cc2ccccc2)[C@@H](O)[C@@H]1O] | ¹H NMR (400 MHz, MeOH-d$_4$) δ 8.49 (s, 1H), 7.79 (s, 1H), 7.61-7.54 (m, 2H), 7.54-7.42 (m, 3H), 7.36-7.28 (m, 3H), 7.08 (dd, J = 8.0, 8.0 Hz, 1H), 4.91 (s, 1H), 4.02 (d, J = 8.8 Hz, 1H), 3.98-3.91 (m, 1H), 3.89 (d, J = 12.0 Hz, 1H), 3.76 (dd, J = 12.0, 9.6 Hz, 1H), 3.64 (dd, J = 9.6, 9.6 Hz, 1H). | 471.1 [M + Na]⁺ |
| A102 | 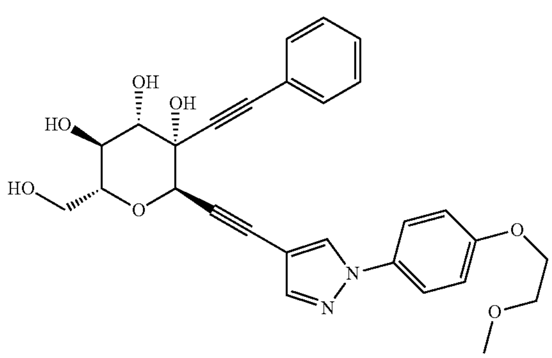 [SMILES: COCCOc1ccc(-n2cc(C#C[C@H]3O[C@H](CO)[C@@H](O)[C@H](O)[C@@]3(O)C#Cc3ccccc3)cn2)cc1] | ¹H NMR (400 MHz, MeOH-d$_4$) δ 8.30 (s, 1H), 7.75 (s, 1H), 7.61 (d, J = 8.8 Hz, 2H), 7.48-7.42 (m, 2H), 7.36-7.28 (m, 3H), 7.05 (d, J = 8.8 Hz, 2H), 4.91 (s, 1H), 4.20-4.13 (m, 2H), 4.02 (d, J = 8.8 Hz, 1H), 3.99-3.92 (m, 1H), 3.89 (d, J = 12.0 Hz, 1H), 3.80-3.71 (m, 3H), 3.62 (dd, J = 9.6, 9.6 Hz, 1H), 3.43 (s, 3H). | 505.2 [M + H]⁺ |

-continued

| Compound No. | Compound structure | ¹HNMR | Mass spectrum molecular weight |
|---|---|---|---|
| A103 | 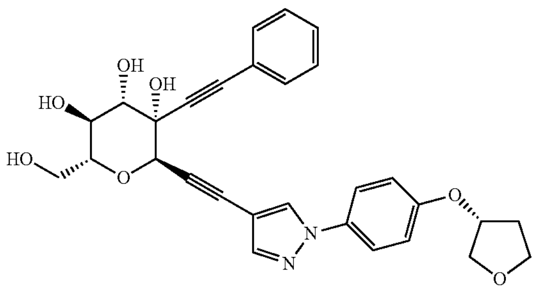 [SMILES: OC[C@H]1O[C@H](C#Cc2cnn(-c3ccc(O[C@@H]4CCOC4)cc3)c2)[C@](O)(C#Cc2ccccc2)[C@@H](O)[C@@H]1O] | ¹H NMR (400 MHz, MeOH-d₄) δ 8.31 (s, 1H), 7.75 (s, 1H), 7.63 (d, J = 8.8 Hz, 2H), 7.50-7.42 (m, 2H), 7.36-7.28 (m, 3H), 7.02 (d, J = 8.8 Hz, 2H), 5.06 (s, 1H), 4.92-4.88 (m, 1H), 4.04-3.84 (m, 6H), 3.79-3.71 (m, 1H), 3.52 (dd, J = 9.6, 9.6 Hz, 1H), 2.34-2.22 (m, 1H), 2.18-2.06 (m, 1H). | 517.2 [M + H]⁺ |
| A104 | 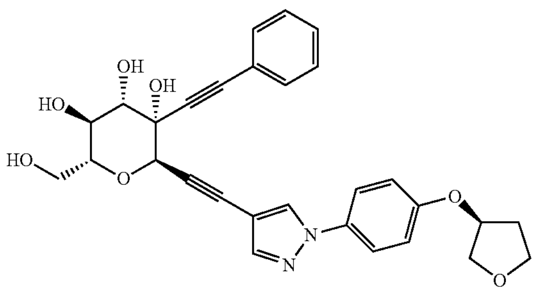 [SMILES: OC[C@H]1O[C@H](C#Cc2cnn(-c3ccc(O[C@H]4CCOC4)cc3)c2)[C@](O)(C#Cc2ccccc2)[C@@H](O)[C@@H]1O] | ¹H NMR (400 MHz, MeOH-d₄) δ 8.31 (s, 1H), 7.75 (s, 1H), 7.62 (d, J = 8.4 Hz, 2H), 7.50-7.42 (m, 2H), 7.36-7.28 (m, 3H), 7.02 (d, J = 8.8 Hz, 2H), 5.06 (s, 1H), 4.92-4.88 (m, 1H), 4.06-3.80 (m, 6H), 3.79-3.71 (m, 1H), 3.66-3.58 (m, 1H), 2.34-2.22 (m, 1H), 2.18-2.06 (m, 1H). | 517.2 [M + H]⁺ |
| A105 | 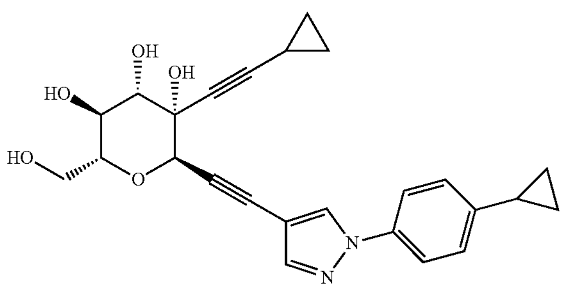 [SMILES: OC[C@H]1O[C@H](C#Cc2cnn(-c3ccc(C4CC4)cc3)c2)[C@](O)(C#CC2CC2)[C@@H](O)[C@@H]1O] | ¹H NMR (400 MHz, DMSO-d₆ + D₂O) δ 8.59 (s, 1H), 7.85 (s, 1H), 7.68 (d, J = 5.6 Hz, 2H), 7.19 (d, J = 7.2 Hz, 2H), 4.60 (s, 1H), 4.04 (q, J = 6.8 Hz, 2H), 3.60-3.48 (m, 3H), 3.47-3.38 (m, 1H), 3.27 (dd, J = 9.6, 9.6 Hz, 1H), 2.00-1.90 (m, 1H), 1.34-1.22 (m, 1H), 0.96 (d, J = 6.8 Hz, 2H), 0.78-0.60 (m, 4H). | 435.2 [M + H]⁺ |
| A106 | 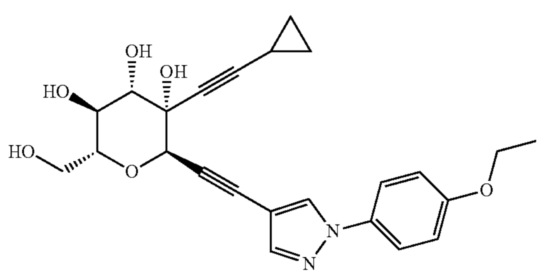 [SMILES: CCOc1ccc(-n2cc(C#C[C@H]3O[C@H](CO)[C@@H](O)[C@H](O)[C@@]3(O)C#CC3CC3)cn2)cc1] | ¹H NMR (400 MHz, DMSO-d₆ + D₂O) δ 8.64 (s, 1H), 7.83 (s, 1H), 7.71 (d, J = 8.0 Hz, 2H), 7.03 (d, J = 8.4 Hz, 2H), 4.60 (s, 1H), 4.04 (q, J = 6.8 Hz, 2H), 3.72-3.60 (m, 3H), 3.43 (dd, J = 11.2, 6.4 Hz, 1H), 3.27 (dd, J = 9.2, 9.2 Hz, 1H), 1.32 (t, J = 6.4 Hz, 3H), 1.32-1.24 (m, 1H), 0.77-0.69 (m, 2H), 0.53 (s, 2H). | 439.2 [M + H]⁺ |
| A107 | 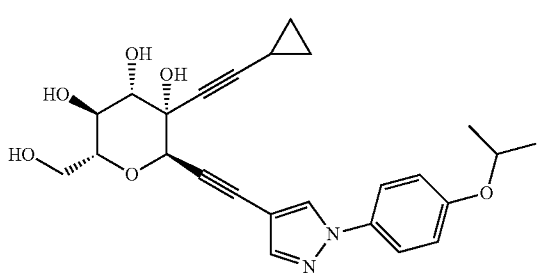 [SMILES: CC(C)Oc1ccc(-n2cc(C#C[C@H]3O[C@H](CO)[C@@H](O)[C@H](O)[C@@]3(O)C#CC3CC3)cn2)cc1] | ¹H NMR (400 MHz, DMSO-d₆ + D₂O) δ 8.63 (s, 1H), 7.83 (s, 1H), 7.70 (d, J = 7.6 Hz, 2H), 7.02 (d, J = 7.6 Hz, 2H), 4.68-4.58 (m, 1H), 4.60 (s, 1H), 3.70-3.57 (m, 3H), 3.44 (dd, J = 11.2, 6.8 Hz, 1H), 3.27 (dd, J = 9.6, 9.6 Hz, 1H), 1.33-1.22 (m, 7H), 0.77-0.69 (m, 2H), 0.53 (s, 2H). | 453.2 [M + H]⁺ |

Example 13

In the present example, the mannose derivatives A1 to A107 that were prepared in Examples 1 to 12 were analyzed in hemagglutination inhibition (HAI) assays to determine inhibitory effects of the compounds on the function/activity of FimH proteins.

1. Preparation of a guinea pig red blood cell solution: an adult guinea pig was anesthetized with ethyl ether, blood was sampled from the heart, placed in an EDTA blood collection tube, and centrifuged at 2,000 rpm for 5 min, serum was removed, the sample was transferred in a centrifuge tube (15 mL), sterilized PBS was added, the sample was centrifuged at 1,500 rpm for 10 min, a supernatant was removed, the sample was transferred in a centrifuge tube (50 mL), PBS was added, the sample was centrifuged at 1,500 rpm for 10 min and repeatedly washed twice, and red blood cells were slightly aspirated into a new centrifuge tube (50 mL) to obtain a 5% guinea pig red blood cell solution.

2. Preparation of a bacteria solution: a UPEC cell line UTI89 was inoculated on a medium plate and cultured in an incubator at 37° C. overnight. Single colonies were picked and inoculated in an LB medium in a sterilized conical flask, and cultured at 37° C. and 170 r/min overnight. When an OD value at 540 nm was about 0.8 on a microplate reader, the bacterial concentration was about $10^8$-$10^9$ cfu/mL, the bacteria solution was centrifuged at 2,000 rpm for 10 min, a supernatant was removed, and 1 mL of bacteria solution was prepared into 0.1 mL of PBS bacteria solution. 50 μL of PBS bacteria solution was placed in the first well of a 96-well V-shaped culture plate, 25 μL of PBS was placed in each of the second well to the twelfth well, the PBS bacteria solution and the medium in the first well were mixed, 25 μL of mixed solution was aspirated and placed in the second well, the bacteria solution was diluted in proportion in sequence to the twelfth well, 25 μL of bacteria solution was removed, the last row was reserved for negative controls that did not contain the bacteria and contained the red blood cells only. The bacteria and the medium were uniformly mixed by shaking, and reacted in an incubator at 25° C. for about 20-40 min. When the plate was read, the wells in which complete agglutination occurred were used as 4HAU for the hemagglutination titer of the bacteria. For example, if the endpoint titer of hemagglutination is 1:256, the dilution multiple of the 4HAU antigen is 1:64 (256 divided by 4). Bacteria solutions at corresponding concentrations were prepared according to the experimental results.

3. Activity assay: a compound to be tested or a standard product was placed in a 96-well microtest plate, 50 μL of drug at an initial concentration of 200 μM was placed in the first well, and from the second well, 25 μL of PBS was added to each well to dilute the drug in proportion. The drug and the medium in the first well were mixed, 25 μL of mixed drug solution was placed in the second well, the drug solution was diluted in sequence to the last well, and 25 μL of drug solution was removed. 25 μL of bacteria solution was placed in each well of the culture plate containing the diluted drug, and cultured at 37° C. for 40 min. 25 μL of 5% guinea pig red blood cell suspension was placed in each well, and slightly uniformly mixed with the drug, and the plate was placed at 4° C. for about 1 h. When results were determined, the plate was tilted 60°, and whether the red blood cells flowed like teardrops was observed.

Figure 2:
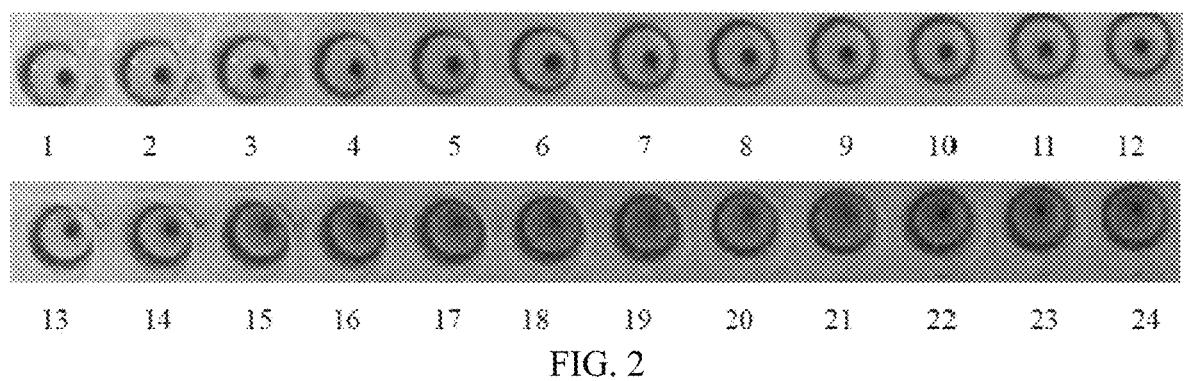
FIG. 2 is a diagram of an assay result of a compound A41.
Figure 3:
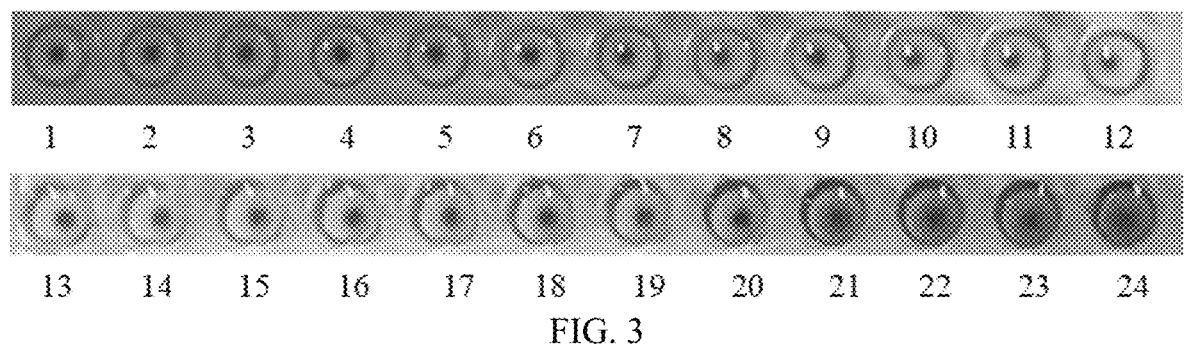
FIG. 3 is a diagram of an assay result of a compound A66.

Mannosyl proteins are expressed on the surface of red blood cells in a guinea pig, which can bind to FimH proteins of UTI89 to cause hemagglutination. It can be observed with the naked eyes that the red blood cells form film-like agglutination at the bottom of the well, and loose red dots can be seen in the center. The FimH protein inhibitor competitively binds to FimH proteins to inhibit hemagglutination. It can be observed with the naked eyes that all the red blood cells sink and concentrate at the bottom of the well to form dense dots. The minimum concentration for inhibiting hemagglutination is expressed as an $EC_{90}$ value of a compound. The final concentration of the compound in the first well is 66700 nM, the concentration in the second well is half that in the first well, the concentration in the third well is half that in the second well, and so on. The compounds A33, A41, and A66 are taken as examples, the minimum concentrations for inhibiting hemagglutination of A33 and A41 are concentrations of A33 and A41 in the fourteenth wells (see FIG. 1 and FIG. 2), and corresponding $EC_{90}$ values are 8 nM; the minimum concentration for inhibiting hemagglutination of A66 is a concentration of A66 in the twentieth well (see FIG. 3), and a corresponding $EC_{90}$ value is 0.13 nM. A low $EC_{90}$ value indicates high activity of a compound. HAI assay results of the compounds A1 to A107 are shown in Table 2.

TABLE 2

HAI assay results of 2-alkynylmannose derivatives A1 to A107

| Compound No. | HAI $EC_{90}$ (nM) | Compound No. | HAI $EC_{90}$ (nM) | Compound No. | HAI $EC_{90}$ (nM) |
|---|---|---|---|---|---|
| A1 | 8 | A2 | 16 | A3 | 16 |
| A4 | 1040 | A5 | 520 | A6 | 1040 |
| A7 | 260 | A8 | 260 | A9 | 130 |
| A10 | 0.13 | A11 | 520 | A12 | 260 |
| A13 | 1040 | A14 | 4160 | A15 | 520 |
| A16 | 130 | A17 | 130 | A18 | 260 |
| A19 | 520 | A20 | 260 | A21 | 260 |
| A22 | 130 | A23 | 260 | A24 | 260 |
| A25 | 260 | A26 | 130 | A27 | 130 |
| A28 | 260 | A29 | 520 | A30 | 1040 |
| A31 | <0.1 | A32 | 130 | A33 | 8 |
| A34 | 64 | A35 | 520 | A36 | 260 |
| A37 | 260 | A38 | 260 | A39 | 8 |
| A40 | 32 | A41 | 8 | A42 | 4 |
| A43 | 32 | A44 | 8 | A45 | 1 |
| A46 | 0.5 | A47 | 0.25 | A48 | 1 |
| A49 | 16 | A50 | 130 | A51 | 16 |
| A52 | 4 | A53 | 8 | A54 | 4 |
| A55 | 64 | A56 | 520 | A57 | 260 |
| A58 | 520 | A59 | 4 | A60 | 2 |
| A61 | 8 | A62 | 0.5 | A63 | 16 |
| A64 | 4 | A65 | 64 | A66 | 0.13 |
| A67 | 0.13 | A68 | 8 | A69 | 16 |
| A70 | 8 | A71 | 8 | A72 | <0.1 |
| A73 | 8 | A74 | 0.13 | A75 | 8 |
| A76 | 4 | A77 | 2 | A78 | <0.1 |
| A79 | 16 | A80 | 2 | A81 | <0.1 |
| A82 | <0.1 | A83 | 2 | A84 | 0.25 |
| A85 | 2 | A86 | 8 | A87 | 32 |
| A88 | 4 | A89 | 16 | A90 | <0.1 |
| A91 | 8 | A92 | 2 | A93 | 2 |
| A94 | <0.1 | A95 | 4 | A96 | 4 |
| A97 | <0.1 | A98 | <0.1 | A99 | <0.1 |
| A100 | <0.1 | A101 | 0.25 | A102 | <0.1 |
| A103 | <0.1 | A104 | <0.1 | A105 | 0.13 |
| A106 | <0.1 | A107 | <0.1 | | |

It can be seen from Table 2 that the mannose derivatives can effectively inhibit the function/activity of FimH proteins, and can be used for treating or preventing a disease or a disorder that is improved by inhibiting the function or activity of FimH proteins.

What is claimed is:

1. A 2-alkynylmannose derivative, a pharmaceutically acceptable salt or an isotope thereof, having a structure shown as formula I:

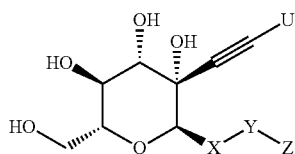

where,
U is a hydrogen atom, a deuterium atom, $C_{1-10}$ alkyl, $C_{3-10}$ cycloalkyl, $C_{2-10}$ alkenyl, $C_{2-10}$ alkynyl, a six- to ten-membered aromatic ring, a five- to ten-membered heteroaromatic ring that contains 1 to 4 heteroatoms selected from N, O, and S, or a five- to seven-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_1$ groups;
X is a chemical bond, an oxygen atom, a sulfur atom, $N(R_2)$, $C(R_2)(R_3)$ or —C≡C—;
Y is a chemical bond, $C_{1-10}$ alkyl, $C_{3-10}$ cycloalkyl, $C_{2-8}$ alkenyl, $C_{2-8}$ alkynyl, a six- to fourteen-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_4$ groups;
Z is selected from a hydrogen atom, a deuterium atom, a halogen, cyano, $C_{1-10}$ alkyl, $C_{3-10}$ cycloalkyl, $C_{1-10}$ alkoxy, $C_{2-8}$ alkenyl, $C_{2-8}$ alkynyl, —C(O)$OR_5$, —C(O)$NR_5R_6$, —N($R_5$)C(O)$R_6$, —S(O)$_2R_5$, —S(O)$_2$$NR_5R_6$, —P(O)$R_5R_6$, a six- to fourteen-membered aromatic ring, a five- to fourteen-membered heteroaromatic ring that contains 1 to 4 heteroatoms selected from N, O, and S, and a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 $R_7$ groups;
$R_1$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ureido, $C_{1-8}$ carbamato, $C_{1-8}$ sulfonamido, $C_{1-8}$ ester, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, and a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy;
$R_2$ and $R_3$ are each independently selected from a hydrogen atom, a deuterium atom, a halogen, hydroxyl, amino, $C_{1-8}$ alkyl, and $C_{3-8}$ cycloalkyl, and the alkyl and the cycloalkyl are unsubstituted or substituted with 1 to 3 substituent groups selected from a deuterium atom, a halogen, hydroxyl, $C_{1-3}$ alkyl, $C_{3-5}$ cycloalkyl, and $C_{1-3}$ alkoxy;
$R_4$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ureido, $C_{1-8}$ carbamato, $C_{1-8}$ sulfonamido, $C_{1-8}$ ester, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, and a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, $C_{1-3}$ alkoxy, and $C_{5-10}$ phenol;
$R_5$ and $R_6$ are each independently selected from a hydrogen atom, $C_{1-8}$ alkyl, and $C_{3-8}$ cycloalkyl, and the alkyl and the cycloalkyl are unsubstituted or substituted with 1 to 3 substituent groups selected from a deuterium atom, a halogen, hydroxyl, $C_{1-3}$ alkyl, $C_{3-5}$ cycloalkyl, and $C_{1-3}$ alkoxy; and
$R_7$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ureido, $C_{1-8}$ carbamato, $C_{1-8}$ sulfonamido, $C_{1-8}$ ester, dimethylphosphoryl, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, and a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

2. The 2-alkynylmannose derivative, a pharmaceutically acceptable salt, or an isotope thereof according to claim 1, wherein
U is a hydrogen atom, a deuterium atom, $C_{1-10}$ alkyl, $C_{3-10}$ cycloalkyl, a six- to ten-membered aromatic ring, a five- to ten-membered heteroaromatic ring that contains 1 to 4 heteroatoms selected from N, O, and S, or a five- to seven-membered heterocyclic ring that contains 1 or 2 heteroatoms selected from N, O, and S, and the alkyl, the cycloalkyl, the aromatic ring, the heteroaromatic ring, and the heterocyclic ring are unsubstituted or substituted with 1 to 5 $R_1$ groups;
X is an oxygen atom or —C≡C—;
Y is a chemical bound, $C_{1-10}$ alkyl, $C_{3-10}$ cycloalkyl, a six- to ten-membered aromatic ring, a five- to ten-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the aromatic ring, the heteroaromatic ring, and the heterocyclic ring are unsubstituted or substituted with 1 to 5 $R_4$ groups;
Z is selected from a hydrogen atom, a deuterium atom, a halogen, cyano, $C_{1-10}$ alkyl, $C_{3-10}$ cycloalkyl, $C_{1-10}$ alkoxy, $C_{2-8}$ alkenyl, $C_{2-8}$ alkynyl, —C(O)$OR_5$, —C(O)NR$_5$R$_6$, —N(R$_5$)C(O)R$_6$, —S(O)$_2$R$_5$, —S(O)$_2$NR$_5$R$_6$, —P(O)R$_5$R$_6$, a six- to ten-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 R$_7$ groups;

R$_1$ is selected from a hydrogen atom, a deuterium atom, a halogen, cyano, hydroxyl, amino, C$_{2-8}$ alkenyl, C$_{2-8}$ alkynyl, C$_{1-8}$ sulfonyl, C$_{1-8}$ amido, C$_{1-8}$ sulfonamido, C$_{1-8}$ ester, C$_{1-8}$ alkyl, C$_{3-8}$ cycloalkyl, C$_{1-8}$ alkoxy, phenyl, a five- or six-membered heteroaromatic ring that contains 1 to 3 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 to 3 substituent groups selected from a deuterium atom, a halogen, hydroxyl, cyano, C$_{1-3}$ alkyl, C$_{3-5}$ cycloalkyl, and C$_{1-3}$ alkoxy;

R$_4$ is selected from a hydrogen atom, a deuterium atom, a halogen, cyano, hydroxyl, amino, C$_{1-8}$ sulfonyl, C$_{1-8}$ alkyl, C$_{3-8}$ cycloalkyl, C$_{1-8}$ alkoxy, phenyl, a five- or six-membered heteroaromatic ring that contains 1 to 3 heteroatoms selected from N, O, and S, or a five- to seven-membered heterocyclic ring that contains 1 or 2 heteroatoms selected from N, O, and S, and the alkyl, the cycloalkyl, the alkoxy, the phenyl, the heteroaromatic ring, and the heterocyclic ring are unsubstituted or substituted with 1 to 3 substituent groups selected from a deuterium atoms, a halogen, hydroxyl, cyano, C$_{1-3}$ alkyl, C$_{3-5}$ cycloalkyl, C$_{1-3}$ alkoxy, and C$_{6-10}$ phenol;

R$_5$ and R$_6$ are each independently selected from a hydrogen atom, C$_{1-8}$ alkyl, and C$_{3-8}$ cycloalkyl, and the alkyl and the cycloalkyl are unsubstituted or substituted with 1 to 3 substituent groups selected from a deuterium atom, a halogen, hydroxyl, C$_{1-3}$ alkyl, C$_{3-5}$ cycloalkyl, and C$_{1-3}$ alkoxy; and R$_7$ is selected from a hydrogen atom, a deuterium atom, a halogen, cyano, hydroxyl, amino, C$_{2-8}$ alkenyl, C$_{2-8}$ alkynyl, C$_{1-8}$ sulfonyl, C$_{1-8}$ amido, C$_{1-8}$ ester, dimethylphosphoryl, C$_{1-8}$ alkyl, C$_{3-8}$ cycloalkyl, C$_{1-8}$ alkoxy, phenyl, a five- or six-membered heteroaromatic ring that contains 1 to 4 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 or 3 substituent groups selected from a deuterium atom, a halogen, hydroxyl, cyano, C$_{1-3}$ alkyl, C$_{3-5}$ cycloalkyl, and C$_{1-3}$ alkoxy.

3. The 2-alkynylmannose derivative, a pharmaceutically acceptable salt, or an isotope thereof according to claim 1, wherein
Y is C$_{1-8}$ alkyl, C$_{3-10}$ cycloalkyl, a six- to ten-membered aromatic ring, or a five- to ten-membered heteroaromatic ring that contains 1 to 4 heteroatoms selected from N, O, and S, and the alkyl, the cycloalkyl, the aromatic ring, and the heteroaromatic ring are unsubstituted or substituted with 1 to 5 R$_4$ groups; and R$_4$ is selected from a hydrogen atom, a deuterium atom, a halogen, cyano, hydroxyl, C$_{1-8}$ alkyl, C$_{3-8}$ cycloalkyl, and C$_{1-8}$ alkoxy, and the alkyl, the cycloalkyl, and the alkoxy are unsubstituted or substituted with 1 to 3 substituent groups selected from a deuterium atom, a halogen, hydroxyl, cyano, C$_{1-3}$ alkyl, C$_{3-5}$ cycloalkyl, and C$_{1-3}$ alkoxy.

4. The 2-alkynylmannose derivative, a pharmaceutically acceptable salt, or an isotope thereof according to claim 1, wherein
Y is selected from the following groups that are unsubstituted or substituted with 1 to 3 R$_4$ groups, the left side of Y is connected to X, the right side of Y is connected to Z, and the R$_4$ group is selected from a hydrogen atom, a deuterium atom, a halogen, cyano, hydroxyl, C$_{1-8}$ alkyl, C$_{3-8}$ cycloalkyl, and C$_{1-8}$ alkoxy, and the alkyl, the cycloalkyl, and the alkoxy are unsubstituted or substituted with 1 to 3 substituent groups selected from a deuterium atom, a halogen, hydroxyl, cyano, C$_{1-3}$ alkyl, C$_{3-5}$ cycloalkyl, and C$_{1-3}$ alkoxy.

5. The 2-alkynylmannose derivative, a pharmaceutically acceptable salt, or an isotope thereof according to claim 1, having a structure shown as formula Ia:

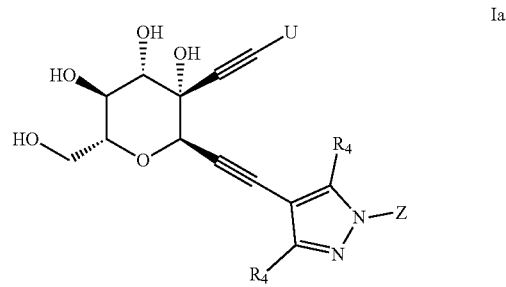

Ia where,
R$_4$ is selected from a hydrogen atom, a deuterium atom, a halogen, cyano, C$_{1-8}$ alkyl, C$_{3-8}$ cycloalkyl, and C$_{1-8}$ alkoxy, and the alkyl, the cycloalkyl, and the alkoxy are unsubstituted or substituted with 1 to 3 substituent groups selected from a deuterium atom, a halogen, hydroxyl, cyano, C$_{1-3}$ alkyl, C$_{3-5}$ cycloalkyl, and C$_{1-3}$ alkoxy;

U is a hydrogen atom, a deuterium atom, C$_{1-10}$ alkyl, C$_{3-10}$ cycloalkyl, a six- to ten-membered aromatic ring, a five- to ten-membered heteroaromatic ring that contains 1 to 4 heteroatoms selected from N, O, and S, or a five- to seven-membered heterocyclic ring that contains 1 or 2 heteroatoms selected from N, O, and S, and the alkyl, the cycloalkyl, the aromatic ring, the heteroaromatic ring, and the heterocyclic ring are unsubstituted or substituted with 1 to 5 R$_1$ groups; and Z is selected from a hydrogen atom, a deuterium atom, a halogen, cyano, C$_{1-10}$ alkyl, C$_{3-10}$ cycloalkyl, C$_{1-10}$ alkoxy, C$_{2-8}$ alkenyl, C$_{2-8}$ alkynyl, —C(O)OR$_5$, —C(O)NR$_5$R$_6$, —N(R$_5$)C(O)R$_6$, —S(O)$_2$R$_5$, —S(O)$_2$NR$_5$R$_6$, —P(O)R$_5$R$_6$, a six- to ten-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkenyl, the alkynyl, the aromatic ring, the heteroaromatic ring, and the heterocyclic ring are unsubstituted or substituted with 1 to 5 R$_7$ groups.

6. The 2-alkynylmannose derivative, a pharmaceutically acceptable salt, or an isotope thereof according to claim 1, wherein
U is $C_{1-10}$ alkyl, $C_{3-10}$ cycloalkyl, a six- to ten-membered aromatic ring, or a five- to ten-membered heteroaromatic ring that contains 1 to 4 heteroatoms selected from N, O, and S, and the alkyl, the cycloalkyl, the aromatic ring, and the heteroaromatic ring are unsubstituted or substituted with 1 to 5 $R_1$ groups; and
$R_1$ is selected from a hydrogen atom, a deuterium atom, a halogen, cyano, hydroxyl, amino, $C_{1-8}$ sulfonyl, $C_{1-8}$ amido, $C_{1-8}$ sulfonamido, $C_{1-8}$ ester, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

7. The 2-alkynylmannose derivative, a pharmaceutically acceptable salt, or an isotope thereof according to claim 1, wherein
U is selected from the following groups that are unsubstituted or substituted with 1 to 5 $R_1$ groups, and $R_1$ is selected from a hydrogen atom, a deuterium atom, a halogen, cyano, hydroxyl, amino, $C_{1-8}$ sulfonyl, $C_{1-8}$ amido, $C_{1-8}$ sulfonamido, $C_{1-8}$ ester, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

8. The 2-alkynylmannose derivative, a pharmaceutically acceptable salt, or an isotope thereof according to claim 1, wherein
Z is selected from a hydrogen atom, a deuterium atom, a halogen, cyano, $C_{1-10}$ alkyl, $C_{3-10}$ cycloalkyl, $C_{1-10}$ alkoxy, a six- to ten-membered aromatic ring, a five- to fourteen-membered heteroaromatic ring that contains 1 to 4 heteroatoms selected from N, O, and S, or a five- to ten-membered heterocyclic ring that contains 1 or 2 heteroatoms selected from N, O, and S, and the alkyl, the cycloalkyl, the alkoxy, the aromatic ring, the heteroaromatic ring, and the heterocyclic ring are unsubstituted or substituted with 1 to 5 $R_7$ groups; and
$R_7$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ester, dimethylphosphoryl, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 or 3 substituent groups selected from a deuterium atom, a halogen, hydroxyl, cyano, $C_{1-3}$ alkyl, $C_{3-5}$ cycloalkyl, and $C_{1-3}$ alkoxy.

9. The 2-alkynylmannose derivative, a pharmaceutically acceptable salt, or an isotope thereof according to claim 1, wherein
Z is selected from the following groups that are unsubstituted or substituted with 1 to 5 $R_7$ groups, and $R_7$ is selected from a hydrogen atom, a deuterium atom, a halogen, cyano, hydroxyl, amino, $C_{2-8}$ alkenyl, $C_{2-8}$ alkynyl, $C_{1-8}$ sulfonyl, $C_{1-8}$ amido, $C_{1-8}$ ester, dimethylphosphoryl, $C_{1-8}$ alkyl, $C_{3-8}$ cycloalkyl, $C_{1-8}$ alkoxy, phenyl, a five- or six-membered heteroaromatic ring that contains 1 to 4 heteroatoms selected from N, O, and S, or a five- to seven-membered heterocyclic ring that contains 1 or 2 heteroatoms selected from N, O, and S, and the alkenyl, the alkynyl, the alkyl, the cycloalkyl, the alkoxy, the phenyl, the heteroaromatic ring, and the heterocyclic ring are unsubstituted or substituted with 1 or 3 substituent groups selected from a deuterium atom, a halogen, hydroxyl, cyano, $C_{1-3}$ alkyl, $C_{3-5}$ cycloalkyl, and $C_{1-3}$ alkoxy.

10. The 2-alkynylmannose derivative, a pharmaceutically acceptable salt, or an isotope thereof according to claim 1, wherein
Y is selected from the following groups that are unsubstituted or substituted with 1 to 3 $R_4$ groups, the left side of Y is connected to X, the right side of Y is connected to Z, and the $R_4$ group is selected from a hydrogen atom, a deuterium atom, a halogen, cyano, hydroxyl, $C_{1-8}$ alkyl, $C_{3-8}$ cycloalkyl, and $C_{1-8}$ alkoxy, and the alkyl, the cycloalkyl, and the alkoxy are unsubstituted or substituted with 1 to 3 substituent groups selected from a deuterium atom, a halogen, hydroxyl, cyano, $C_{1-3}$ alkyl, $C_{3-5}$ cycloalkyl, and $C_{1-3}$ alkoxy.

11. The 2-alkynylmannose derivative, a pharmaceutically acceptable salt, or an isotope thereof according to claim 1, comprising:

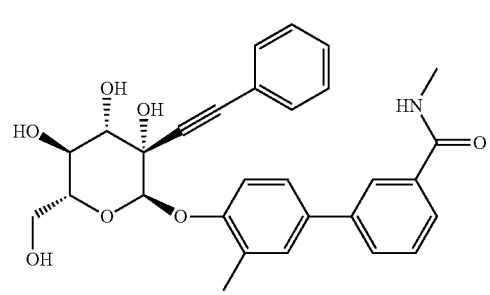

A1

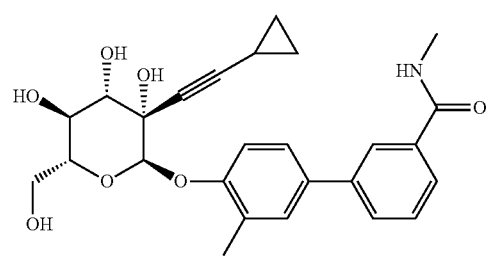

A2

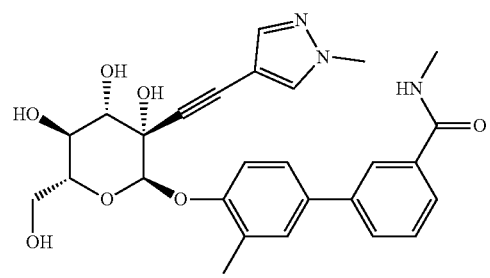

A3

A4
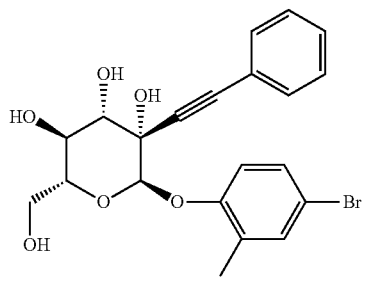
A5
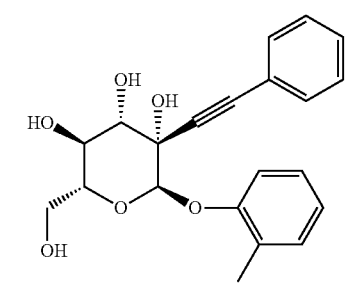
A6
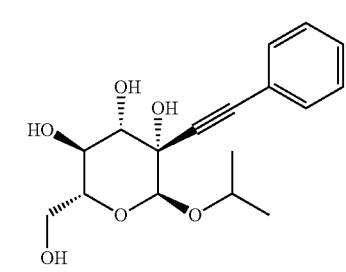
A7
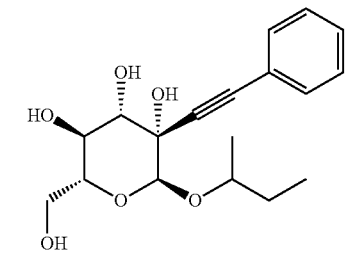
A8
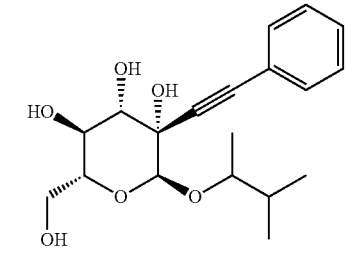
A9
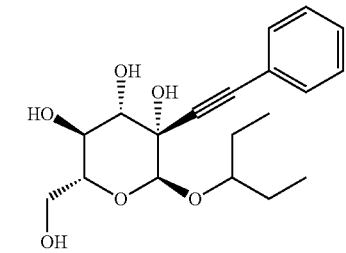
A10
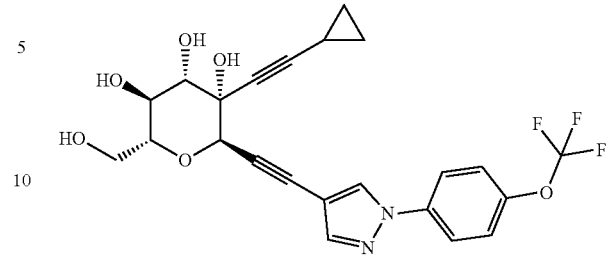
A11
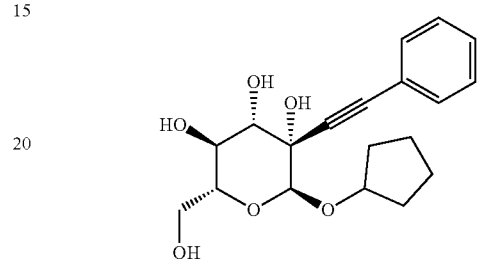
A12
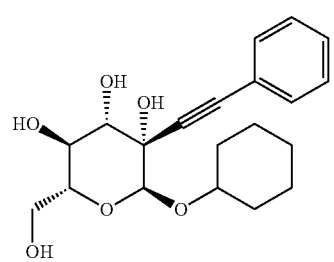
A13
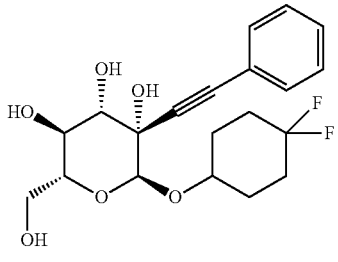
A14
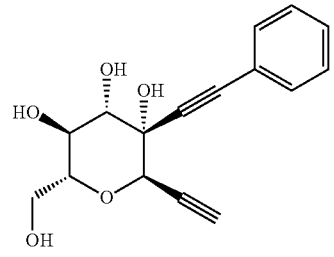
A15
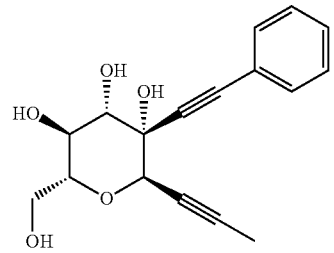

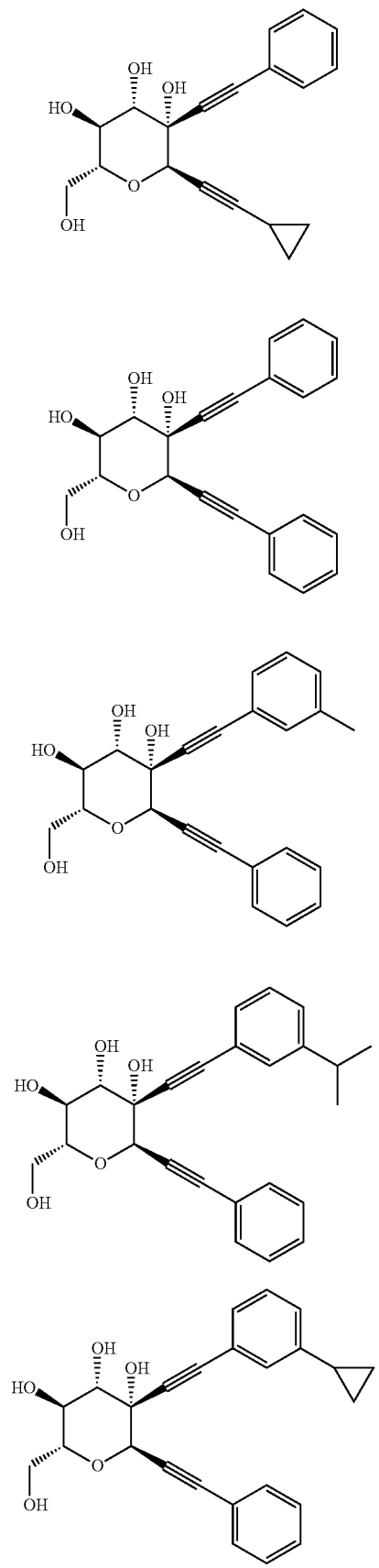
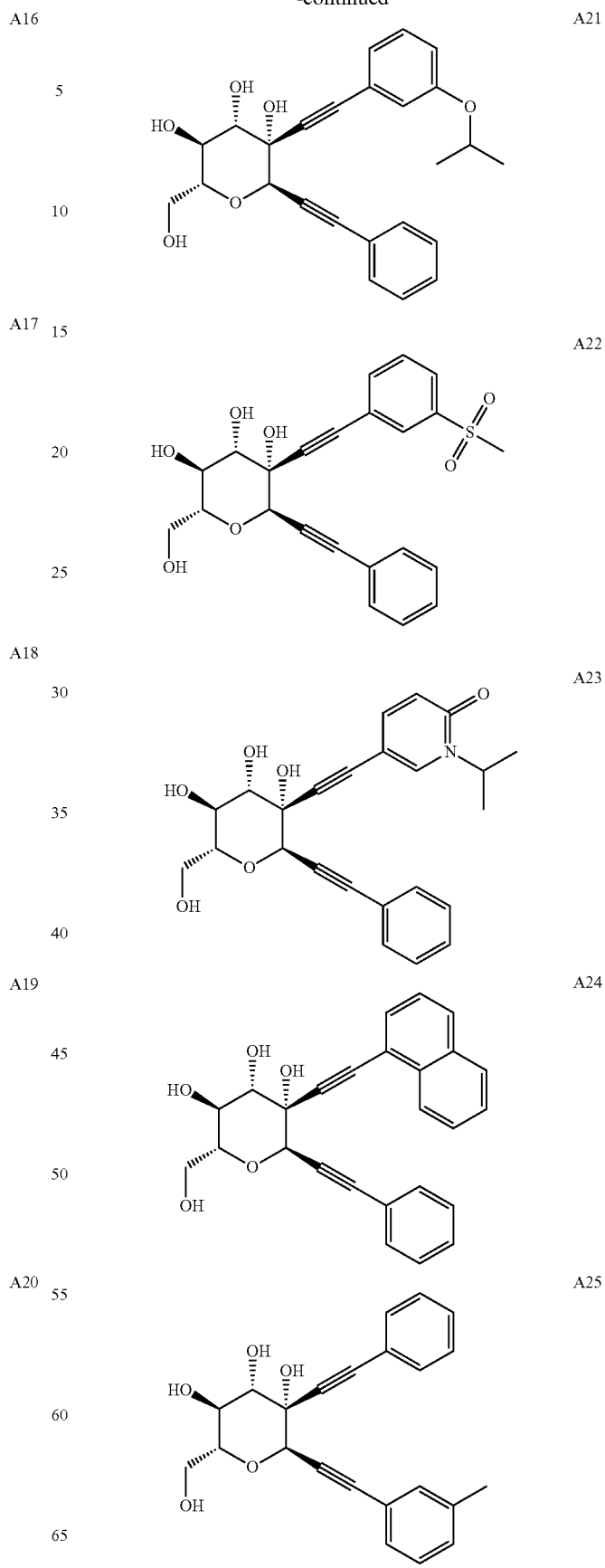

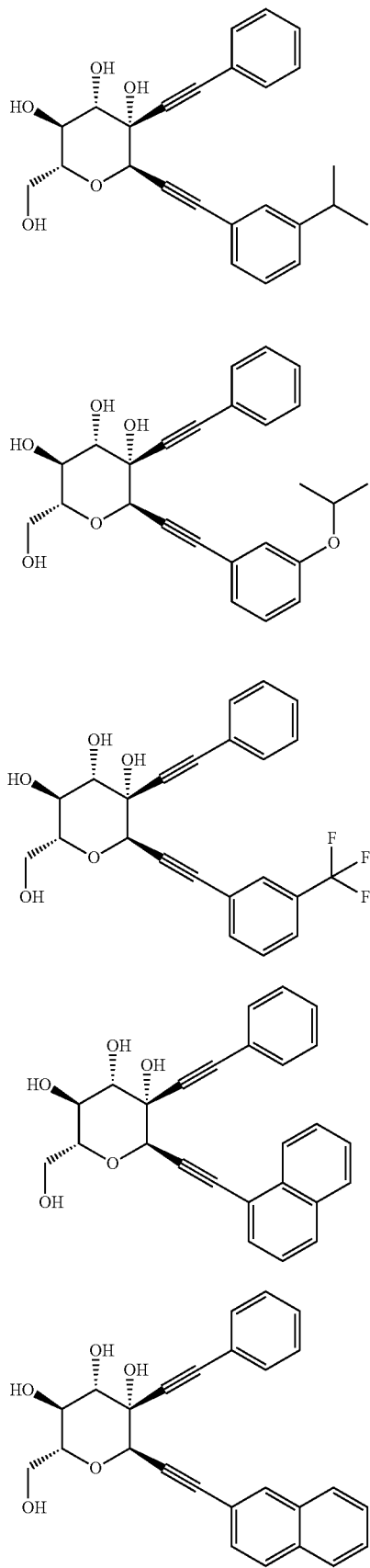
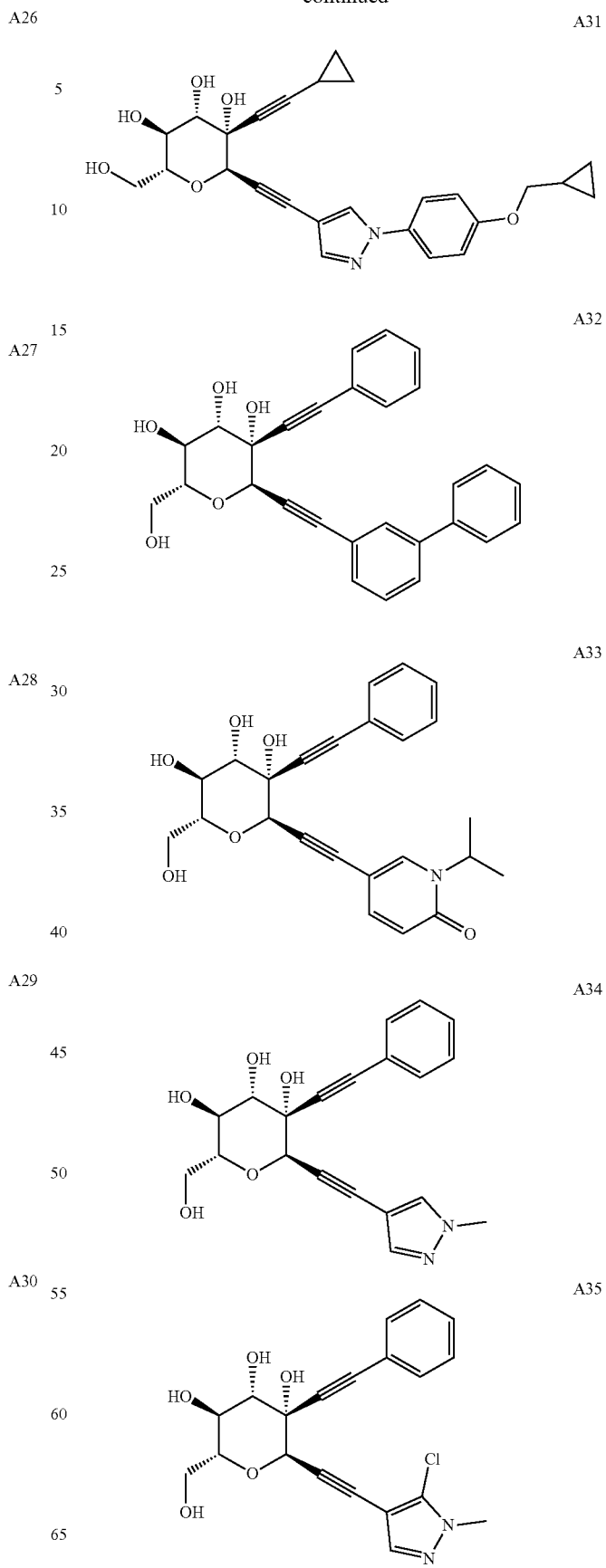

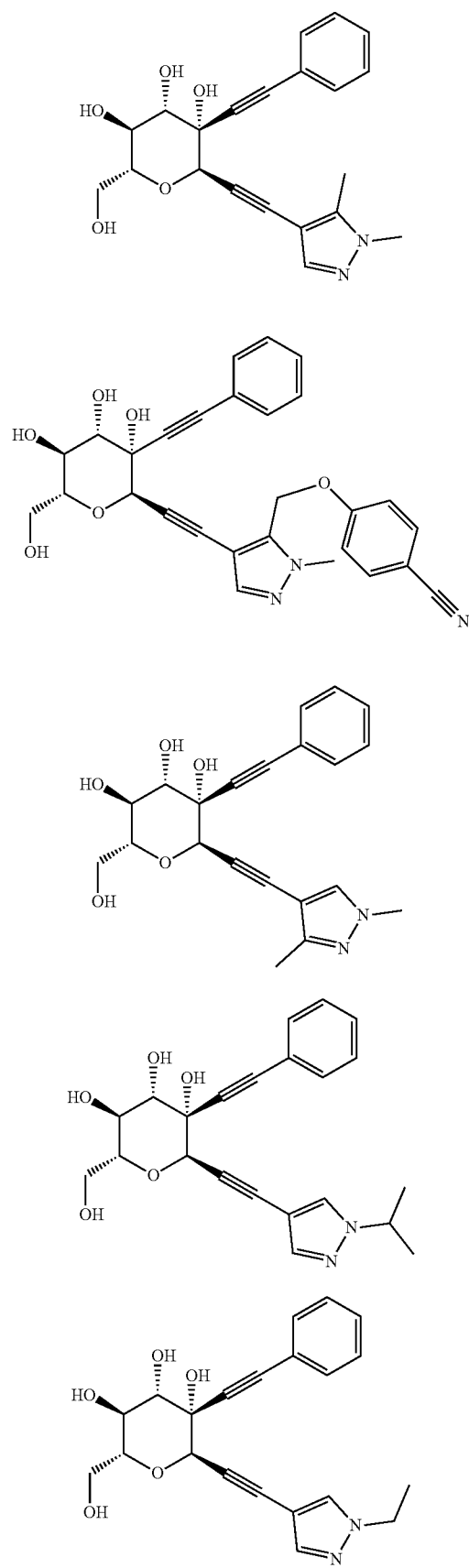

A46
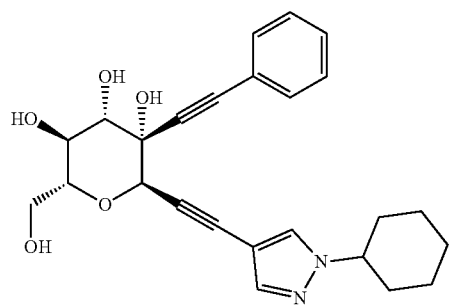
A47
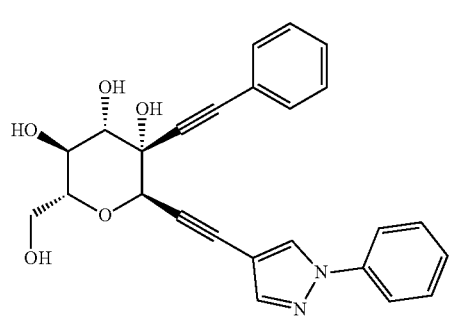
A48
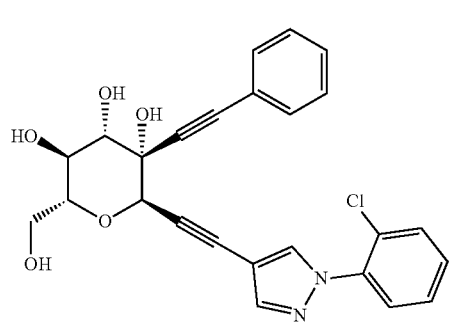
A49
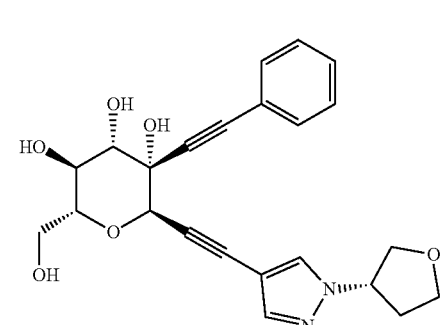
A50
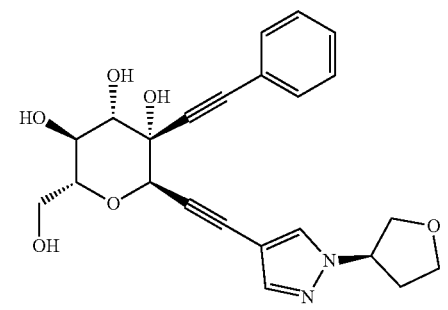
A51
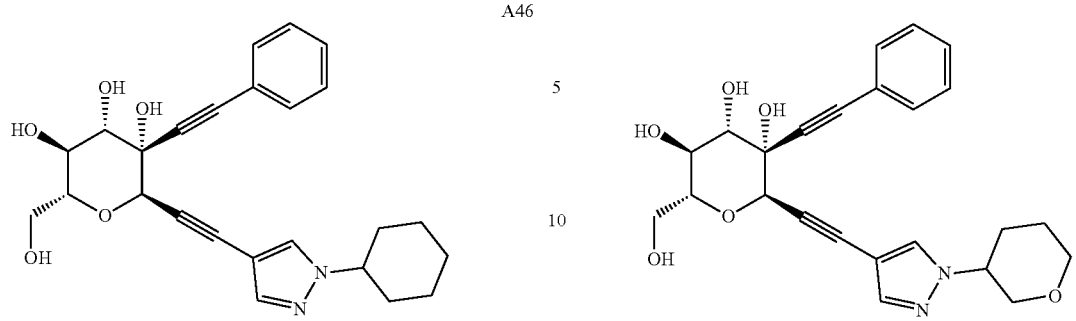
A52
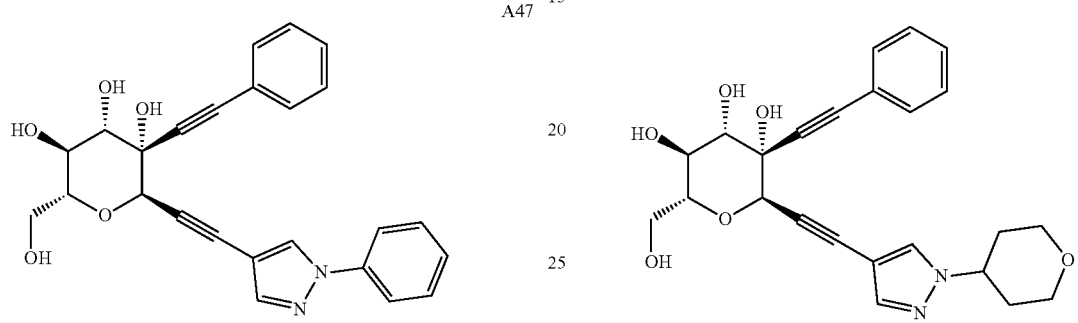
A53
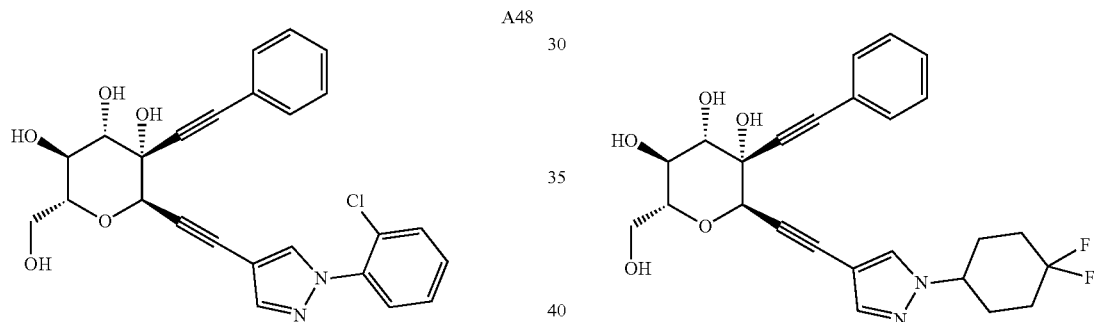
A54
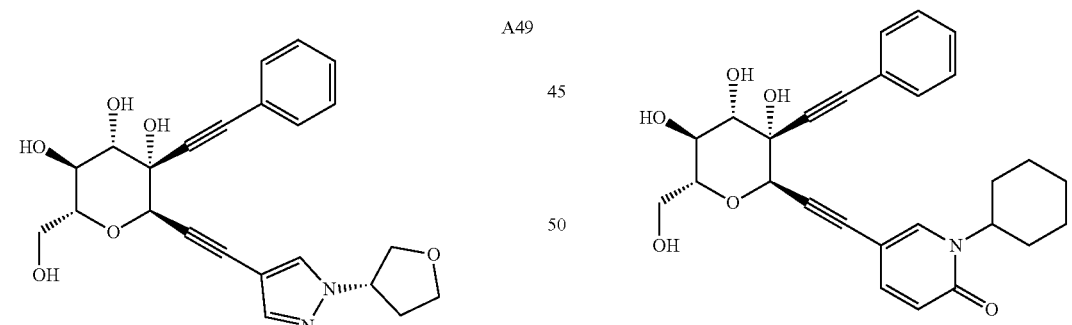
A55
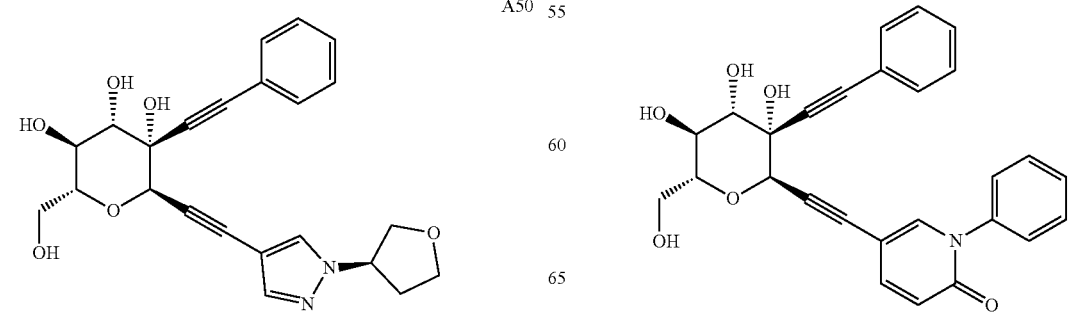

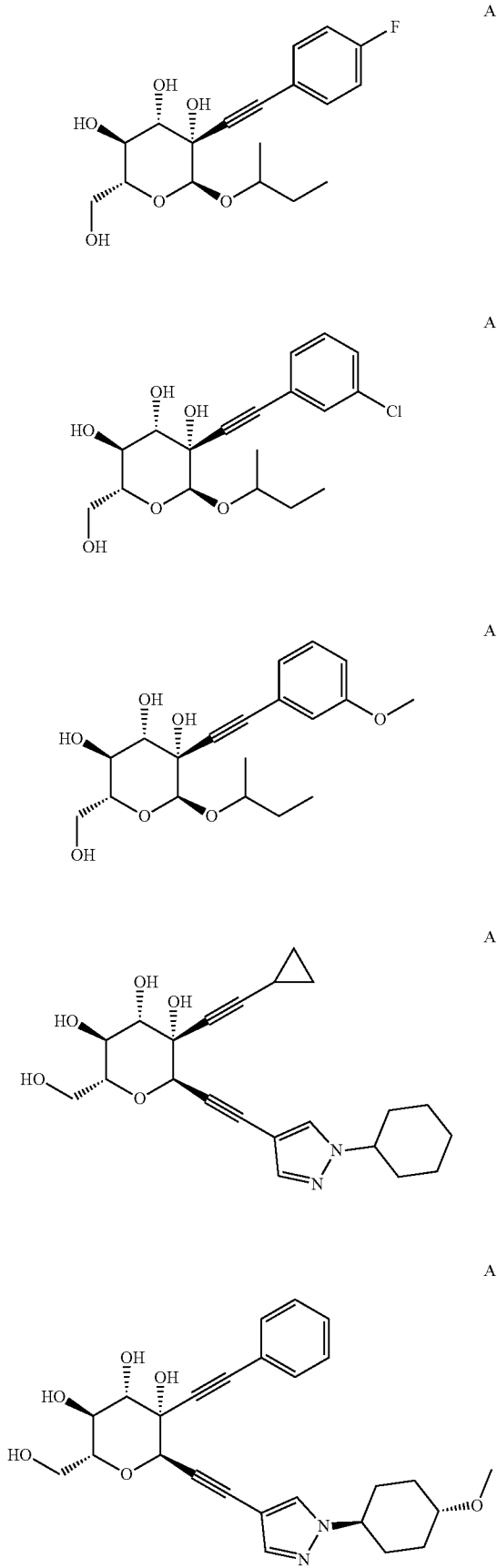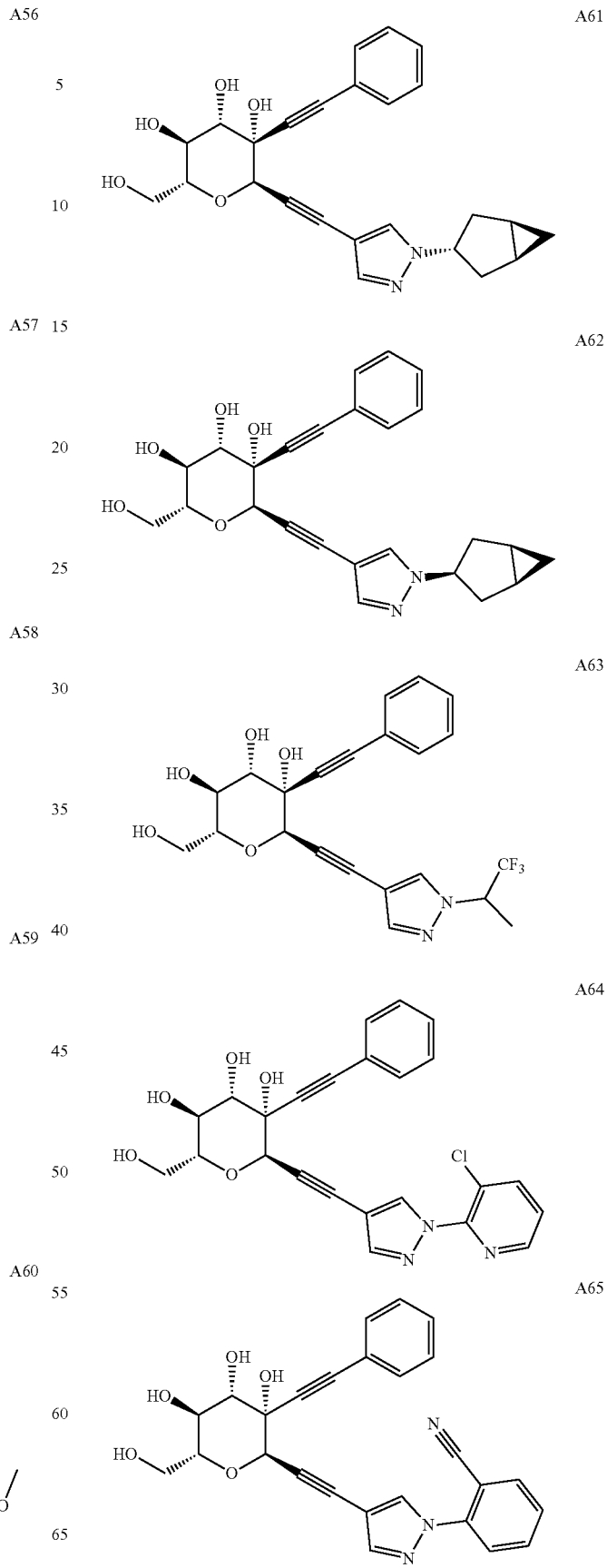

A66
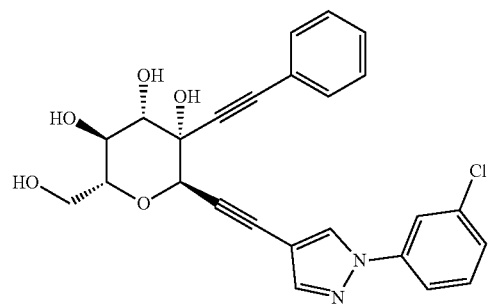
A67
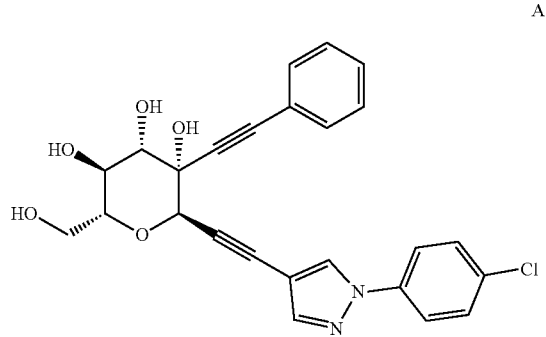
A68
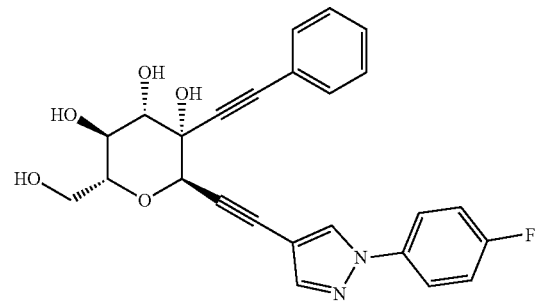
A69
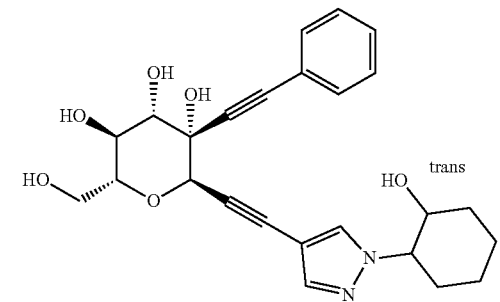
A70
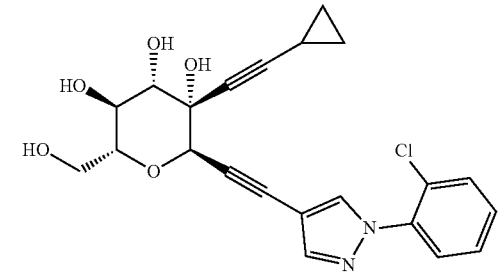
A71
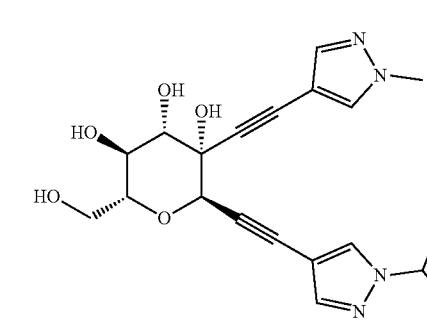
A72
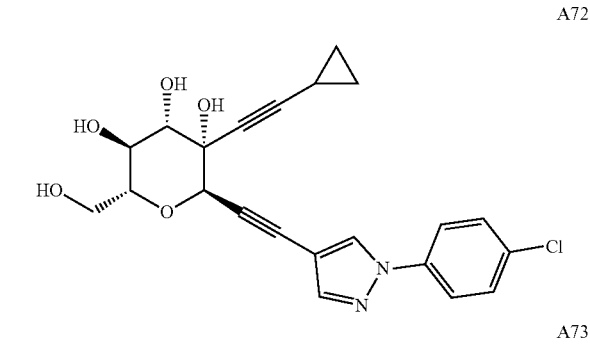
A73
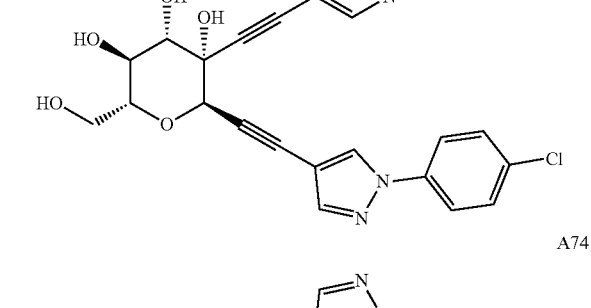
A74
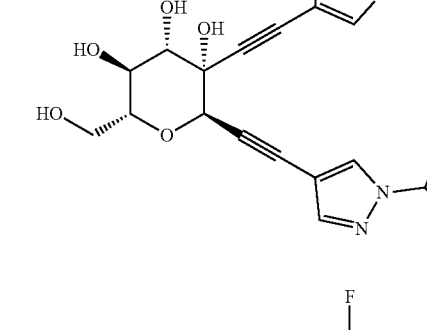
A75
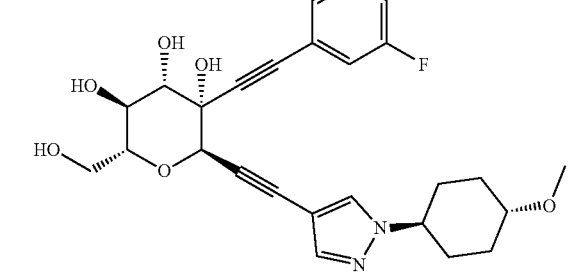

A76
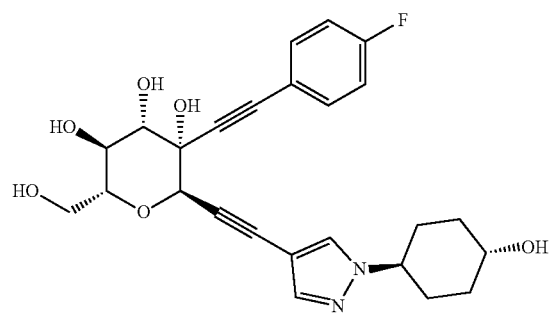
A77
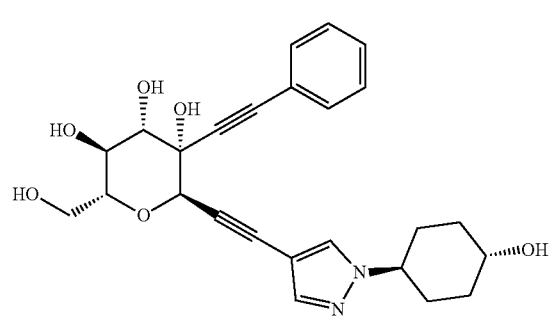
A78
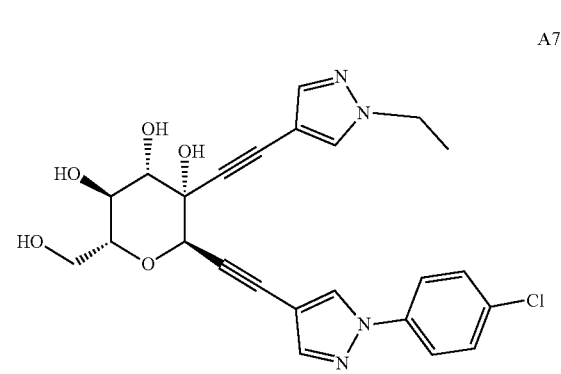
A79
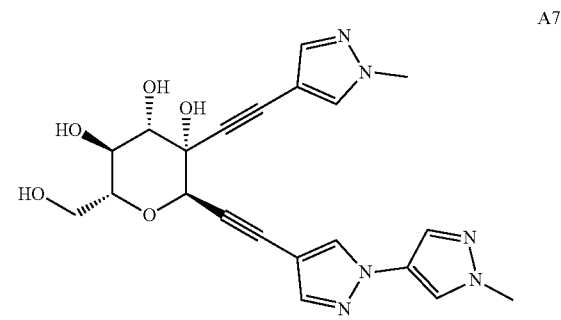
A80
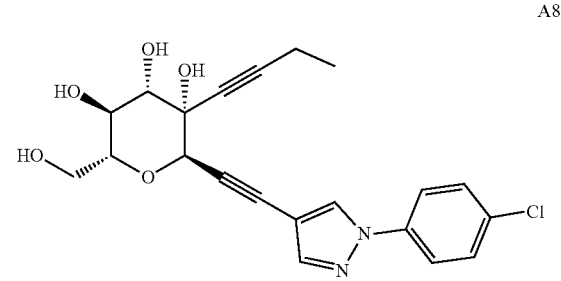
A81
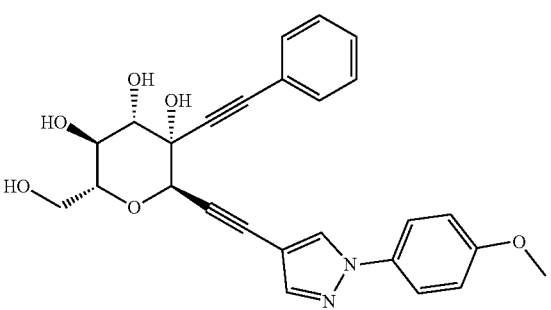
A82
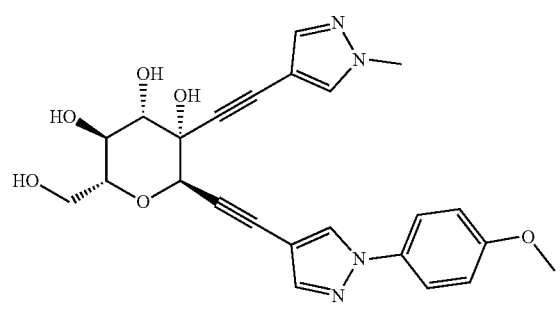
A83
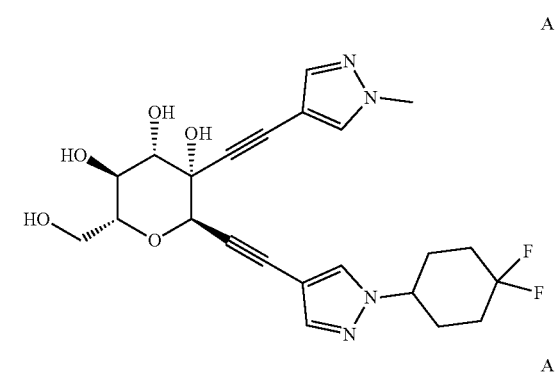
A84
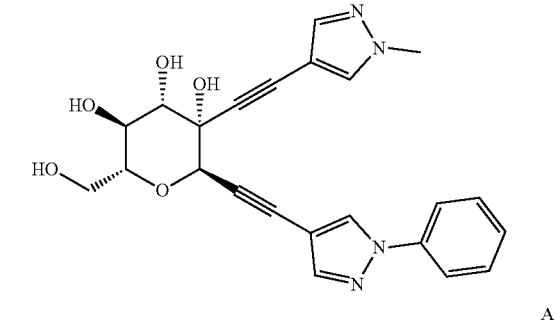
A85
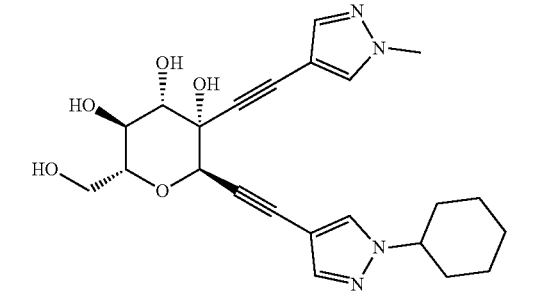

137
-continued
A86
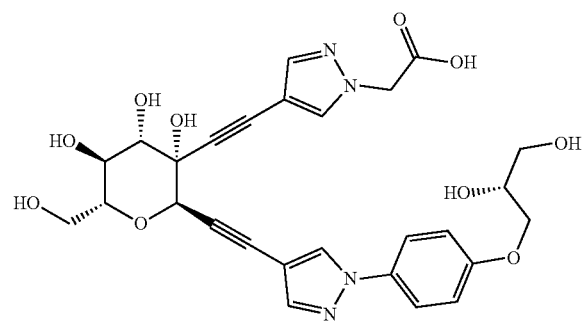
A87
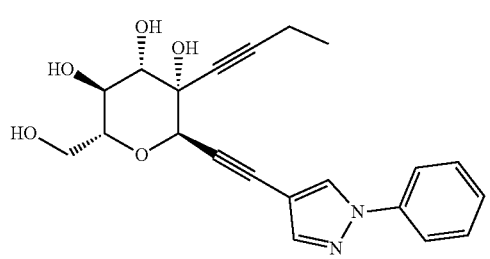
A88
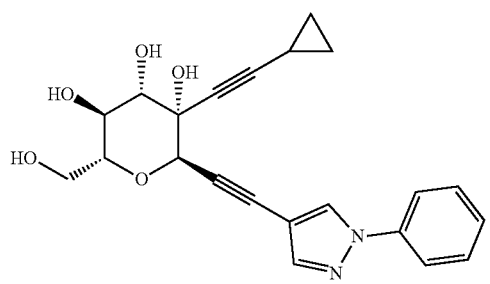
A89
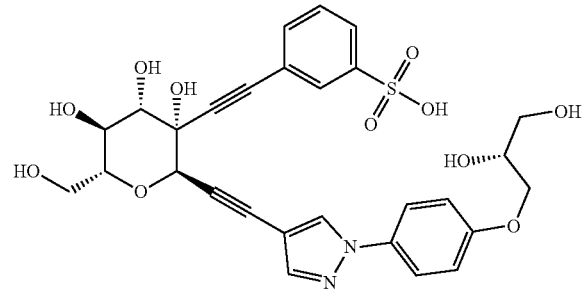
A90
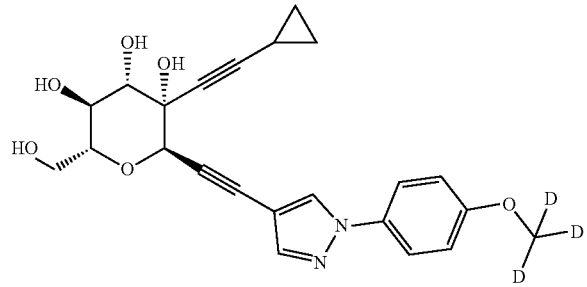
138
-continued
A91
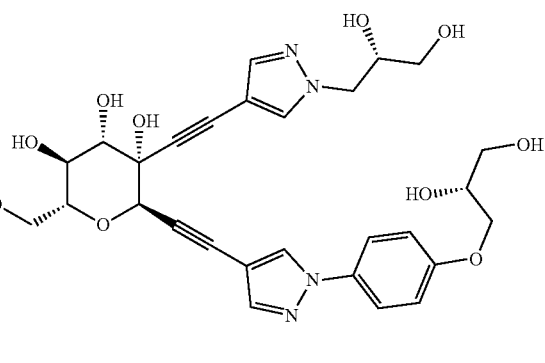
A92
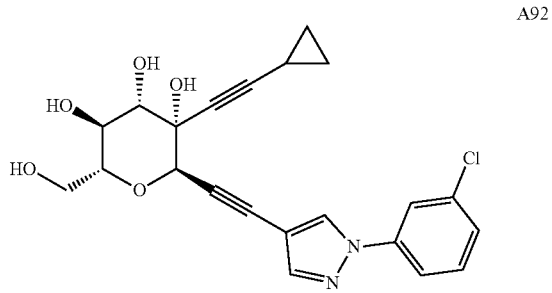
A93
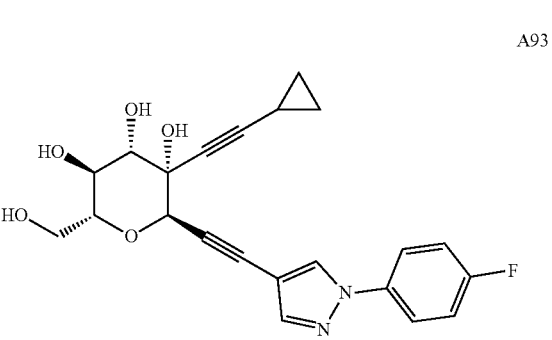
A94
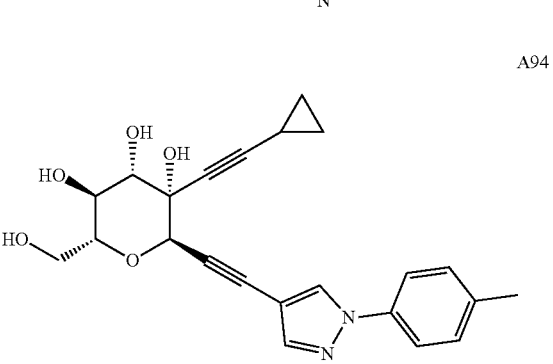
A95
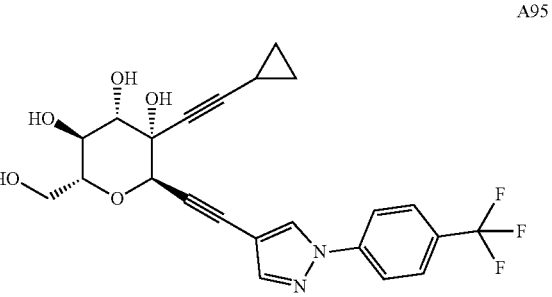

A96
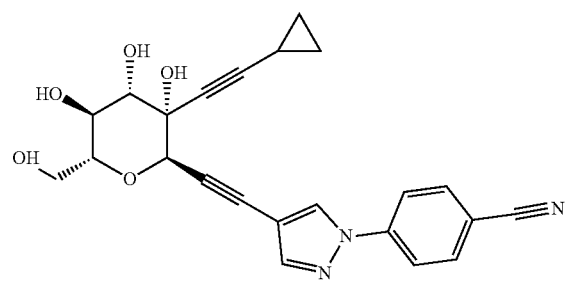
A97
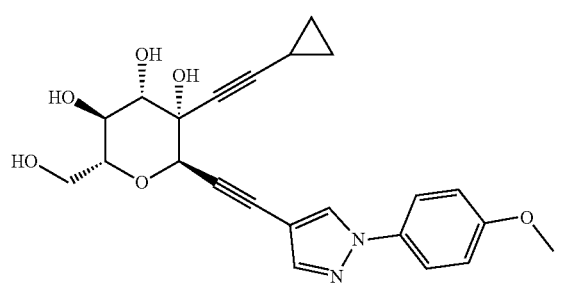
A98
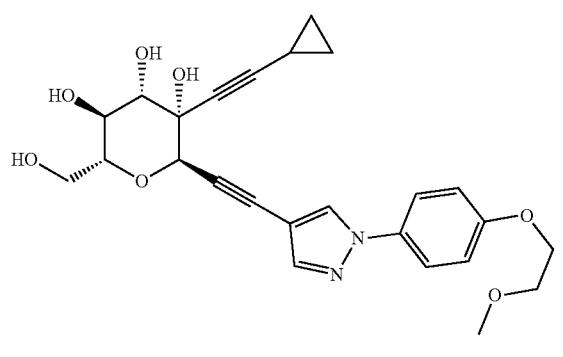
A99
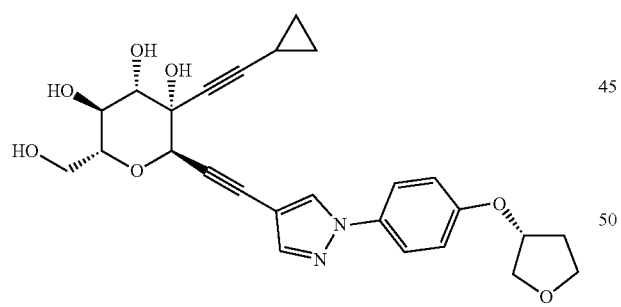
A100
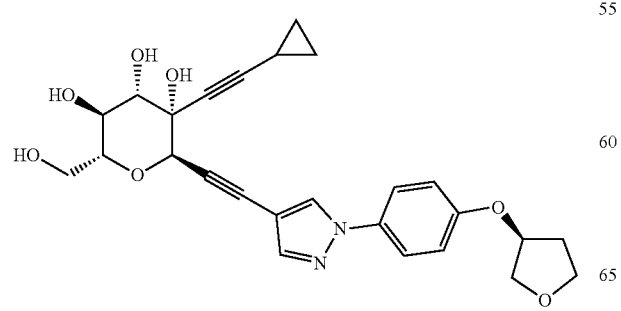
A101
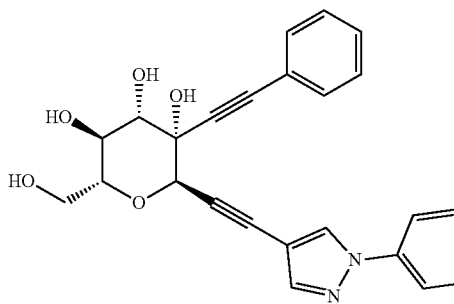
A102
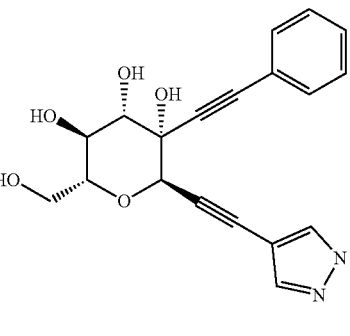
A103
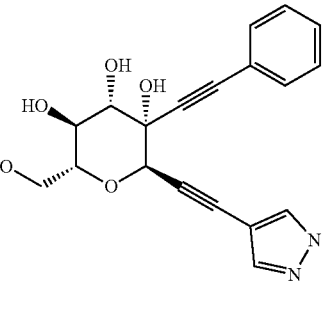

-continued
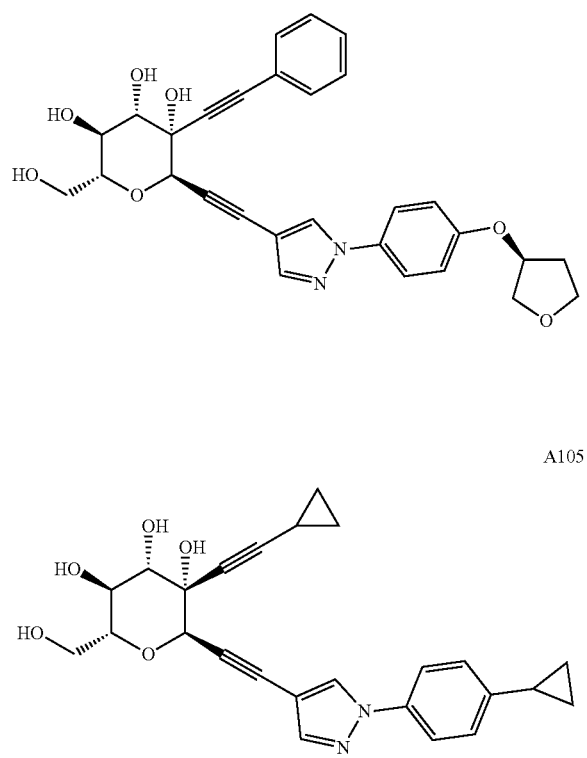
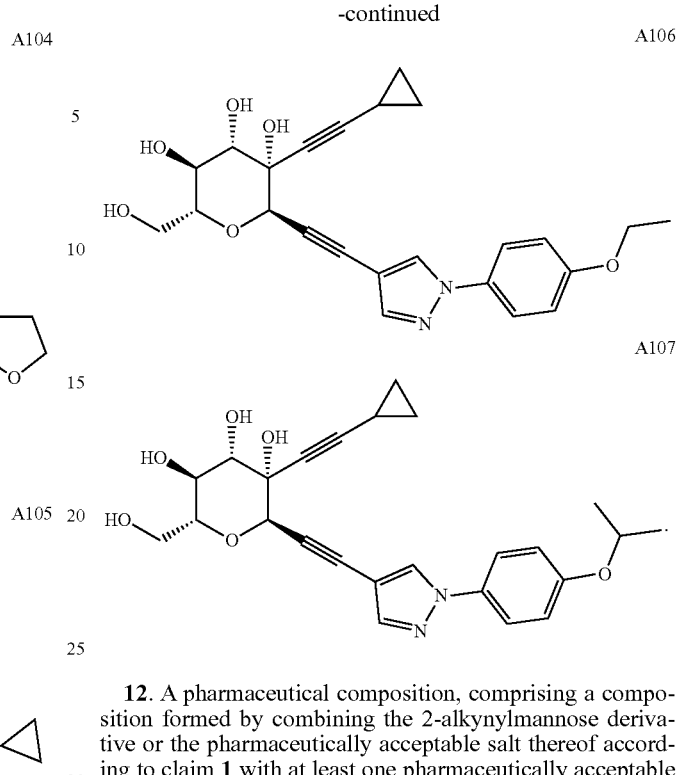
12. A pharmaceutical composition, comprising a composition formed by combining the 2-alkynylmannose derivative or the pharmaceutically acceptable salt thereof according to claim 1 with at least one pharmaceutically acceptable carrier or diluent.
* * * * *